US006521776B2

(12) United States Patent
Hawkins et al.

(10) Patent No.: US 6,521,776 B2
(45) Date of Patent: *Feb. 18, 2003

(54) IMMUNOLOGICAL ADJUVANT COMPOUNDS COMPOSITIONS AND METHODS OF USE THEREOF

(75) Inventors: Lynn D. Hawkins, Concord, MA (US); Sally T. Ishizaka, Weston, MA (US); Jeffrey Rose, Chelmsford, MA (US); Hu Yang, North Andover, MA (US)

(73) Assignee: Eisai Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/919,049

(22) Filed: Jul. 30, 2001

(65) Prior Publication Data

US 2002/0049314 A1 Apr. 25, 2002

Related U.S. Application Data

(60) Provisional application No. 60/221,752, filed on Jul. 31, 2000.

(51) Int. Cl.$^7$ .......................... C07F 9/09; A61K 39/395
(52) U.S. Cl. ................. 558/159; 424/184.1; 424/278.1
(58) Field of Search ................................ 558/155, 156, 558/158, 159; 424/184.1, 278.1

(56) References Cited

U.S. PATENT DOCUMENTS

| | | | | |
|---|---|---|---|---|
| 5,895,653 A | * | 4/1999 | Eibl et al. ................ | 424/204.1 |
| 5,904,925 A | | 5/1999 | Exner | |
| 5,961,970 A | | 10/1999 | Lowell et al. | |
| 5,985,284 A | | 11/1999 | Lowell | |
| 6,146,632 A | | 11/2000 | Momin et al. | |
| 6,165,502 A | | 12/2000 | Oleske et al. | |
| 6,290,973 B1 | | 9/2001 | Hawkins et al. | |
| 6,306,404 B1 | * | 10/2001 | LaPosta et al. ........... | 424/278.1 |

FOREIGN PATENT DOCUMENTS

| | | |
|---|---|---|
| WO | 93/04672 | 3/1993 |
| WO | 95/11700 | 5/1995 |
| WO | 00/44758 | 8/2000 |

OTHER PUBLICATIONS

Hoffman, P. et al, Induction of Tumor Cytotoxicity in Murine Bone Marrow Derived Macrophages by Two Synthetic Lipopeptide Analogues, *Biol. Chem. Hoppe–Sayler*, 1989, 370:575–582.

Weismuller, K. et al., "Novel Low–molecular–weight Synthetic Vaccine against Foot and mouth Disease Containing a Potent B–cell and Macrophage Activator", *Vaccine*, 1989, 7:29–33.

Weismuller, K. et al., "Solid Phase Peptide Synthesis of Lipopeptide Vaccines Eliciting Epitope-specific B-, T-helper and T-killer Cell Response", *Int. J. Peptide Protein Res*. 1992, 40: 255–60.

Defoort, J–P. et al., "Macromolecular Assemblage in the Design of a synthetic AIDS Vaccine", *Proc. Natl. Acad. Sci USA*, 1992, 89:3879–3883/.

Toyokuni, T., et al., Synthetic Vaccines: Synthesis of a Dimeric Tn Antigen–Lipopeptide Conjugate that Elicits Immune Responses against Tn–Expressing C=Glycoproteins, *J. Am. Chem. Soc*, 1994, 116:395–396.

Reichel, F., et al., "Synthetic Carbohydrate–based Vaccines: Synthesis of an L–*glycero*–D–*manno*–heptose antigen–T–epitope–lipopeptide Conjugate", *Chem. Commun.*, 1997, 2087–2088.

Kamitakhara, H., et al., "A Lysoganglioside/Poly–L–glutamic Acid Conjugate as a Picomolar Inhibitor of Influenza Hemagglutinin", *Angew. Chem. Int. Ed.*, 1998, 37:1524–1528.

Dullenkopf, W., et al., "Synthesis of a Structurally Defined Antigen–Immunostimulant Combination for Use in Cancer Vaccines,"*Chem. Eur. J.*, 1999, 5:2432–2438.

Inoue K., "Immunological Studies of Phospholipids. II. Syntheses of Cardiolipin and its Analogues", *Chemical and Pharmaceutical Bulletin*, 1968, vol. 16:76–81.

Duralski, A.A. et al., "Synthesis of Isotopically Labelled Cardiolipins", *Tetrahedron Letters, NL, Elsevier Science Publishers*, Amsterdam, 1998, 39:1607–1610.

Jain, M.K et al., "Effect of the Structure of Phospholipid on the Kinetics of Intravesicle Scooting of Phospholipase A2", *Biochim. Biophys. Acta* (BBACAQ, 00063002); 1986, 860:462–74.

Inoue, K. et al., "Immunochemical Studies of Phospholipids. I. Reactivity of Various Synthetic Cardiolipin Derivatives with Wassermann Antibody", *Chem. Phys. Lipids* (CPLIA4), 1967, vol. 1, the entire document.

Inoue, K., et al., "Immunochemical Studies of Phospholipids IV: The Reactivities of Antisera Against Natural Cardiolipin and Synthetic Cardiolipin Analoques–Containing Antigens" *Chem. Phys. Lipids*, 1969, 3:70–77.

Gregoriadies, G. et al., "Liposomes as Immunological Adjuvants and Vaccine Carriers", *Journal of Controlled Release*, NL, Elsevier Science Publishers B.V. Amsterdam, 1996, 41:49–56.

Vogel, F.R., "Immunologic Adjuvants for Modern Vaccine Formulations", *Annals of the New York Academy of Sciences*, 1995, 153–160.

\* cited by examiner

Primary Examiner—Joseph K. McKane
Assistant Examiner—Golam M. M. Shameem
(74) Attorney, Agent, or Firm—Hale and Dorr LLP

(57) ABSTRACT

The present invention provides novel compounds that function as immunological adjuvants when co-administered with antigens, including, antigens used as vaccines for any disease or condition amenable to vaccination. The invention also provides adjuvant formulations comprising the novel compounds of the invention and methods for immunizing humans and non-human animals.

16 Claims, No Drawings

IMMUNOLOGICAL ADJUVANT COMPOUNDS COMPOSITIONS AND METHODS OF USE THEREOF

This application claims benefit of No. 60/221,752 filed Jul. 31, 2000.

BACKGROUND OF THE INVENTION

Vaccines have proven to be successful, highly acceptable methods for the prevention of infectious diseases. They are cost effective, and do not induce antibiotic resistance to the target pathogen or affect normal flora present in the host. In many cases, such as when inducing antiviral immunity, vaccines can prevent a disease for which there are no viable curative or ameliorative treatments available.

Vaccines function by triggering the immune system to mount a response to an agent, or antigen, typically an infectious organism or a portion thereof that is introduced into the body in a non-infectious or non-pathogenic form. Once the immune system has been "primed" or sensitized to the organism, later exposure of the immune system to this organism as an infectious pathogen results in a rapid and robust immune response that destroys the pathogen before it can multiply and infect enough cells in the host organism to cause disease symptoms.

The agent, or antigen, used to prime the immune system can be the entire organism in a less infectious state, known as an attenuated organism, or in some cases, components of the organism such as carbohydrates, proteins or peptides representing various structural components of the organism, or nucleic acids encoding such components.

In many cases, it is necessary to enhance the immune response to the antigens present in a vaccine in order to stimulate the immune system to a sufficient extent to make a vaccine effective, i.e., to confer immunity. Many protein and most peptide and carbohydrate antigens, administered alone, do not elicit a sufficient antibody response to confer immunity. Such antigens need to be presented to the immune system in such a way that they will be recognized as foreign and will elicit an immune response. To this end, additives (adjuvants) have been devised which enhance the immune response.

The best known adjuvant, Freund's complete adjuvant, consists of a mixture of mycobacteria in an oil/water emulsion. Freund's adjuvant works in two ways: first, by enhancing cell and humoral-mediated immunity, and second, by blocking rapid dispersal of the antigen challenge (the "depot effect"). However, due to frequent toxic physiological and immunological reactions to this material, Freund's adjuvant cannot be used in humans.

Another molecule that has been shown to have immunostimulatory or adjuvant activity is endotoxin, also known as lipopolysaccharide (LPS). LPS stimulates the immune system by triggering an "innate" immune response—a response that has evolved to enable an organism to recognize endotoxin (and the invading bacteria of which it is a component) without the need for the organism to have been previously exposed. While LPS is too toxic to be a viable adjuvant, molecules that are structurally related to endotoxin, such as monophosphoryl lipid A ("MPL") are being tested as adjuvants in clinical trials. Currently, however, the only FDA-approved adjuvant for use in humans is aluminum salts (Alum) which are used to "depot" antigens by precipitation of the antigens. Alum also stimulates the immune response to antigens.

Thus, there is a recognized need in the art for compounds which can be co-administered with antigens in order to stimulate the immune system to generate a more robust response to the antigen than would be seen if the antigen were injected alone or with Alum.

SUMMARY OF THE INVENTION

In one aspect, the invention provides novel compounds that are capable of enhancing an immune response in an animal when administered to the animal. In one embodiment, the compounds of the invention function as immunological adjuvants when co-administered with antigens, including antigens used as vaccines for any disease or condition amenable to vaccination. The novel adjuvant compounds of the invention have the formula I.

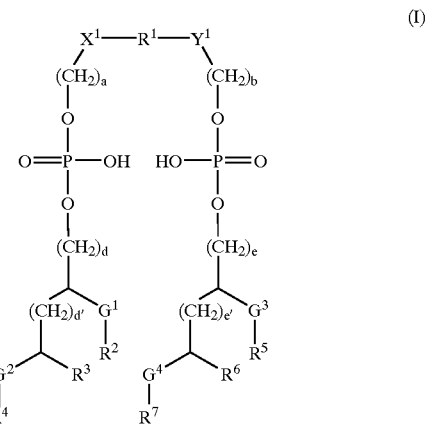

(I)

wherein $R^1$ is selected from the group consisting of
(a) —C(O)—;
(b) —C(O)—$C_{1-14}$ alkylene-C(O)— or —C(O)—$C_{1-14}$ alkenylene-C(O)—, wherein the $C_{1-14}$ alkylene or $C_{1-14}$ alkenylene is optionally substituted with hydroxy, $C_{1-6}$ alkoxy, $C_{1-6}$ alkylenedioxy, carboxy, $C_{1-6}$ alkoxycarbonyl, $C_{1-6}$ carbamoyl, $C_{1-6}$ acylamino, $C_{1-6}$ alkylamino, or (aryl)$C_{1-6}$ alkyl, wherein said aryl moiety of said (aryl)$C_{1-6}$ alkyl is optionally substituted with $C_{1-6}$ alkyl, $C_{1-6}$ alkoxy, $C_{1-6}$ alkylamino, ($C_{1-6}$ alkoxy)$C_{1-6}$ alkylamino, ($C_{1-6}$ alkylamino)$C_{1-6}$ alkoxy, —O—$C_{1-6}$ alkylene-NH—$C_{1-6}$alkylene-O—$C_{1-6}$ alkyl, —O—$C_{1-6}$ alkylene-NH—C(O)—$C_{1-6}$ alkylene-C(O)OH, or —O—$C_{1-6}$ alkylene-NH—C(O)—$C_{1-6}$ alkylene-C(O)—$C_{1-6}$ alkyl;
(c) $C_2$ to $C_{15}$ straight or branched chain alkyl optionally substituted with hydroxy or alkoxy; and
(d) —C(O)—$C_{6-12}$ arylene-C(O)— wherein said arylene is optionally substituted with $C_{1-6}$ alkyl, hydroxy, $C_{1-6}$ alkoxy, halogen, nitro or amino;
a and b are independently an integer from 0 to about 4;
d and e are independently an integer from 1 to about 6;
d' and e' are independently an integer from 0 to about 2;
$X^1$ and $Y^1$ are independently selected from the group consisting of a null, oxygen, —NH—, —N(C(O)$C_{1-4}$ alkyl)-, and —N($C_{1-4}$ alkyl)-;
$G^1$, $G^2$, $G^3$, and $G^4$ are independently selected from the group consisting of oxygen, methylene, —NH—, —N($C_{1-4}$ alkyl)-, —N[C(O)—$C_{1-4}$ alkyl]-, —NH—C (O)—, —NH—SO$_2$—, —C(O)—O—, —C(O)—NH—, —O—C(O)—, —O—C(O)—NH—, —O—C (O)—O—, —NH—C(O)—NH—, —C(O)NH—, C(O)N($C_{1-4}$ alkyl), and —S(O)$_n$—, where n is 0, 1, or 2;

$R^2$, $R^3$, $R^4$, $R^5$, $R^6$, and $R^7$ are independently selected from the group consisting of:
(a) $C_1$ to $C_{20}$ straight chain or branched chain alkyl which is optionally substituted with halo, oxo, hydroxy or alkoxy;
(b) $C_2$ to $C_{20}$ straight chain or branched chain alkenyl, alkynyl, or dialkenyl which is optionally substituted with halo, oxo, hydroxy or alkoxy; and (c)

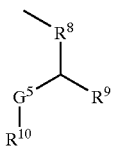

wherein
$R^8$ is $C_{1-6}$ straight or branched chain alkyl or $C_{2-6}$ straight or branched chain alkenyl, alkynyl, or dialkenyl;
$G^5$ is selected from the group consisting of oxygen, methylene, arylene, —NH—, —N($C_{1-4}$ alkyl)-, —N(C(O)—$C_{1-4}$ alkyl)-, —NH—C(O)—, —NH—SO$_2$—, —C(O)—O—, —C(O)—NH—, —O—C(O)—, —O—C(O)—NH—, —O—C(O)—O—, —NH—C(O)—NH—, and —S(O)$_n$—, where n is 0, 1, or 2;
$R^9$ and $R^{10}$ are independently selected from the group consisting of
(i) $C_1$ to $C_{20}$ straight chain or branched chain alkyl which is optionally substituted with halo, oxo, hydroxy or alkoxy; and
(ii) $C_2$ to $C_{20}$ straight chain or branched chain alkenyl, alkynyl, or dialkenyl which is optionally substituted with halo, oxo, hydroxy or alkoxy;
or any one or two of $G^1R^2$, $G^2R^4$, $G^3R^5$, and $G^4R^7$ may together be a hydrogen atom or hydroxyl;
or a pharmaceutically acceptable salt thereof.

In a second aspect, the present invention is directed to novel immunological formulations which comprise at least one of the adjuvant compounds of the invention.

In a third aspect, the invention is directed to novel immunological compositions which comprise an antigen and at least one of the adjuvant compounds of the invention.

In another aspect, the present invention is directed to methods for enhancing an immune response in an animal, comprising administering to the animal a compound of the invention.

DETAILED DESCRIPTION OF THE PREFERRED EMBODIMENTS

The invention provides novel compounds that are capable of enhancing an immune response in an animal when administered to the animal. In certain preferred embodiments, the compounds of the invention are capable of producing in immunological effect when administered alone. In certain other preferred embodiments, the compounds of the invention function as immunological adjuvants when co-administered with antigens, including antigens used as vaccines for any disease or condition amenable to vaccination. The invention also provides immunological compositions comprising the novel compounds of the invention and methods for immunizing humans and non-human animals.

The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used:
Definitions The term "immunological composition", as used herein, is intended to include compositions capable of producing any effect on the immune system of an animal, including, without limitation, an immunoprophylactic, immunotherapeutic, immunopotentiating, or immunosuppressive effect.

The term "animal", as used herein, refers to human patients and non-human animals. Non-human animals include any animal that is capable of mounting an immune response to a vaccine.

The terms "carbonyl" and "oxo", as used herein, refer to a (C=O) moiety. A carbonyl group may also be represented as —C(O)—.

The term "dicarbonyl", as used herein, refers to a moiety with the structure —C(O)-alkylene-C(O)— or —C(O)-arylene-C(O)—, which is bonded to a molecule through the carbon atoms of both terminal carbonyl moieties.

An "alkyl ester", as used herein, is a moiety with the structure —O—C(O)-alkyl, which is bonded to a molecule through the singly bonded oxygen of the ester group. The term "alkoxycarbonyl" refers to a moiety with the structure —(O)—O-alkyl, which is bonded to a molecule through the carbonyl carbon atom.

An "alkenyl ester", as used herein, is a moiety with the structure —O—C(O)— carbon chain, where the carbon chain contains a carbon-to-carbon double bond, wherein the ester moiety is bonded to a molecule through its singly bonded oxygen atom.

The term "alkylene" means a bivalent straight chain or branched alkyl hydrocarbon group.

The term "alkenylene" means a bivalent straight chain or branched hydrocarbon group having at least one carbon to carbon double bond.

The term "dialkenylene" means a bivalent unsaturated straight chain or branched chain hydrocarbon group having at least two carbon to carbon double bonds.

The term "arylene" refers to a bivalent aromatic group.

Where the terms "alkylene", "alkenylene", or "dialkenylene" include a descriptor indicating the number of carbon atoms or a range in the number of carbon atoms, e.g., $C_{1-14}$ alkylene, the number of carbon atoms refers to the length of the carbon chain connecting the two chemical groups between which the alkylene group is positioned. When the term "arylene" includes a descriptor indicating the number of carbon atoms or a range in the number of carbon atoms, the number of carbon i atoms refers to the number of carbon atoms in the aromatic ring system. Any of the carbon atoms of an alkylene, alkenylene, dialkenylene, or arylene group may be optionally substituted, as described below, and the substituents may contain additional carbon atoms.

The term "alkyl" as employed herein refers to straight and branched chain aliphatic groups having from 1 to 20 carbon atoms, which may be optionally substituted with one, two or three substituents.

An "aryl" group is a $C_6$–$C_{14}$ aromatic moiety comprising one to three aromatic rings, which may be optionally substituted. Preferably, the aryl group is a $C_6$–$C_{10}$ aryl group. The term "aryl" is also intended to include heteroaryl groups, comprising 5 to 14 ring atoms, preferably 5, 6, 9, or 10 ring atoms; having 6, 10, or 14π electrons shared in a cyclic array; and having, in addition to carbon atoms, from one to about three heteroatoms selected from the group consisting of N, O, and S.

An "aralkyl" or "arylalkyl" group comprises an aryl group, as defined above, which is covalently linked to an alkyl group, either of which independently may be optionally substituted or unsubstituted.

The term "halogen" or "halo" as employed herein refers to chlorine, bromine, fluorine, or iodine.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted.

Unless otherwise explicitly limited, the term "amino" is meant to include $NH_2$, alkylamino, dialkylamino, arylamino, aralkylamino, and cyclic amino groups.

As herein employed, the term "acyl" refers to an alkylcarbonyl or arylcarbonyl substituent.

The abbreviation "Boc" as used herein refers to t-butyloxycarbonyl.

The term "null" as used herein with reference to a given substituent means that the substituent is absent, and the chemical groups between which the substituent is positioned are directly attached to each other by way of a covalent chemical bond.

As used herein with reference to compounds and compositions of the invention, the term "type 1" refers to those compounds of the invention corresponding to formula I above where the values of a and b are the same; the values of d and e are the same; the values of d' and e' are the same; $X^1$ and $Y^1$ are the same; $G^1$ and $G^3$ are the same; $G^2$ and $G^4$ are the same; $R^2$ and $R^5$ are the same; $R^3$ and $R^6$ are the same; and $R^4$ and $R^7$ are the same.

The term "type 2", as used herein, refers to compounds or compositions corresponding to formula I where any one or more of the following applies: the values of a and b are the different; the values of d and e are the different; the values of d' and e' are the different; $X^1$ and $Y^1$ are the different; $G^1$ and $G^3$ are the different; $G^2$ and $G^4$ are the different; $R^2$ and $R^5$ are the different; $R^3$ and $R^6$ are the different; and $R^4$ and $R^7$ are the different.

Compounds

In a first aspect, the present invention provides novel compounds of formula I:

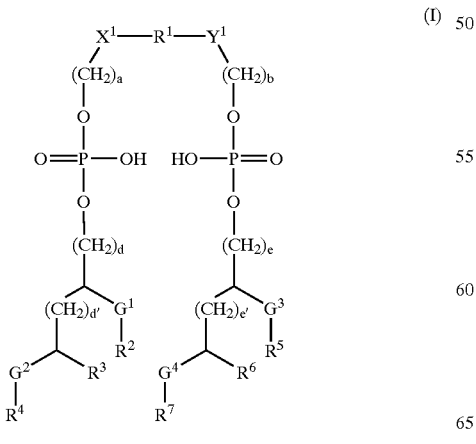

wherein
$R^1$ is selected from the group consisting of
(a) —C(O)—;
(b) —C(O)—$C_{1-14}$ alkylene-C(O)— or —C(O)—$C_{1-14}$ alkenylene-C(O)—, wherein the $C_{1-14}$ alkylene or $C_{1-14}$ alkenylene is optionally substituted with hydroxy, $C_{1-6}$ alkoxy, $C_{1-6}$ alkylenedioxy, carboxy, $C_{1-6}$ alkoxycarbonyl, $C_{1-6}$ carbamoyl, $C_{1-6}$ acylamino, $C_{1-6}$ alkylamino, or (aryl)$C_{1-6}$ alkyl, wherein said aryl moiety of said (aryl)$C_{1-6}$ alkyl is optionally substituted with $C_{1-6}$ alkyl, $C_{1-6}$ alkoxy, $C_{1-6}$ alkylamino, ($C_{1-6}$ alkoxy)$C_{1-6}$ alkylamino, ($C_{1-6}$ alkylamino)$C_{1-6}$ alkoxy, —O—$C_{1-6}$ alkylene-NH—$C_{1-6}$alkylene—O—$C_{1-6}$ alkyl, —O—$C_{1-6}$ alkylene-NH—C(O)—$C_{1-6}$ alkylene-C(O)OH, or —O—$C_{1-6}$ alkylene-NH—C(O)—$C_{1-6}$ alkylene-(O)—$C_{1-6}$ alkyl;
(c) $C_2$ to $C_{15}$ straight or branched chain alkyl optionally substituted with hydroxy or alkoxy; and
(d) —C(O)—$C_{6-12}$ arylene-C(O)— wherein said arylene is optionally substituted with $C_{1-6}$ alkyl, hydroxy, $C_{1-6}$ alkoxy, halogen, nitro or amino;

a and b are independently an integer from 0 to about 4;
d and e are independently an integer from 1 to about 6;
d' and e' are independently an integer from 0 to about 2;
$X^1$ and $Y^1$ are independently selected from the group consisting of a null, oxygen, —NH—, —N(C(O)$C_{1-4}$ alkyl)-, and —N($C_{1-4}$ alkyl)-,
$G^1$, $G^2$, $G^3$, and $G^4$ are independently selected from the group consisting of oxygen, methylene, —NH—, —N($C_{1-4}$ alkyl)-, —N[C(O)—$C_{1-4}$ alkyl]-, —NH—C (O)—, —NH—$SO_2$—, —C(O)—O—, —C(O)—NH—, —O—C(O)—, —O—C(O)—NH—, —O—C (O)—O—, —NH—C(O)—NH—, —C(O)NH—, C(O)N($C_{1-4}$ alkyl), and —S(O)$_n$—, where n is 0, 1, or 2;
$R^2$, $R^3$, $R^4$, $R^5$, $R^6$, and $R^7$ are independently selected from the group consisting of:
(a) $C_1$ to $C_{20}$ straight chain or branched chain alkyl which is optionally substituted with halo, oxo, hydroxy or alkoxy;
(b) $C_2$ to $C_{20}$ straight chain or branched chain alkenyl, alkynyl, or dialkenyl which is optionally substituted with halo, oxo, hydroxy or alkoxy; and

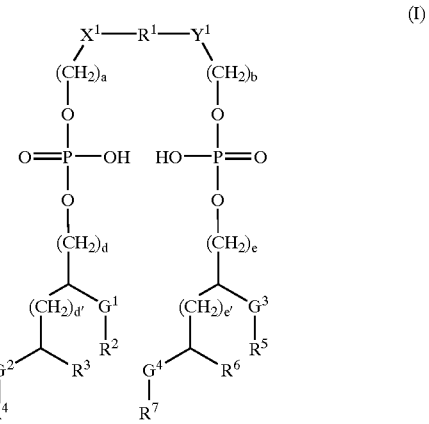

wherein
$R^8$ is $C_{1-6}$ straight or branched chain alkyl or $C_{2-6}$ straight or branched chain alkenyl, alkynyl, or dialkenyl;
$G^3$ is selected from the group consisting of oxygen, methylene, arylene, —NH—, —N($C_{1-4}$ alkyl)-, —N(C(O)—$C_{1-4}$ alkyl)-, —NH—C(O)—, —NH—$SO_2$—, —C(O)—O—, —C(O)—NH—, —O—C(O)—, —O—C(O)—NH—, —O—C(O)—O—, —NH—C(O)—NH—, and —S(O)$_n$—, where n is 0, 1, or 2;

R$^9$ and R$^{10}$ are independently selected from the group consisting of
(i) C$_1$ to C$_{20}$ straight chain or branched chain alkyl which is optionally substituted with halo, oxo, hydroxy or alkoxy; and
(ii) C$_2$ to C$_{20}$ straight chain or branched chain alkenyl, alkynyl, or dialkenyl which is optionally substituted with halo, oxo, hydroxy or alkoxy;

or any one or two of G$^1$R$^2$, G$^2$R$^4$, G$^3$R$^5$, and G$^4$R$^7$ may together be a hydrogen atom or hydroxyl;

or a pharmaceutically acceptable salt thereof.

The compounds of the invention are acidic, and are typically isolated in a corresponding salt form. Accordingly, specifically contemplated within the scope of the invention are compounds of Formula II:

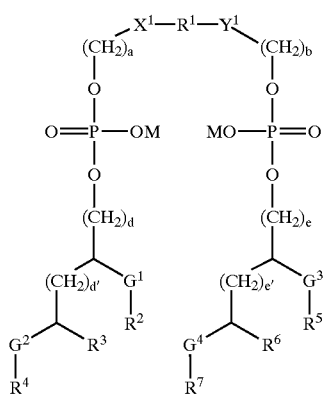

(II)

wherein M is a pharmaceutically acceptable cation, and all other variables are as defined above for Formula I. For divalent cations, the cation takes the place of two M variables in formula II above. Pharmaceutically acceptable cations are well known to those of ordinary skill in the art.

In some preferred embodiments of the invention, one or more of the following limitations is present: each of a and b is 2; each of X$^1$ and Y$^1$ is NH; each of d and e is 1 or 2; and each of d' and e' is 0, 1, or 2. In certain preferred embodiments, each of d and e is 1 and each of d' and e' is 0. In certain other preferred embodiments, each of and e is 1 and each of d' and e' is 1 or 2.

In some preferred embodiments, R$^1$ is —C(O)— or —C(O)—C$_{1-14}$ alkylene-C(O)—, wherein the C$_{1-14}$ alkylene is optionally substituted with one or two substituents selected from the group consisting of hydroxy, C$_{1-6}$ alkoxy, C$_{1-6}$ alkylenedioxy, C$_{1-6}$ alkylamino, or (aryl)C$_{1-6}$ alkyl, wherein said aryl moiety of said (aryl)C$_{1-6}$ alkyl is optionally substituted with C$_{1-6}$ alkyl, C$_{1-6}$ alkoxy, C$_{1-6}$ alkylamino, (C$_{1-6}$ alkoxy)C$_{1-6}$ alkylamino, (C$_{1-6}$ alkylamino)C$_{1-6}$ alkoxy, —O—C$_{1-6}$ alkylene-NH—C$_{1-6}$alkylene-O—C$_{1-6}$ alkyl, —O—C$_{1-6}$ alkylene-NH—C(O)—C$_{1-6}$ alkylene-C(O)OH, or —O—C$_{1-6}$ alkylene-NH—C(O)—C$_{1-6}$ alkylene-C(O)—C$_{1-6}$ alkyl.

In some preferred embodiments, G$^1$, G$^2$, G$^3$, and G$^4$ are each independently selected from the group consisting of —NH—C(O)— and —O—C(O)—.

In some preferred embodiments, at least two of R$^2$–R$^7$, R$^9$, and R$^{10}$ are C$_{6-20}$ straight or branched chain alkyl, alkenyl, alkynyl, or dialkenyl, any of which groups may be optionally substituted with one or two substituents selected from the group consisting of halo, oxo, hydroxy and alkoxy. In certain preferred embodiments, at least two of R$^2$–R$^7$, R$^9$, and R$^{10}$ are C$_{8-15}$ straight or branched chain alkyl, alkenyl, alkynyl, or dialkenyl, any of which groups may be optionally substituted with one or two substituents selected from the group consisting of halo, oxo, hydroxy and alkoxy.

In some preferred embodiments, at least four of R$^2$–R$^7$, R$^9$, and R$^{10}$ are C$_{6-20}$ straight or branched chain alkyl, alkenyl, alkynyl, or dialkenyl, any of which groups may be optionally substituted with one or two substituents selected from the group consisting of halo, oxo, hydroxy and alkoxy. In certain preferred embodiments, at least four of R$^2$–R$^7$, R$^9$, and R$^{10}$ are C$_{8-15}$ straight or branched chain alkyl, alkenyl, alkynyl, or dialkenyl, any of which groups may be optionally substituted with one or two substituents selected from the group consisting of halo, oxo, hydroxy and alkoxy.

In some preferred embodiments, at least six of R$^2$–R$^7$, R$^9$, and R$^{10}$ are C$_{6-20}$ straight or branched chain alkyl, alkenyl, alkynyl, or dialkenyl, any of which groups may be optionally substituted with one or two substituents selected from the group consisting of halo, oxo, hydroxy and alkoxy. In certain preferred embodiments, at least six of R$^2$–R$^7$, R$^9$, and R$^{10}$ are C$_{8-15}$ straight or branched chain alkyl, alkenyl, alkynyl, or dialkenyl, any of which groups may be optionally substituted with one or two substituents selected from the group consisting of halo, oxo, hydroxy and alkoxy.

Synthetic Methods

Type 1 Compounds

Type 1 compounds of Formula I, wherein d and e are each 1 and d' and e' are each 0, are preferably synthesized according to the synthetic route depicted in Scheme 1. Thus, the aldehyde III, which is obtained from L-serine by literature procedures, is treated with an organometallic reagent such as a Grignard reagent to afford the alcohol IV. Acid treatment of IV, e.g., treatment with anhydrous HCl gas in methanol, affords the corresponding amino diol, which is selectively acylated on nitrogen to afford V. Protection of the primary alcohol, followed by acylation of the secondary alcohol then affords the compound VI. Deprotection of the primary alcohol and reaction with the phosphorylating reagent, prepared as described in the Experimental Section, then affords VII. Treatment with triethylsilane and trifluoroacetic acid effects removal of the Boc protecting group, and treatment with phosgene then affords the symmetrical dimer VIII. Finally, treatment with phenylsilane and tetrakis(triphenylphosphine)palladium(0) effects removal of the allyl protecting group to afford IX.

Scheme 1
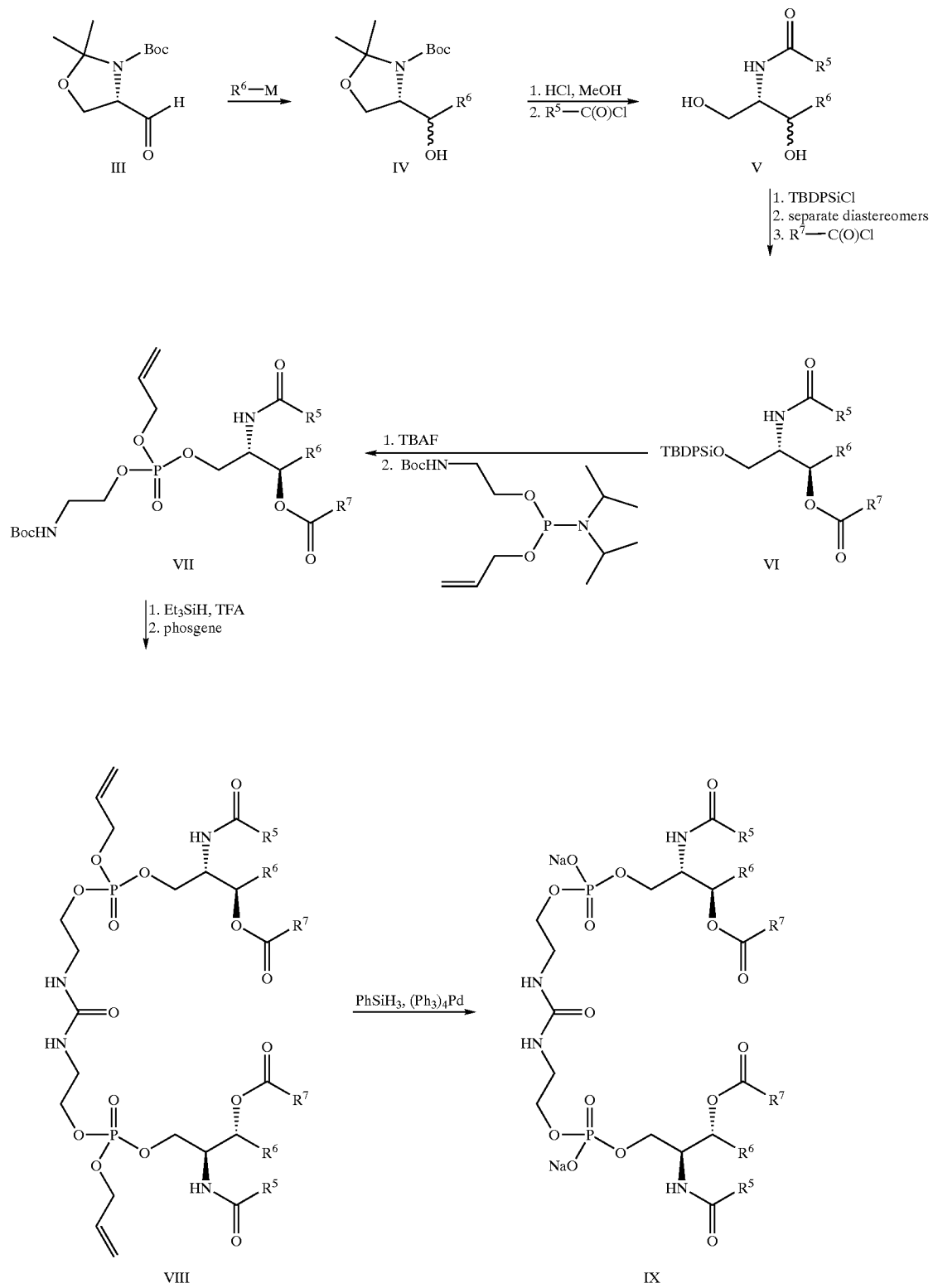

Alternatively, intermediate IV may be prepared as a single diastereomer, preferably according to the synthetic route outlined in Scheme 2.

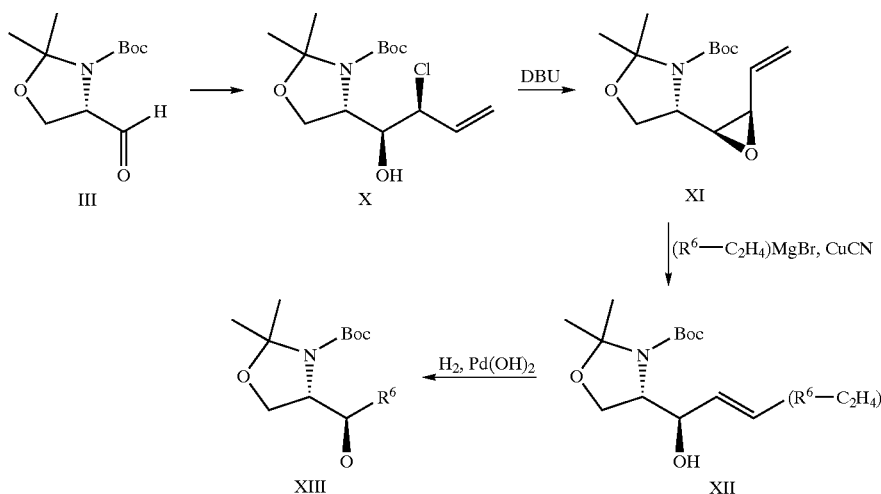

Thus, aldehyde III is treated with allyl chloride and (+)-B-methoxydiisopino-campheylborane to afford X as a single diastereomer. Epoxide ring closure is effected by treatment with DBU, followed by $S_N2'$ ring opening with an organocuprate reagent to afford XII. Hydrogenation then affords the alcohol XIII, which is converted to IX as described above for IV.

Type 1 compounds of Formula I, wherein d and e are each 1 and d' and e' are each 1, are preferably prepared by procedures analogous to those outlined in Schemes 1 and 2 above, but starting with aldehyde XIV in place of III. Aldehyde XIV is preferably prepared by homologation of III, as outlined in Scheme 3. Thus, aldehyde III is treated with [2-(trimethylsilyl)ethoxymethyl]triphenylphosphonium chloride and n-butyllithium to afford the enol ether, which is treated with acetic acid to provide XIV.

Scheme 3

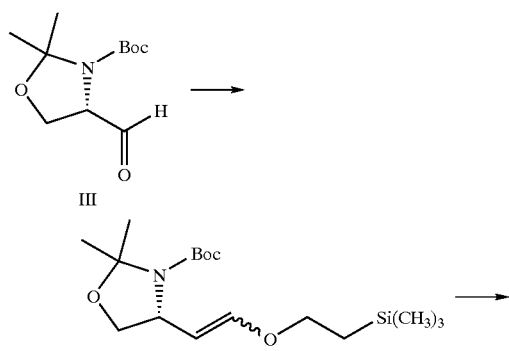

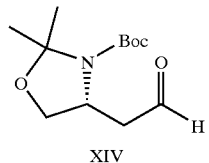

Type 1 compounds of Formula I with different values for d and e and/or d' and e' are preferably prepared by methods generally analogous to those described above, as further described in the examples. One of skill in the art will also easily recognize that the synthetic methods outlined above may be adapted to the synthesis of compounds of Formula I, wherein $G^3$ and/or $G^4$ are other than —O—C(O)— or —NH—C(O)—, by performing alternative standard functional group transformations in place of the acylation steps described above.

Type 2 Compounds

Type 2 compounds of Formula I are preferably synthesized by methods analogous to those described for the synthesis of Type 1 compounds, up to the point just after cleavage of the protecting group from the primary amine group of the phosphate ester compound. At this point, the phosphate ester compound is treated with a monoprotected difunctionalized compound, such as a dicarboxylic acid. The resultant compound is deprotected and allowed to react with a second phosphate ester compound. Final phosphate deprotection is then accomplished as described for the Type 1 compounds.

An alternative method for the synthesis of the Type 2 compounds is to form the isocyanate intermediate of the deprotected primary amine group of the phosphate ester compound. The isocyanate intermediate is then treated with a second deprotected primary amine of a phosphate ester compound followed by deprotection as described for the Type 1 compounds.

Adjuvant and Vaccine Formulations and Administration

In a second aspect, the invention provides immunological compositions comprising a compound of formula I:

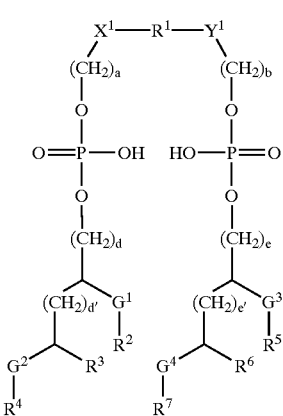

(I)

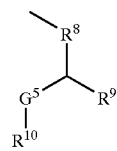

(c)

wherein

R$^1$ is selected from the group consisting of
(a) —C(O)—,
(b) —C(O)—C$_{1-14}$ alkylene-C(O)— or —C(O)—C$_{1-14}$ alkenylene-C(O)—, wherein the C$_{1-14}$ alkylene or C$_{1-14}$ alkenylene is optionally substituted with hydroxy, C$_{1-6}$ alkoxy, C$_{1-6}$ alkylenedioxy, carboxy, C$_{1-6}$ alkoxycarbonyl, C$_{1-6}$ carbamoyl, C$_{1-6}$ acylamino, C$_{1-6}$ alkylamino, or (aryl)C$_{1-6}$ alkyl, wherein said aryl moiety of said (aryl)C$_{1-6}$ alkyl is optionally substituted with C$_{1-6}$ alkyl, C$_{1-6}$ alkoxy, C$_1$ alkylamino, (C$_{1-6}$ alkoxy)C$_{1-6}$ alkylamino, (C$_{1-6}$ alkylamino)C$_{1-6}$ alkoxy, —O—C$_{1-6}$ alkylene-NH—C$_{1-6}$alkylene-O—C$_{1-6}$ alkyl, —O—C$_{1-6}$ alkylene-NH—C(O)—C$_{1-6}$ alkylene-C(O)OH, or —O—C$_{1-6}$ alkylene-NH—C(O)—C$_{1-6}$ alkylene-C(O)—C$_{1-6}$ alkyl;
(c) C$_2$ to C$_{15}$ straight or branched chain alkyl optionally substituted with hydroxy or alkoxy; and
(d) —C(O)—C$_{6-12}$ arylene-C(O)— wherein said arylene is optionally substituted with C$_{1-6}$ alkyl, hydroxy, C$_{1-6}$ alkoxy, halogen, nitro or amino;

a and b are independently an integer from 0 to about 4;
d and e are independently an integer from 1 to about 6;
d' and e' are independently an integer from 0 to about 2;
X$^1$ and Y$^1$ are independently selected from the group consisting of a null, oxygen, —NH—, —N(C(O)C$_{1-4}$ alkyl)-, and —N(C$_{1-4}$ alkyl)-,
G$^1$, G$^2$, G$^3$, and G$^4$ are independently selected from the group consisting of oxygen, methylene, —NH—, —N(C$_{1-4}$ alkyl)-, —N[C(O)—C$_{1-4}$ alkyl]-, —NH—C(O)—, —NH—SO$_2$—, —C(O)—O—, —C(O)—NH—, —O—C(O)—, —O—C(O)—NH—, —O—C(O)—O—, —NH—C(O)—NH—, —C(O)NH—, C(O)N(C$_{1-4}$ alkyl), and —S(O)$_n$—, where n is 0, 1, or 2;
R$^2$, R$^3$, R$^4$, R$^5$, R$^6$, and R$^7$ are independently selected from the group consisting of:
(a) C$_1$ to C$_{20}$ straight chain or branched chain alkyl which is optionally substituted with halo, oxo, hydroxy or alkoxy;
(b) C$_2$ to C$_{20}$ straight chain or branched chain alkenyl, alkynyl, or dialkenyl which is optionally substituted with halo, oxo, hydroxy or alkoxy; and wherein
R$^8$ is C$_{1-6}$ straight or branched chain alkyl or C$_{2-6}$ straight or branched chain alkenyl, alkynyl, or dialkenyl;
G$^5$ is selected from the group consisting of oxygen, methylene, arylene, —NH—, —N(C$_{1-4}$ alkyl)-, —N(C(O)—C$_{1-4}$ alkyl)-, —NH—C(O)—, —NH—SO$_2$—, —C(O)—O—, —C(O)—NH—, —O—C(O)—, —O—C(O)—NH—, —O—C(O)—O—, —NH—C(O)—NH—, and —S(O)$_n$—, where n is 0, 1, or 2;
R$^9$ and R$^{10}$ are independently selected from the group consisting of
(i) C$_1$ to C$_{20}$ straight chain or branched chain alkyl which is optionally substituted with halo, oxo, hydroxy or alkoxy; and
(ii) C$_2$ to C$_{20}$ straight chain or branched chain alkenyl, alkynyl, or dialkenyl which is optionally substituted with halo, oxo, hydroxy or alkoxy;
or any one or two of G$^1$R$^2$, G$^2$R$^4$, G$^3$R$^5$, and G$^4$R$^7$ may together be a hydrogen atom or hydroxyl;
or a pharmaceutically acceptable salt thereof; and
a pharmaceutically acceptable carrier, diluent, or excipient.

Preferred embodiments according to this aspect of the invention are as described above for the first aspect.

The invention is also directed to novel immunological compositions comprising a compound of formula I, as described above; an antigen; and a pharmaceutically acceptable carrier, diluent, or excipient.

The immunological composition may utilize any suitable antigen or vaccine component in combination with an adjuvant compound of the invention. As a further example, such immunological compositions may suitably comprise an attenuated organism, or a component of an organism, such as a carbohydrate, protein, or peptide, or a nucleic acid encoding such component.

Typically, an antigen is employed in mixture with the adjuvant compounds of the invention. In certain other embodiments, it may be useful in some applications to employ an antigen covalently linked to an amino, carboxyl, hydroxyl and/or phosphate moiety of the adjuvant compounds of the invention. The specific formulation of therapeutically effective compositions of the present invention may thus be carried out in any suitable manner which will render the adjuvant bioavailable, safe and effective in the subject to whom the formulation is administered.

Such immunological compositions may, for example, comprise at least one antigenic agent used as a vaccine for any disease or condition amenable to vaccination, including, but not limited to:

(A) human and animal infectious diseases, including those caused by bacteria, viruses, parasites (e.g., mycoplasmas, fungi, protozoa) and prions;
(B) diseases or pathologies in which an immune response against an autologous molecule may be beneficial, such as, but not limited to, Alzheimer's disease, in which immunization to amyloid β42 may be beneficial; gastric reflux disease, in which immunization to gastrin may be beneficial; cancer, including, without limitation, melanoma, prostate, and colon cancer, in which immunization to cancer antigens may be beneficial; and autoimmune disorders, including, without limitation, diabetes, in which immunization to insulin may decrease or redirect inflammatory responses against insulin-producing cells; and (C) non-pathological situations in which an immune response may bring about a desired change in function or physiology, such as, but not limited to, the contraceptive effect induced by immunization to hCG.

As further examples, the immunological compositions of the invention may comprise antigens or vaccine components which are pharmacologically active for disease states and conditions such as smallpox, yellow fever, distemper, cholera, fowl pox, scarlet fever, diphtheria, tetanus, whooping cough, influenza, rabies, mumps, HIV, chicken pox, rubella, measles, foot and mouth disease, and poliomyelitis.

In the resulting vaccine formulation, comprising (i) an antigen, and (ii) at least one adjuvant compound of the invention, the antigen and adjuvant compound are each present in an amount effective to elicit an immune response when the formulation is administered to a host animal, embryo, or ovum vaccinated therewith.

In further embodiments, the compounds of the invention may be covalently bonded to vaccine antigens, for example through an amino, thiol, carboxyl, hydroxyl or phosphate moiety. Methods of linking the adjuvant compositions of the invention to vaccine antigens are understood by persons of ordinary skill in the art in view of this disclosure. The adjuvant compositions may be linked to vaccines by any of the methods described in P. Hoffman et al., *Biol. Chem. Hoppe-Sayler*, 1989, 370:575–582; K.-H. Wiesmuller et al., *Vaccine*, 1989, 7:29–33; K.-H Wiesmuller et al., *Int. J. Peptide Protein Res.*, 1992, 40:255–260; J.-P. Defourt et al., *Proc. Natl. Acad. Sci.* 1992, 89:3879–3883; T. Tohokuni et al., *J. Am. Chem. Soc.*, 1994, 116:395–396; F. Reichel, *Chem. Commun.*, 1997, 2087–2088; H. Kamitakahara, *Angew. Chem. Int. Ed.* 1998, 37:1524–1528; W. Dullenkopf et al., *Chem. Eur. J.*, 1999, 5:2432–2438; all of which are hereby incorporated by reference.

The resulting vaccine formulations, including (i) an antigen, and (ii) an adjuvant compound, are usefully employed to induce an immunological response in an animal, by administering to such animal the vaccine formulation, in an amount sufficient to produce an antibody response in such animal.

The modes of administration may comprise the use of any suitable means and/or methods for delivering the adjuvant, adjuvant-containing vaccine, or adjuvant and/or antigen to one or more corporeal loci of the host animal where the adjuvant and associated antigens are immumostimulatorily effective. Delivery modes may include, without limitation, parenteral administration methods, such as subcutaneous (SC) injection, transcutaneous, intranasal (IN), ophthalmic, transdermal, intramuscular (IM), intradermal (ID), intraperitoneal (IP), intravaginal, pulmonary, and rectal administration, as well as non-parenteral, e.g., oral, administration.

The dose rate and suitable dosage forms for the adjuvant and vaccine compositions of the present invention may be readily determined by those of ordinary skill in the art without undue experimentation, by use of conventional antibody titer determination techniques and conventional bioefficacy/biocompatibility protocols, and depending on the particular antigen or therapeutic agent employed with the adjuvant, the desired therapeutic effect, and the desired time span of bioactivity.

The adjuvant of the present invention may be usefully administered to the host animal with any other suitable pharmacologically or physiologically active agents, e.g., antigenic and/or other biologically active substances.

Formulations of the invention can include additional components such as saline, oil, squalene, oil-water dispersions, liposomes, and other adjuvants such as QS-21, muramyl peptides, Freund's incomplete adjuvant, and the like.

The present invention will now be illustrated by the following examples, which are not intended to be limiting in any way.

SYNTHETIC EXAMPLES

All reaction products gave satisfactory NMR spectra and silica gel thin layer chromatography (TLC). All chromatographies were preformed on silica gel and the elution monitored by TLC. All completed reactions were determined by tlc analysis. All reactions were run under nitrogen at room temperature unless otherwise specified. All reaction solvents were anhydrous unless otherwise noted. The usual work-up includes aqueous washings, organic solvent extraction, drying over anhydrous sodium sulfate and removal of the solvent under reduced pressure.

Example 1

Preparation of ER-805028

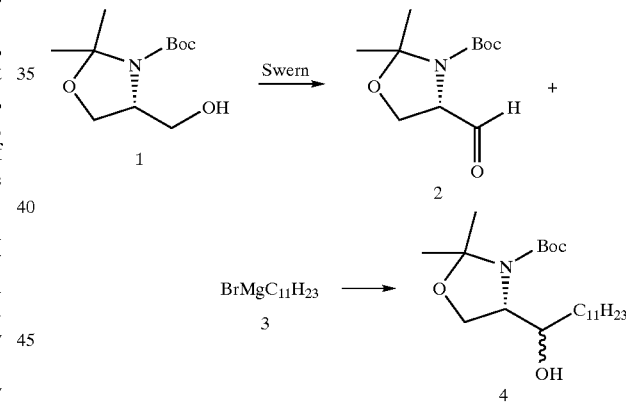

To a stirred solution of oxalyl chloride (0.65 mL) in methylene chloride (50 mL) at −78° C. was added DMSO (1.1 mL) dropwise followed by stirring for 30 minutes. Chiral alcohol 1 (908 mg—from L-serine via known literature methods) in methylene chloride (5 mL) was added dropwise and then allowed to stir between −40° C. and −60° C. for one hour after which time triethylamine (3.48 mL) was added dropwise and the reaction was allowed to warm to room temperature over a one hour period. The crude aldehyde 2 obtained after work-up was dissolved in THF (20 mL) and added dropwise at −20° C. to the previously generated undecanyl magnesium bromide 3 (generated from magnesium turnings (132 mg) and undecanyl bromide (1.054 g) in THF (4 mL) at 50° C. for 3 hours with a crystal of iodine). The Grignard reaction was warmed to room temperature and stirred for 2 hours. The usual work-up and silica gel chromatography purification provided 4 (1.42 g).

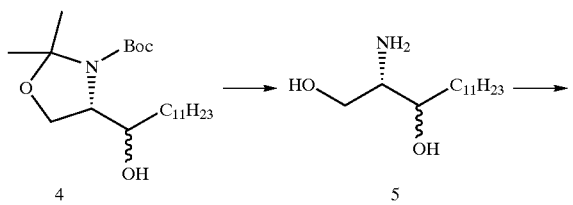

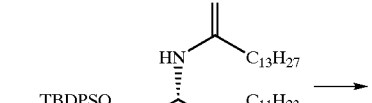

To a stirred solution of 4 (1.42 g) in methanol (100 mL) was added anhydrous HCl gas at 0° C. for 10 minutes after which time the reaction mixture was warmed to room temperature. After concentration of the mixture to dryness, the crude product was rendered basic with 1 N sodium hydroxide and extracted with ethyl acetate to provide crude 5 (509 mg). 5 (509 mg) was dissolved in THF (4 mL) and saturated sodium bicarbonate was added (8 mL) followed by the dropwise addition of tetradecanoyl chloride (0.57 mL) at 0° C. followed by vigorous stirring for 1 hour. Normal work-up and silica gel purification provided 6 (466 mg).

To a stirred solution of 6 (466 mg) in methylene chloride (10 mL) was added imidazole (105 mg) followed by tert-butyldiphenylsilyl chloride (302 mg). After stirring at room temperature for 48 hours, normal work followed by silica gel purification provided isomer 7 (293 mg) separated from isomer 8 (235 mg). Note: The stereochemistry of the two products were determined by direct comparison ($^1$H-NMR and tlc) to the chiral isomer generated from 17 (preparation described below).

To a stirred solution of 8 (154 mg) in methylene chloride (0.5 mL) was added lauric acid (59 mg), 1-[3-(dimethylamino)propyl]-3-ethylcarbodiimide hydrochloride (EDC, 70 mg) and N,N-4-dimethylaminopyridine (DMAP, 3 mg). After stirring for 16 hours, aqueous work-up, and silica gel purification provided 9 (197 mg).

To a stirred solution of 9 (197 mg) in THF (1.0 mL) was added acetic acid (20 mg) followed by tetra-n-butylammonium fluoride (88 mg) at room temperature. After stirring for 16 hours the reaction mixture was quenched and purified using silica gel chromatography to provide 10 (134 mg).

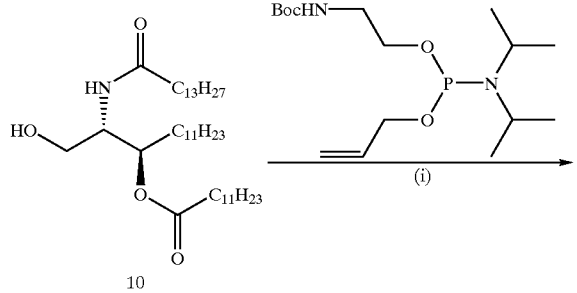

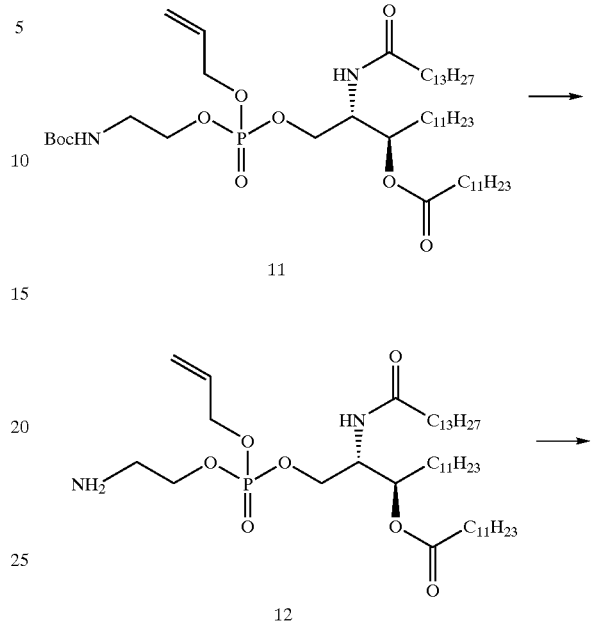

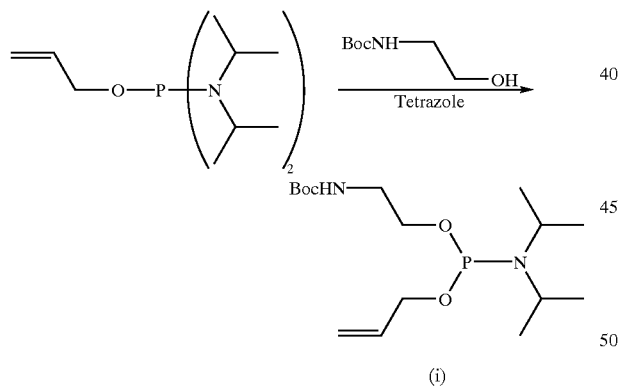

To a stirred solution of 10 (134 mg) in methylene chloride (0.8 mL) was added tetrazole (45 mg) followed by the phosphorylating reagent (i) (106 mg) at 0° C. After stirring for 1 hour, the reaction mixture was poured onto a stirred suspension containing oxone (204 mg) in THF (1 mL) and water (1 mL). After an additional 1 hour stirring at 0° C. the mixture was worked up and purified over silica gel to give 11 (140 mg).

To make the phosphorylating reagent (i), to a solution of distilled diisopropylamine (9.0 mL) in methylene chloride was added tetrazole (4.51 g) at room temperature, followed by stirring for 1.5 hours. Allyl phosphorodiamidite (20.5 mL) was added dropwise at a 6.5 mL/hour rate, followed by stirring for an additional 3 hours. N-Boc-2-aminoethanol (10.36 g) in methylene chloride (50 mL) was added to the above reaction mixture dropwise at an 8.4 mL/hour rate, followed by stirring for an additional 18 hours. The white suspension was filtered through Celite 545 with two 20-mL washings with methylene chloride. The filtrate was concentrated, followed by the suspension and filtering of the residue with hexanes (200 mL). The resulting hexanes filtrate was concentrated to dryness and azeotroped with two 10-mL portions of toluene to provide the crude product (i) (21.54 g) as an oil.

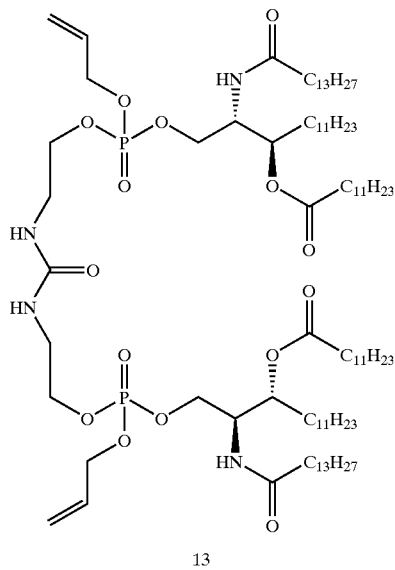

To a stirred solution of 11 (58 mg) in methylene chloride (0.16 mL) was added triethylsilane (0.16 mL) followed by trifluoroacetic acid (1.0 mL) at room temperature. After stirring for 2 hours the solvents were concentrated and azeotroped to dry using toluene. The crude amine 12 was dissolved in methylene chloride (0.6 mL) with saturated sodium bicarbonate (0.6 mL) followed by the dropwise addition of phosgene (0.018 mL of a 1.93 M solution in toluene) at 0° C. After stirring at room temperature for 2 hours the reaction was worked-up and purified by silica gel in the normal fashion to provide 13 (55 mg).

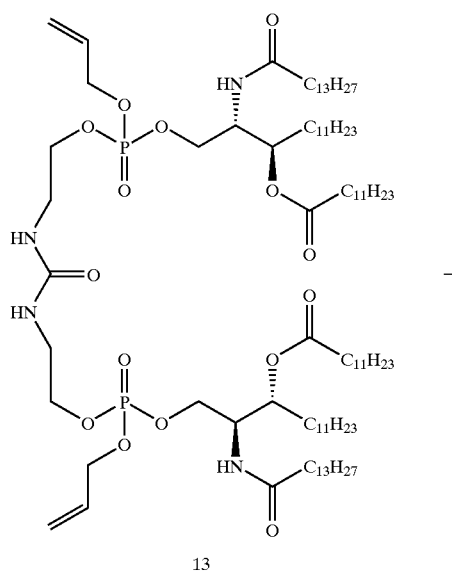

13

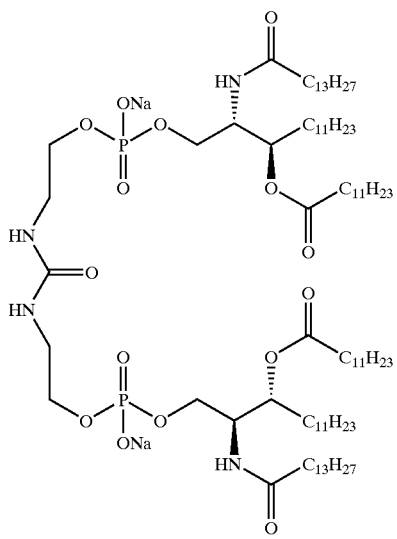

ER-805028

To a stirred solution of 13 (55 mg) in degassed chloroform (3 mL) was added phenylsilane (56 mg) and tetrakis (triphenylphosphine)palladium(0) (54 mg) at 0° C. After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805028 (2.2 mg).

Example 2

Preparation of 8 by a Chiral-specific Method

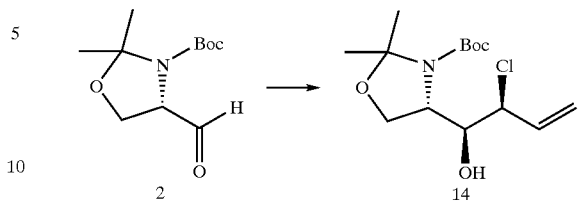

To a stirred solution of dicyclohexylamine (634 mg) in THF (5 mL) was added n-butyllithium (1.6 M—2.19 mL) at 0° C. After stirring at room temperature of 1 hour, the reaction mixture was added dropwise to a stirred solution of allyl chloride (270 mg) and (+)-B-methoxydiisopinocampheylborane (824 mg) in ethyl ether (10 mL) cooled to −95° C. The mixture was stirred at −95° C. for 1 hour after which time boron trifluoride etherate (827 mg) was added. After 20 minutes of additional stirring at −95° C. aldehyde 2 (570 mg) in ethyl ether (2 mL) was added. The final reaction mixture was allowed to warm slowly to room temperature, stir for 12 hour and was quenched oxidatively using hydrogen peroxide (9 mL) and sodium bicarbonate (0.9 g) in a solution of methanol (4.5 mL) and saturated sodium bicarbonate (2.5 mL). 14 (1.30 g) was obtained after the usual work-up and silica gel chromatography.

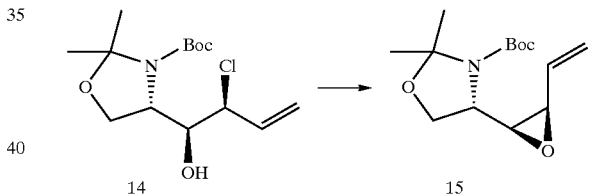

To a stirred solution of 14 (1.3 g) was added 1,8-diazabicyclo[5.4.0]undec-7-ene (1.77 g) in methylene chloride (46 mL) at 0° C. After stirring the reaction mixture at room temperature for 72 hours, a normal work-up with silica gel purification provided 15 (300 mg).

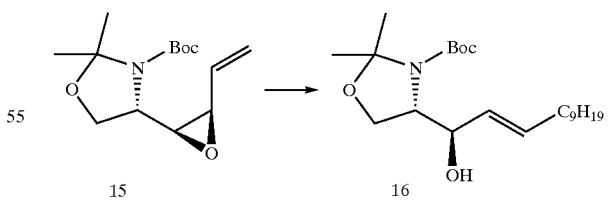

To a stirred suspension of copper (I) cyanide (105 mg) in THF (30 mL) was added octylmagnesium bromide (2.0 M—0.74 mL) dropwise at −78° C. followed by stirring for 15 minutes and room temperature for 2 hours. After returning the reaction mixture to −78° C., 15 (198 mg) in THF (2 mL) was added dropwise, allowed to stir at −78° C. for 1 hour followed by stirring at 0° C. for 1 hour. Normal work-up followed by silica gel purification provided 16 (168 mg).

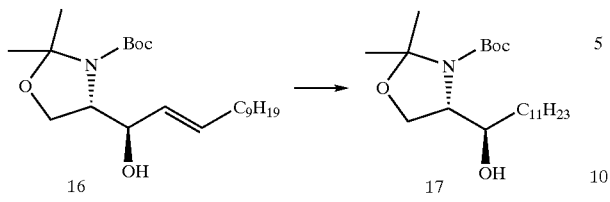

To a stirred solution of 16 (30 mg) in ethyl acetate (50 mL) was added 10% palladium/carbon (10 mg) after which time the mixture was placed under a hydrogen atmosphere (60 psi) and shaken at room temperature for 16 hours. Filtration followed by concentration and silica gel chromatography provided 17 (30 mg).

The stereochemistry of 7 and 8 was definitively established after converting 17 to 8 using the steps outlined above from compound 4.

Example 3

Preparation of ER-804874

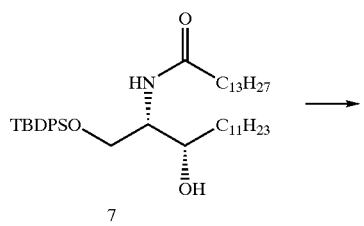

To a stirred solution of 7 (196 mg) in methylene chloride (0.5 mL) was added lauric acid (73.5 mg), EDC (87 mg), followed by DMAP (3.5 mg). 18 (242 mg) was obtained after stirring at room temperature for 16 hours, work-up and silica gel purification.

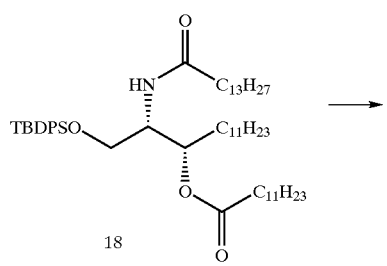

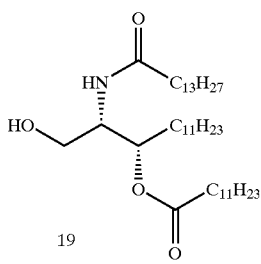

To a stirred solution of 18 (242 mg) in THF (1.0 mL) was added acetic acid (25 mg) followed by tetra-n-butylammonium fluoride (109 mg) at room temperature. After stirring for 16 hours the reaction mixture was quenched and purified using silica gel chromatography to provide 19 (144 mg).

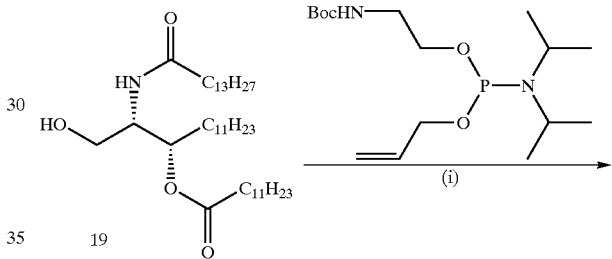

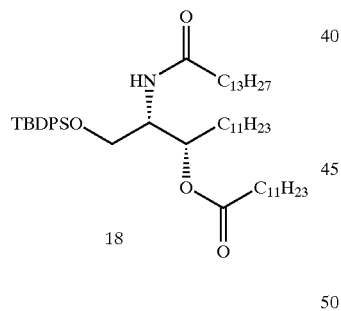

To a stirred solution of 19 (108 mg) in methylene chloride (0.8 mL) was added tetrazole (36 mg) followed by the phosphorylating reagent (36 mg) at 0° C. After stirring for 1 hour, the reaction mixture was poured onto a stirred suspension containing oxone (204 mg) in THF (1 mL) and water (1 mL). After an additional 1 hour stirring at 0° C. the mixture was worked-up and purified over silica gel to give 20 (128 mg).

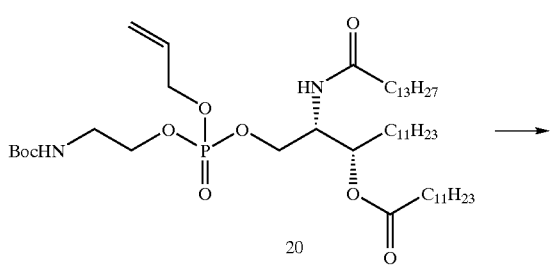

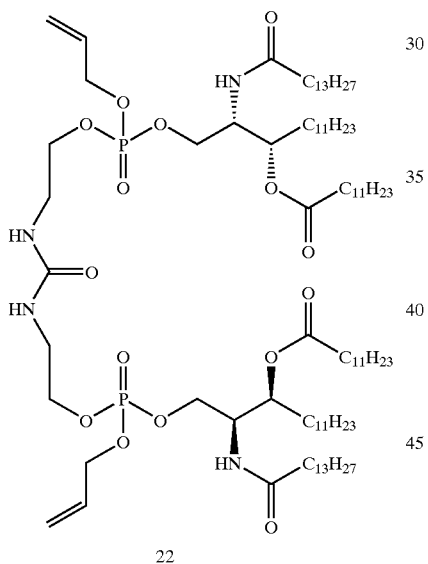

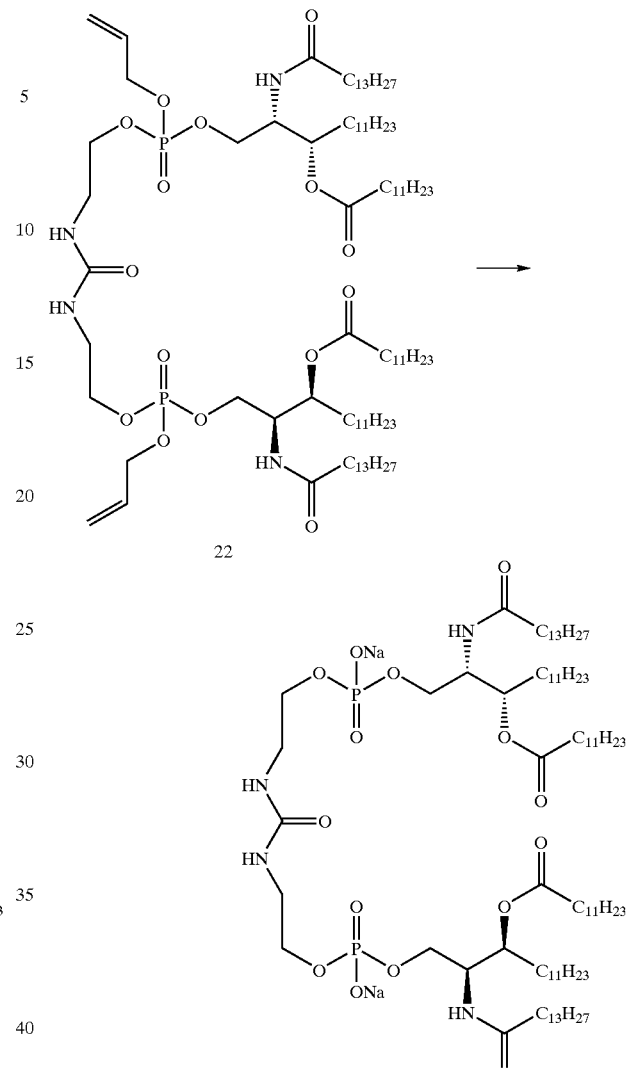

To a stirred solution of 20 (40 mg) in methylene chloride (0.16 mL) was added triethylsilane (0.11 mL) followed by trifluoroacetic acid (1.0 mL) at room temperature. After stirring for 2 hours the solvents were concentrated and azeotroped to dry using toluene. The crude amine 21 was dissolved in methylene chloride (0.5 mL) with saturated sodium bicarbonate (0.5 mL) followed by the dropwise addition of phosgene (0.012 mL of a 1.93 M solution in toluene) at 0° C. After stirring at room temperature for 2 hours the reaction was worked-up and purified by silica gel in the normal fashion to provide 22 (31 mg).

To a stirred solution of 22 (31 mg) in degassed chloroform (2 mL) was added phenylsilane (12 μL) and tetrakis(triphenylphosphine)palladium(0) (32 mg) at 0° C. After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-804874 (6.0 mg).

Example 4
Preparation of ER-804666

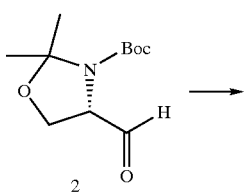

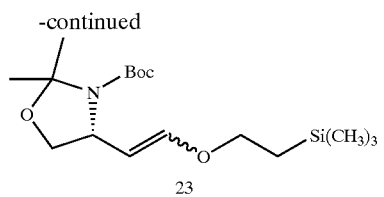

To a stirred suspension of [2-(trimethylsilyl)ethoxymethyl]triphenyl-phosphonium chloride (1.54 g) in THF (10 mL) was added n-butyl lithium (1.6 M—2.25 mL) at 0° C. followed by 2 (649 mg) in THF (5 mL) dropwise. 23 (371 mg) was obtained after stirring for an additional 1 hour at room temperature, work-up and silica gel purification.

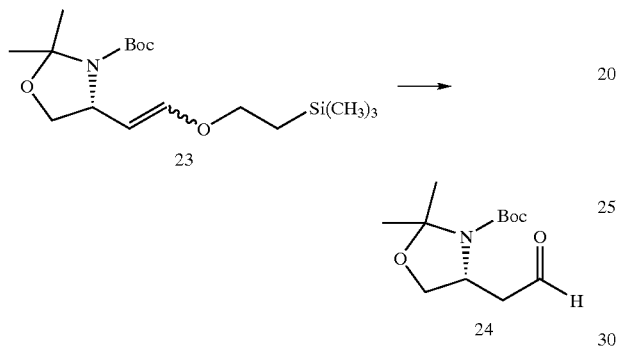

23 (400 mg) was dissolved in a mixture of acetic acid (5 mL) and water (1 mL) and stirred at room temperature for 4 hours. 24 (112 mg) was obtained by concentration and silica gel purification.

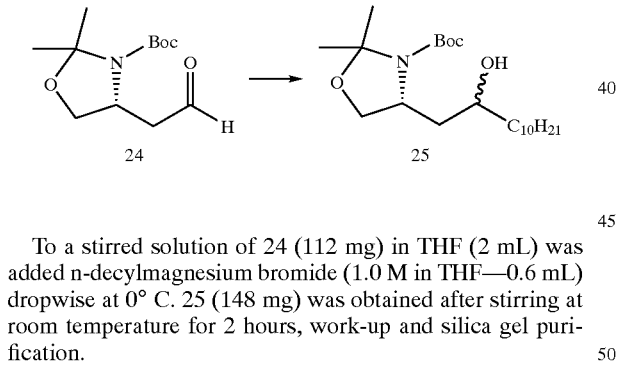

To a stirred solution of 24 (112 mg) in THF (2 mL) was added n-decylmagnesium bromide (1.0 M in THF—0.6 mL) dropwise at 0° C. 25 (148 mg) was obtained after stirring at room temperature for 2 hours, work-up and silica gel purification.

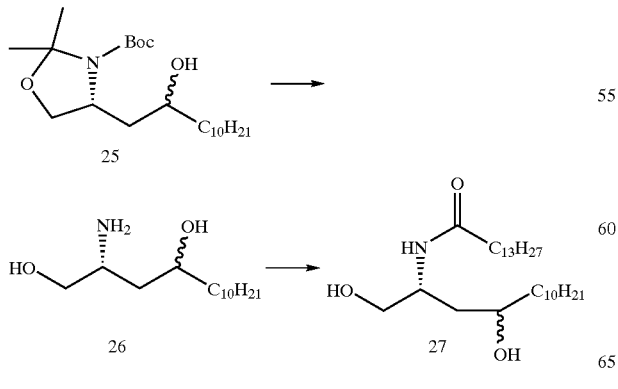

To stirred solution of 25 (148 mg) in methanol (10 mL) was added anhydrous hydrogen chloride gas for 15 minutes at 6° C. The mixture stirred at room temperature for 16 hours after which time concentration to dryness provided crude 26 (124 mg). 26 (124 mg) was dissolved in THF (1 mL) at 0° C. followed by saturated sodium bicarbonate (2 mL) and tetradecanoyl chloride (99 mg). 27 (69 mg) was obtained after stirring for 1 hour at room temperature followed by work-up and silica gel purification.

To a stirred solution of 27 (69 mg) in methylene chloride (10 mL) was added imidazole (15.4 mg) followed by tert-butyldiphenylsilyl chloride (39 μL). After stirring at room temperature for 48 hours, normal work-up followed by silica gel purification provided 28 (95 mg).

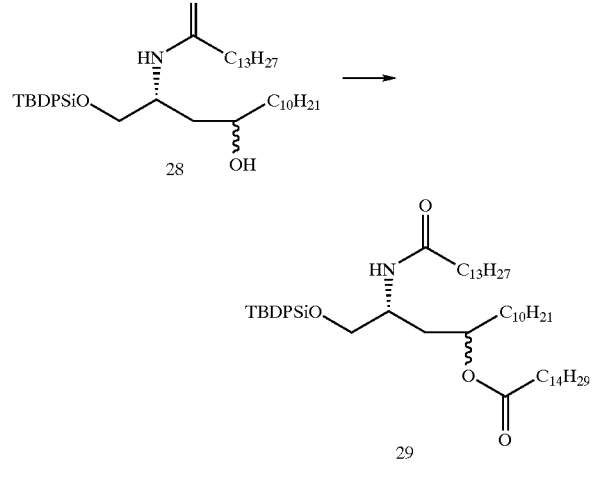

To a stirred solution of 28 (95 mg) in methylene chloride (0.5 mL) was added pentadecanoic acid (41 mg), EDC (40 mg) and DMAP (2 mg). After stirring for 16 hours, an aqueous work-up and silica gel purification provided 29 (121 mg).

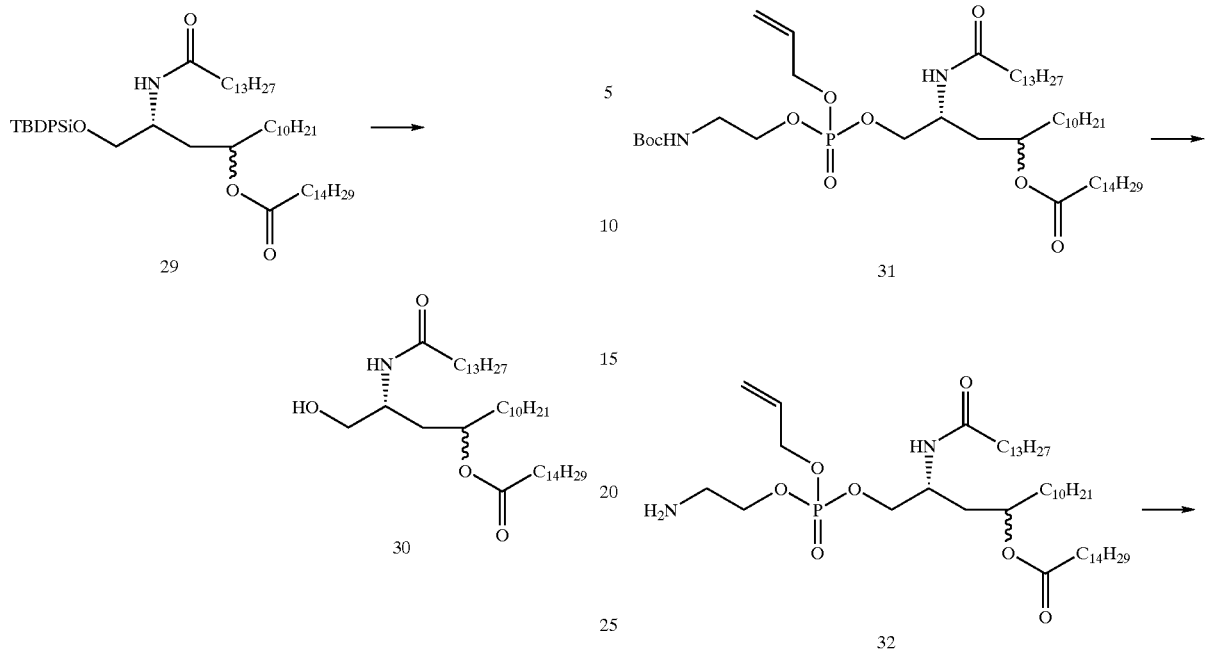

To a stirred solution of 29 (121 mg) in THF (1.0 mL) was added acetic acid (18 mg) followed by tetra-n-butylammonium fluoride (73 mg) at room temperature. After stirring for 16 hours the reaction mixture was quenched and purified using silica gel chromatography to provide 30 (81 mg).

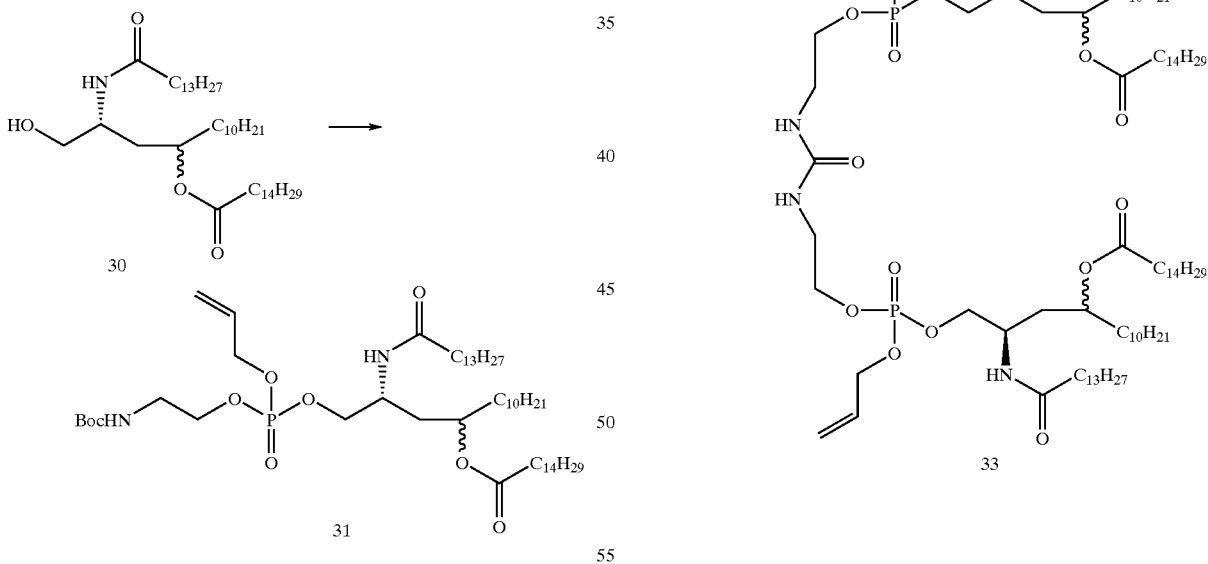

To a stirred solution of 30 (134 mg) in methylene chloride (0.6 mL) was added tetrazole (25 mg) followed by the phosphorylating reagent (60 mg) at 0° C. After stirring for 1 hour, the reaction mixture was poured onto a stirred suspension containing oxone (148 mg) in THF (1 mL) and water (1 mL). After an additional 1 hour stirring at 0° C. the mixture was worked up and purified over silica gel to give 31 (100 mg).

To a stirred solution of 31 (100 mg) in methylene chloride (0.10 mL) was added triethylsilane (0.10 mL) followed by trifluoroacetic acid (1.0 mL) at room temperature. After stirring for 2 hours the solvents were concentrated and azeotroped to dry using toluene. The crude amine 32 was dissolved in methylene chloride (0.5 mL) with saturated sodium bicarbonate (0.5 mL) followed by the dropwise addition of phosgene (0.013 mL of a 1.93 M solution in toluene) at 0° C. After stirring at room temperature for 2 hours, the reaction was worked-up and purified by silica gel in the normal fashion to provide 33 (46 mg).

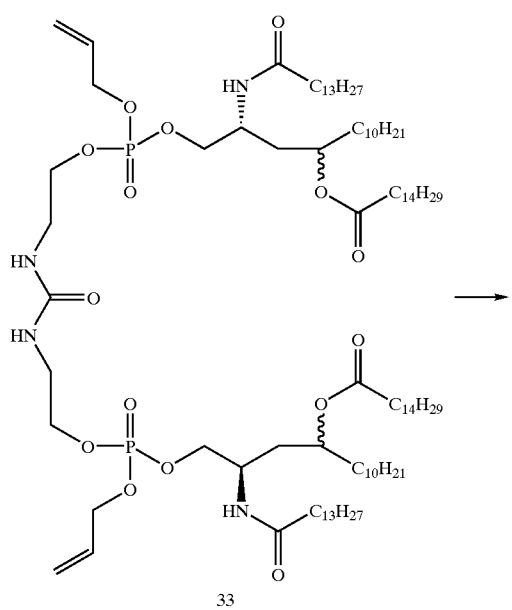

33

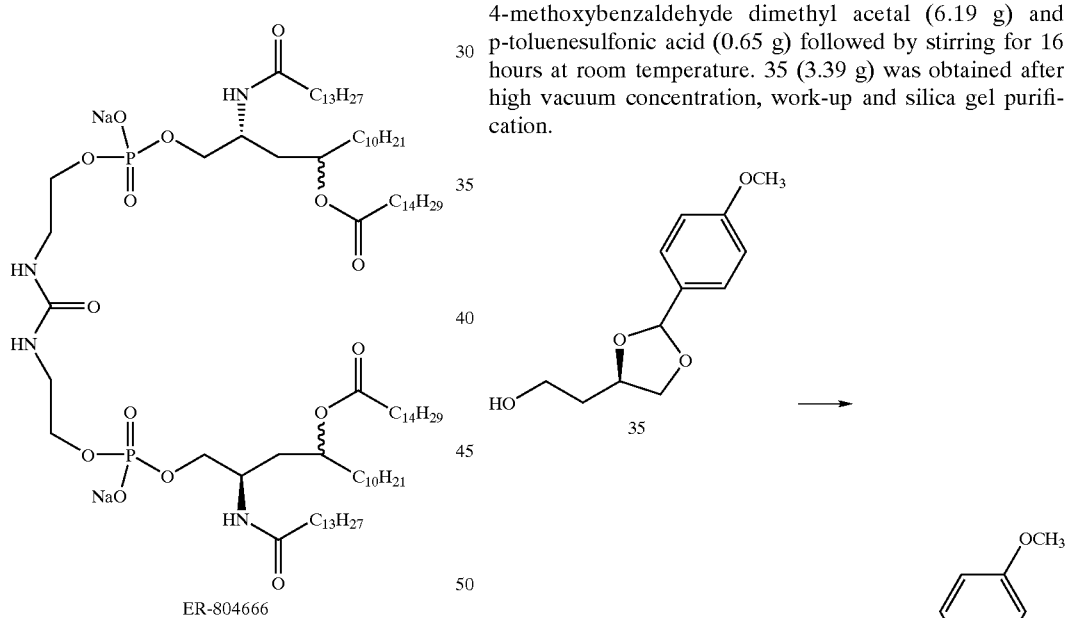

ER-804666

To a stirred solution of 33 (46 mg) in degassed chloroform (2 mL) was added phenylsilane (16 μL) and tetrakis(triphenylphosphine)palladium(0) (42 mg) at 0° C. After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-804666 (21.2 mg).

Example 5

Preparation of ER-805274

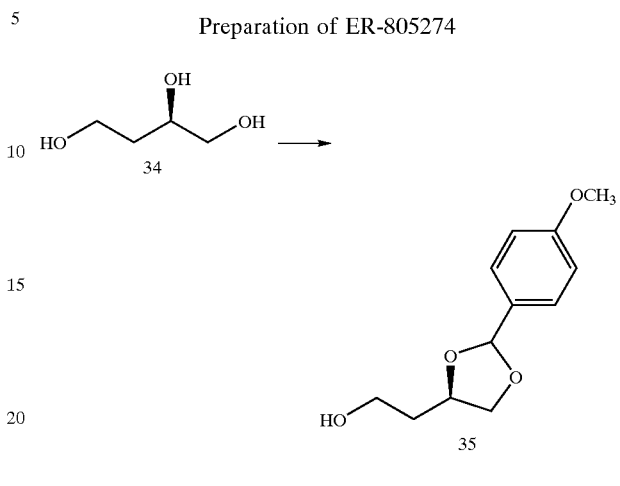

To a solution of commercially available, chiral 34 (2.69 g) in dimethylformamide (DMF—5 mL) was added 4-methoxybenzaldehyde dimethyl acetal (6.19 g) and p-toluenesulfonic acid (0.65 g) followed by stirring for 16 hours at room temperature. 35 (3.39 g) was obtained after high vacuum concentration, work-up and silica gel purification.

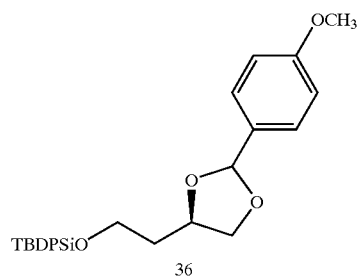

To a stirred solution of 35 (1.78 g) in methylene chloride (25 mL) was added imidazole (0.81 g) followed by tert-butyldiphenylsilyl chloride (2.41 g). After stirring at room temperature for 16 hours, normal work followed by silica gel purification provided 36 (3.55 g).

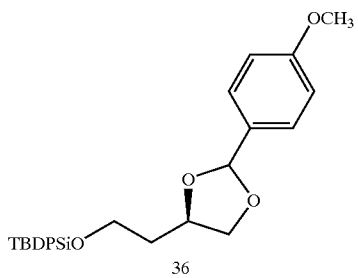

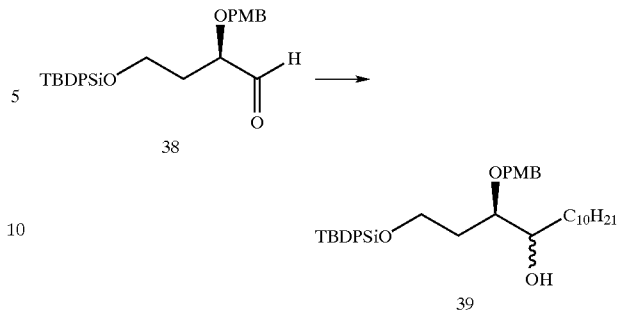

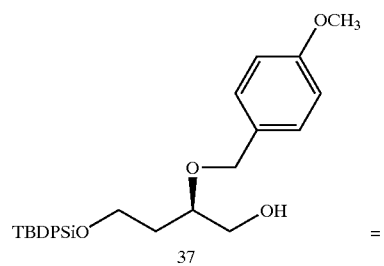

To a stirred solution of 38 (332 mg) in THF (5 mL) was added decanylmagnesium bromide (1.0 M in ethyl ether—1.44 mL) dropwise at 0° C. After stirring at room temperature for 16 hours, decanylmagnesium bromide (1.0 M in ethyl ether—0.5 mL) was added and the reaction was allowed to stir for an additional 1 hour. 39 (238 mg) was obtained after work-up and silica gel chromatography.

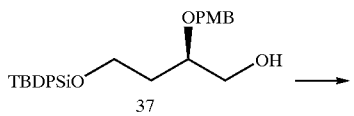

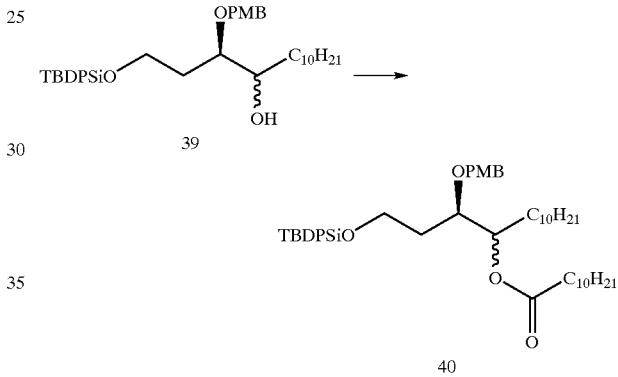

To a stirred solution of 36 (3.55 g) in methylene chloride (35 mL) was added dropwise diisobutylaluminum hydride (DIBAL—31 mL of a 1.0 M solution in hexanes) at −78° C. After stirring for an additional 2 hours at −78° C., the reaction mixture was quenched first with methanol:water followed by Rochelle's salts. 37 (725 mg) was obtained after work-up and silica gel chromatography.

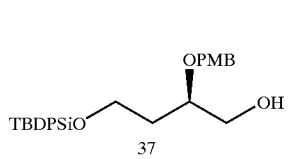

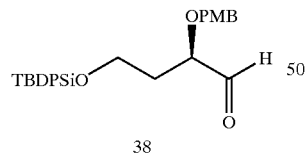

To a stirred solution of 39 (238 mg) in methylene chloride (4.0 mL) was added undecanoic acid (98 mg), EDC (125 mg) and DMAP (4.4 mg). After stirring for 16 hours, undecanoic acid (75 mg), EDC (94 mg) and DMAP (9 mg) were added and the reaction allowed to stir an additional 24 hours. An aqueous work-up followed by silica gel purification provided 40 (314 mg).

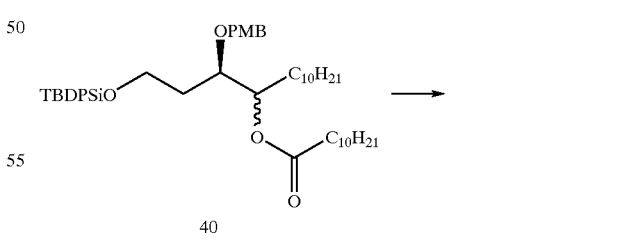

To a stirred solution of oxalyl chloride (0.11 mL) in methylene chloride (8 mL) at −78° C. was added DMSO (0.17 mL) dropwise followed stirring for 30 minutes. 37 (378 mg) in methylene chloride (2 mL) was added dropwise and then allowed to stir between −40° C. and −60° C. for one hour after which time triethylamine (0.57 mL) was added dropwise and the reaction was allowed to warm to room temperature over a one hour period. The crude aldehyde 38 (332 mg) obtained after work-up.

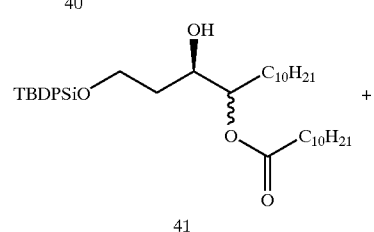

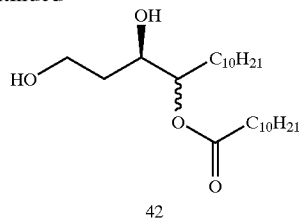

42

To a stirred solution of 40 (577 mg) in a 5:1 mixture of acetonitrile:water (7.5 mL) was added ceric ammonium nitrate (CAN—1.23 g) at 0° C. The reaction mixture was stirred at room temperature for 72 hours, worked-up and purified by silica gel chromatography to provide 41 (228 mg) and 42 (224 mg).

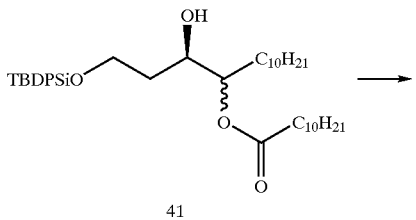

41

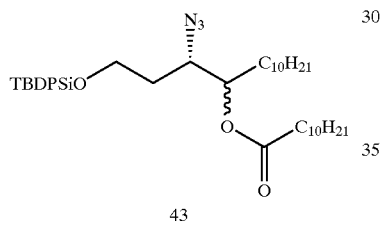

43

To a stirred solution of 41 (153 mg) in THF (2.3 mL) was added triphenylphosphine (246 mg), diphenylphosphoryl azide (259 mg), and diethyl azodicarboxylate (DEAD—164 mg). After stirring at room temperature for 2 hours, 43 (113 mg) was obtained after work-up and silica gel chromatography.

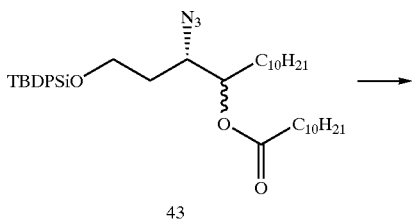

43

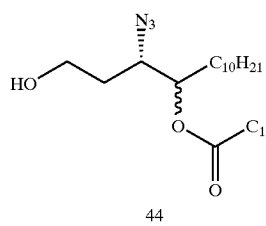

44

To a stirred solution of 43 (130 mg) in THF (1.0 mL) was added acetic acid (18 mg) followed by tetra-n-butylammonium fluoride (79 mg) at room temperature. After stirring for 48 hours the reaction mixture was quenched and purified using silica gel chromatography to provide 44 (75 mg).

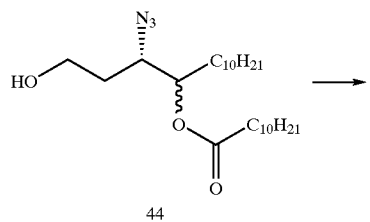

44

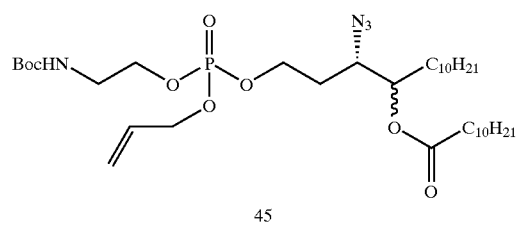

45

To a stirred solution of 44 (75 mg) in methylene chloride (0.6 mL) was added tetrazole (72 mg) followed by the phosphorylating reagent (170 mg) at 0° C. After stirring for 1 hour, the reaction mixture was poured onto a stirred suspension containing oxone (627 mg) in THF (1 mL) and water (1 mL). After an additional 1 hour stirring at 0° C. the mixture was worked up and purified over silica gel to give 45 (73 mg).

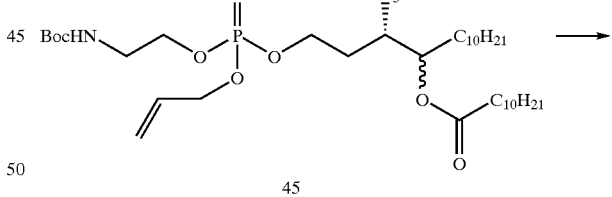

45

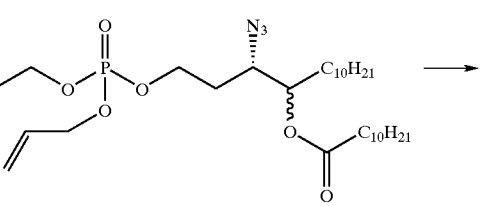

46

37

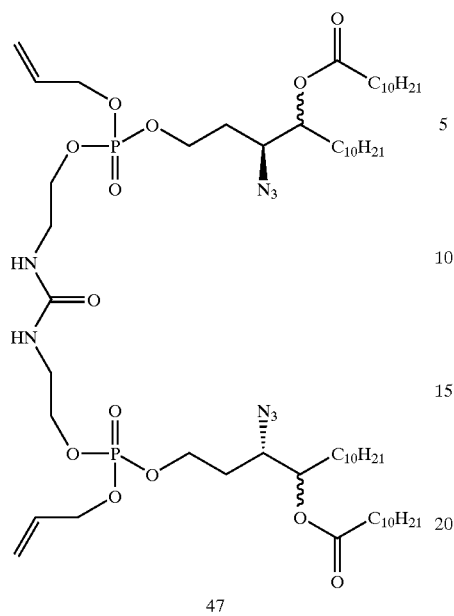

47

To a stirred solution of 45 (37 mg) in methylene chloride (0.10 mL) was added triethylsilane (0.09 mL) followed by trifluoroacetic acid (1.0 mL) at room temperature. After stirring for 2 hours the solvents were concentrated and azeotroped to dry using toluene. The crude amine 46 (33 mg) was dissolved in methylene chloride (0.5 mL) with saturated sodium bicarbonate (0.5 mL) followed by the dropwise addition of phosgene (0.014 mL of a 1.93 M solution in toluene) at 0° C. After stirring at room temperature for 2 hours the reaction was worked-up and purified by silica gel in the normal fashion to provide 47 (35 mg).

38

-continued

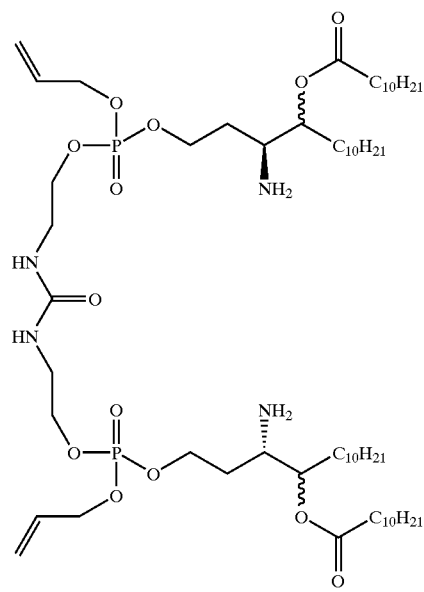

48

To a stirred solution of 47 (35 mg) was added a (PhS)$_3$SnH*Et$_3$N complex (0.5 M—0.34 mL) in methylene chloride at room temperature. The reaction mixture was stirred for 1 hour after which time it was purified by silica gel chromatography to provide crude 48 (29 mg) that was used immediately in the next step.

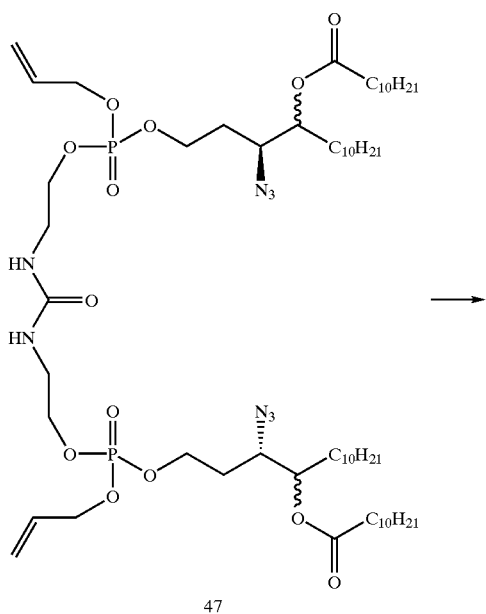

47

→

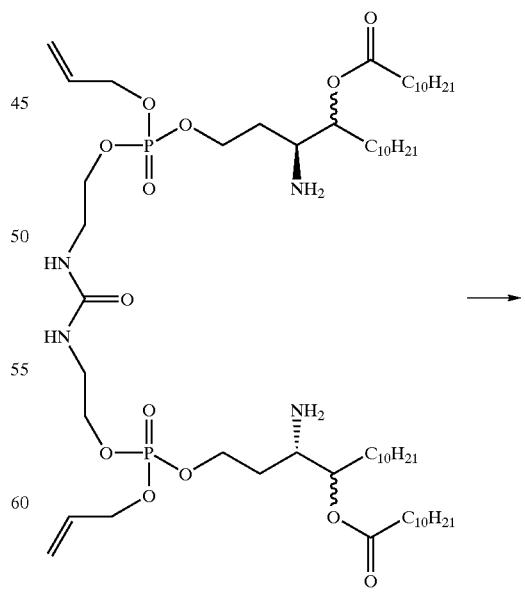

48

→

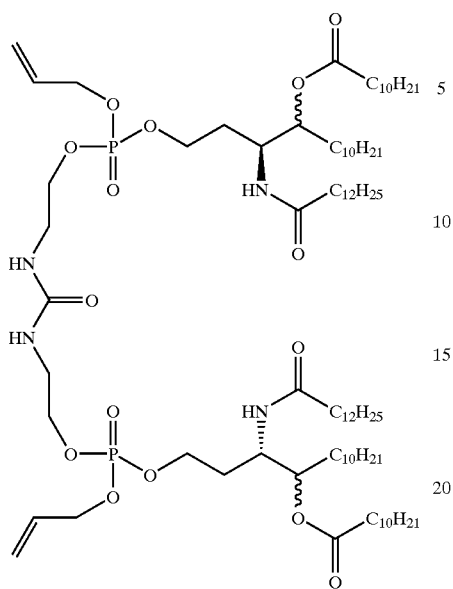

49

To a stirred solution of 48 (29 mg) in methylene chloride (0.5 mL) was added tridecanoic acid (36 mg) and EDC (44 mg). After stirring for 48 hours, an aqueous work-up followed by silica gel purification provided 49 (21 mg).

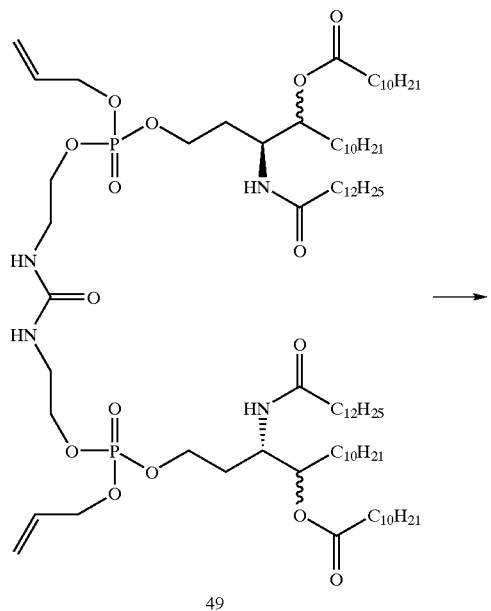

49

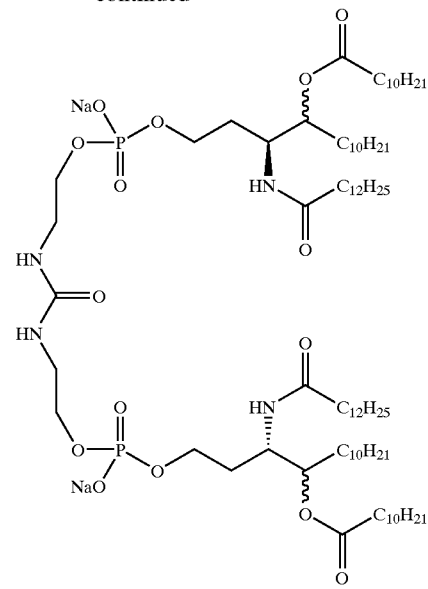

ER-805274

To a stirred solution of 49 (21 mg) in degassed chloroform (1.5 mL) was added phenylsilane (16 μL) and tetrakis(triphenylphosphine)palladium(0) (18 mg) at 0° C. After stirring for 10 minutes at 0° C. the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805274 (8.9 mg).

Example 6

Preparation of ER-805271

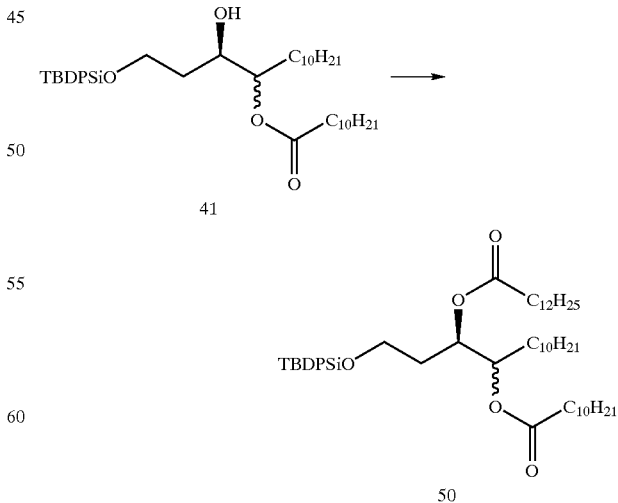

To a stirred solution of 41 (128 mg) in methylene chloride (2.0 mL) was added tridecanoic acid (83 mg), EDC (113 mg) and DMAP (5.0 mg). After stirring for 72 hours, an aqueous work-up and silica gel purification provided 50 (136 mg).

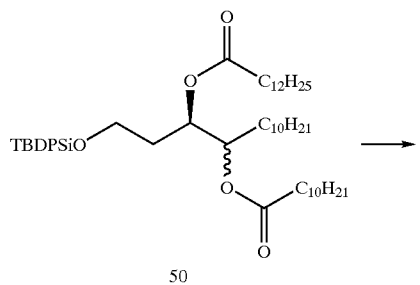

50

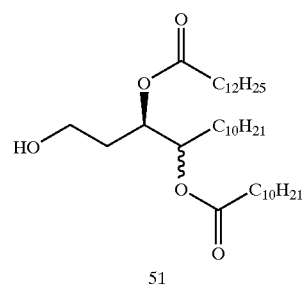

51

To a stirred solution of 50 (136 mg) in THF (0.8 mL) was added acetic acid (14 mg) followed by tetra-n-butylammonium fluoride (63 mg) at room temperature. After stirring for 16 hours the reaction mixture was quenched and purified using silica gel chromatography to provide 51 (82 mg).

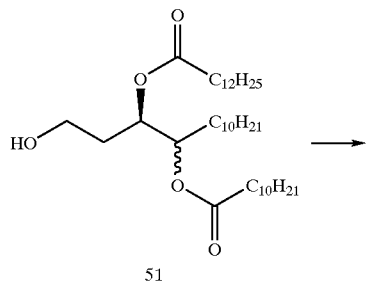

51

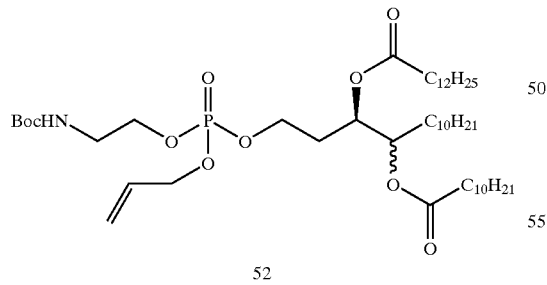

52

To a stirred solution of 51 (82 mg) in methylene chloride (0.7 mL) was added tetrazole (37 mg) followed by the phosphorylating reagent (89 mg) at 0° C. After stirring for 2 hours, the reaction mixture was poured onto a stirred suspension containing oxone (330 mg) in THF (1 mL) and water (1 mL). After an additional 2 hours stirring at 0° C. the mixture was worked-up and purified over silica gel to give 52 (70 mg).

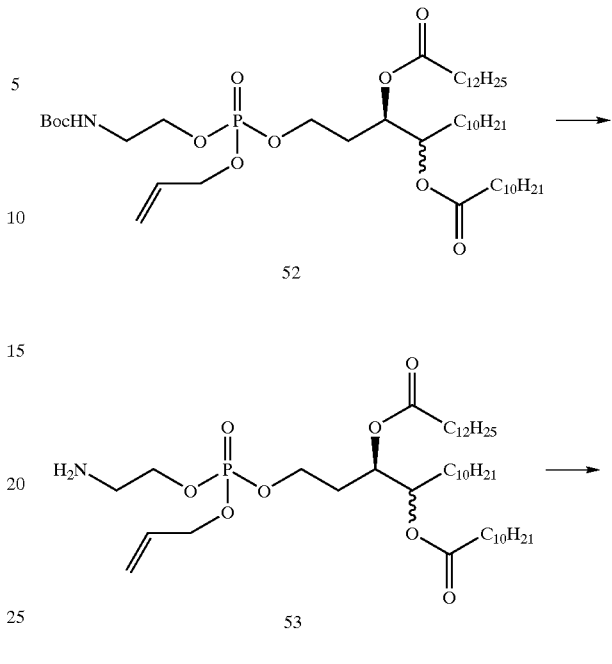

52

53

To a stirred solution of 52 (70 mg) in methylene chloride (0.10 mL) was added triethylsilane (0.13 mL) followed by trifluoroacetic acid (1.0 mL) at room temperature. After stirring for 2 hours the solvents were concentrated and azeotroped to dry using toluene. The crude amine 53 (40 mg) was dissolved in methylene chloride (0.5 mL) with saturated sodium bicarbonate (0.5 mL) followed by the dropwise addition of phosgene (0.014 mL of a 1.93 M solution in toluene) at 0° C. After stirring at room temperature for 2 hours the reaction was worked-up and purified by silica gel in the normal fashion to provide 54 (24 mg).

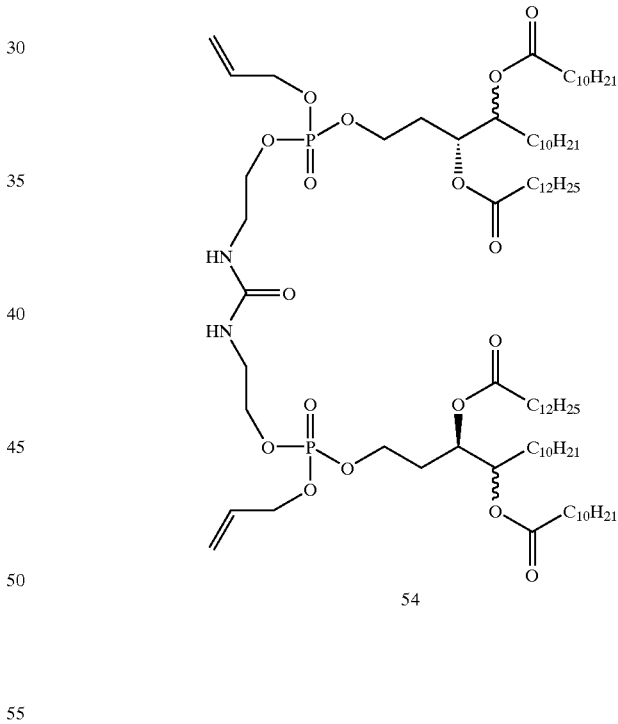

54

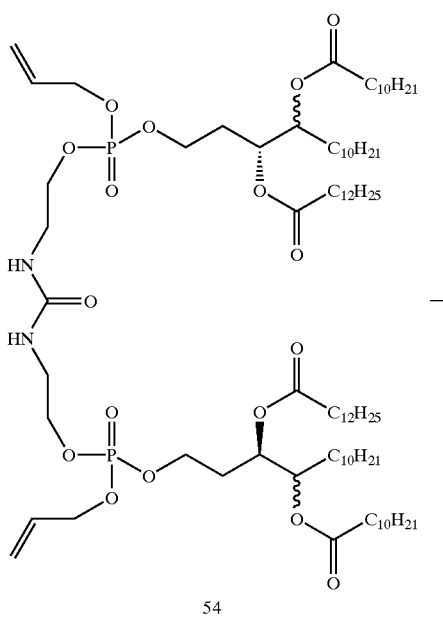

54

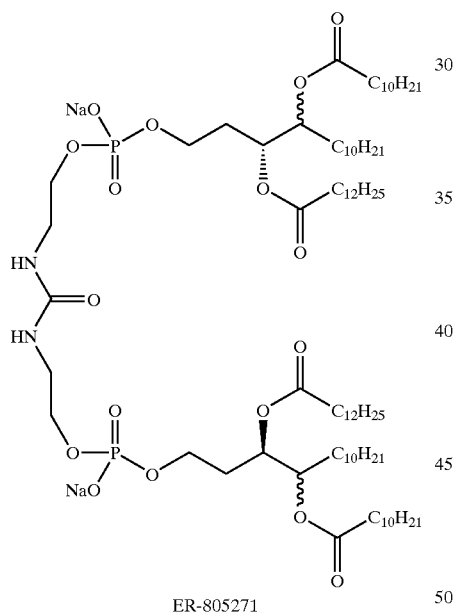

ER-805271

To a stirred solution of 54 (24 mg) in degassed chloroform (1.5 mL) was added phenylsilane (17 mg) and tetrakis(triphenylphosphine)palladium(0) (18 mg) at 0° C. After stirring for 10 minutes at 0° C. the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805271 (3.3 mg).

Example 7

Preparation of ER-805270

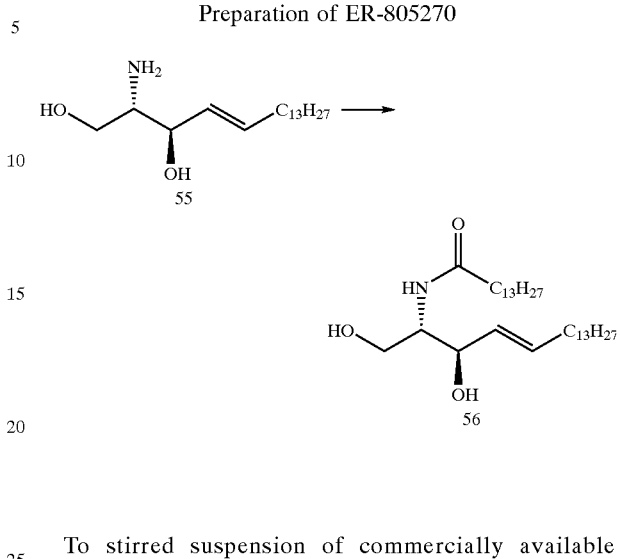

To stirred suspension of commercially available D-sphingosine sulphate, 55 (120 mg) in methylene chloride (5.0 mL) and saturated sodium bicarbonate (2.5 mL) was add dropwise tetradecanoyl chloride (99 mg) at 0° C. After stirring for 16 hours at room temperature, the reaction mixture was worked-up and purified by silica gel chromatography to provide 56 (183 mg).

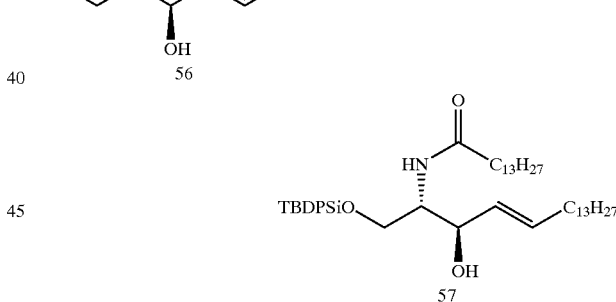

To a stirred solution of 56 (183 mg) in methylene chloride (3.6 mL) was added imidazole (39 mg) followed by tert-butyldiphenylsilyl chloride (109 mg). After stirring at room temperature for 16 hours, normal work-up followed by silica gel purification provided of 57 (193 mg).

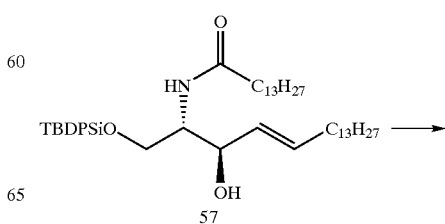

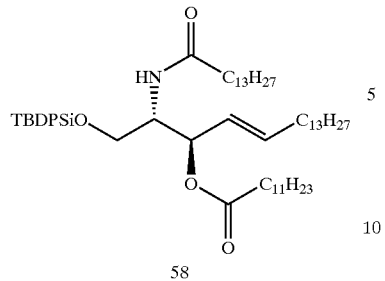

58

To a stirred solution of 57 (193 mg) in methylene chloride (0.5 mL) was added dodecanoic acid (74 mg), EDC, (70 mg) and DMAP (4 mg). After stirring for 16 hours, an aqueous work-up and silica gel purification provided 58 (219 mg).

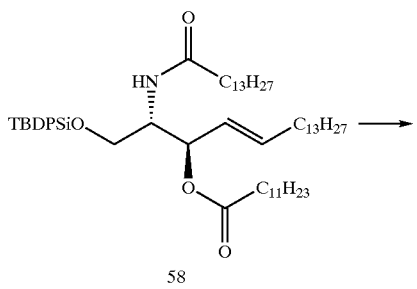

58

To a stirred solution of 58 (219 mg) in THF (1.0 mL) was added acetic acid (21 mg) followed by tetra-n-butylammonium fluoride (93 mg) at room temperature. After stirring for 48 hours the reaction mixture was quenched and purified using silica gel chromatography to provide 59 (140 mg).

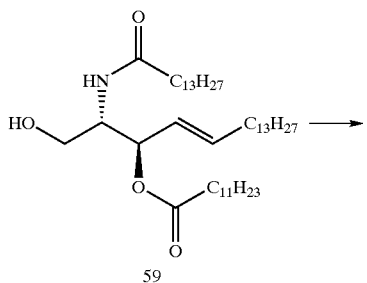

59

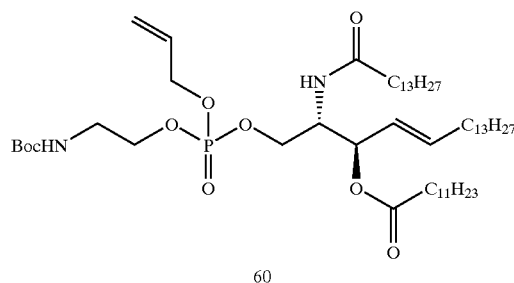

60

To a stirred solution of 59 (140 mg) in methylene chloride (1.0 mL) was added tetrazole (42 mg) followed by the phosphorylating reagent (100 mg) at 0° C. After stirring for 2 hours, the reaction mixture was poured onto a stirred suspension containing oxone (369 mg) in THF (1 mL) and water (1 mL) at 0° C. After an additional 16 hours of stirring at room temperature, the mixture was worked-up and purified over silica gel to give 60 (152 mg).

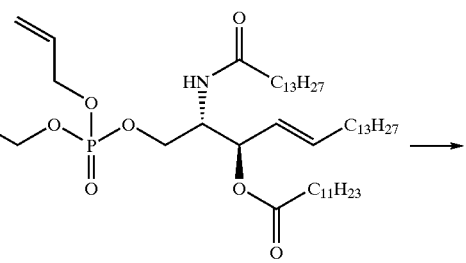

60

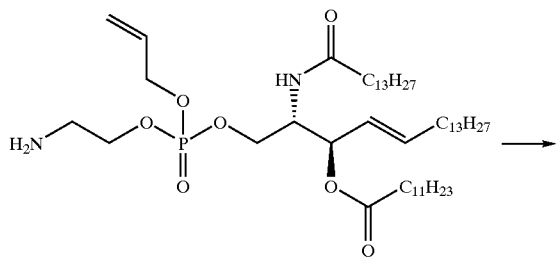

61

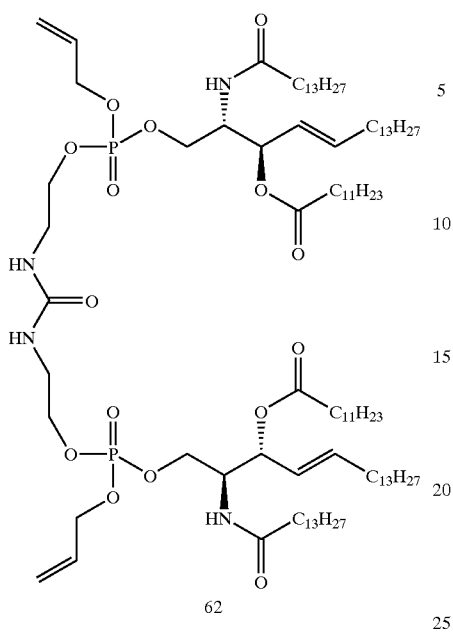

62

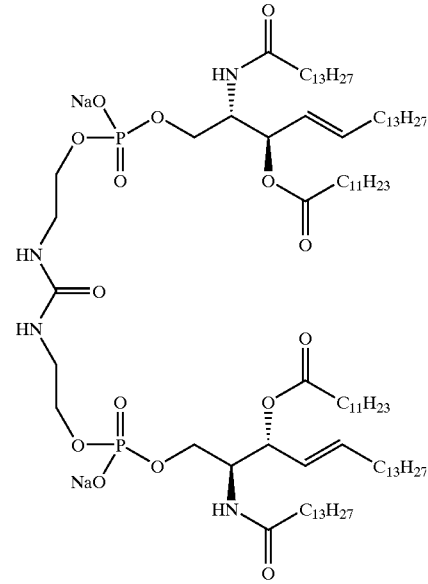

ER-805270

To a stirred solution of 60 (46 mg) in methylene chloride (0.2 mL) was added triethylsilane (0.12 mL) followed by trifluoroacetic acid (1.0 mL) at room temperature. After stirring for 1 hour the solvents were concentrated and azeotroped to dry using toluene. The crude amine 61 was dissolved in methylene chloride (0.6 mL) with saturated sodium bicarbonate (0.6 mL) followed by the dropwise addition of phosgene (0.014 mL of a 1.93 M solution in toluene) at 0° C. After stirring at room temperature for 2 hours the reaction was worked-up and purified by silica gel in the normal fashion to provide 62 (44 mg).

To a stirred solution of 62 (44 mg) in degassed chloroform (2 mL) was added phenylsilane (40 μL) and tetrakis (triphenylphosphine)palladium(0) (23 mg) at 0° C. After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805270 (7.1 mg).

Example 8

Preparation of ER-805328.

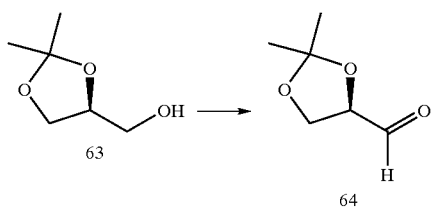

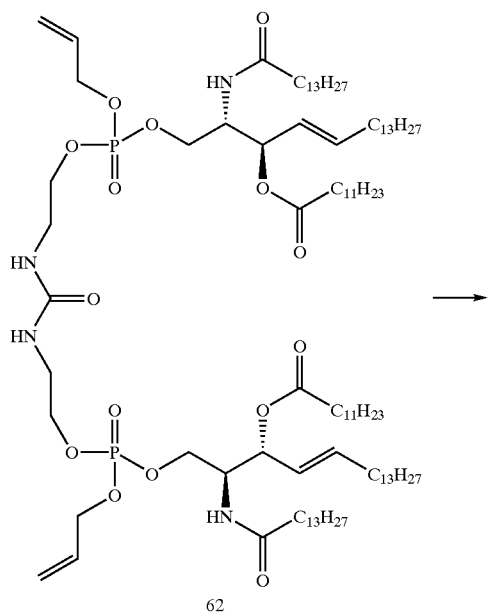

62

To a stirred solution of oxalyl chloride (0.66 mL) in methylene chloride (20 mL) at −78° C. was added dropwise DMSO (1.06 mL). After stirring for 15 minutes commercially available protected glycerol 63 (0.62 g) in methylene chloride (5 mL) was added dropwise followed by stirring for an additional 30 minutes. Triethyl amine (3.5 mL) was added dropwise followed by warming to room temperature and a usual work-up using dilute HCl. The crude aldehyde 64 was immediately used in the next step.

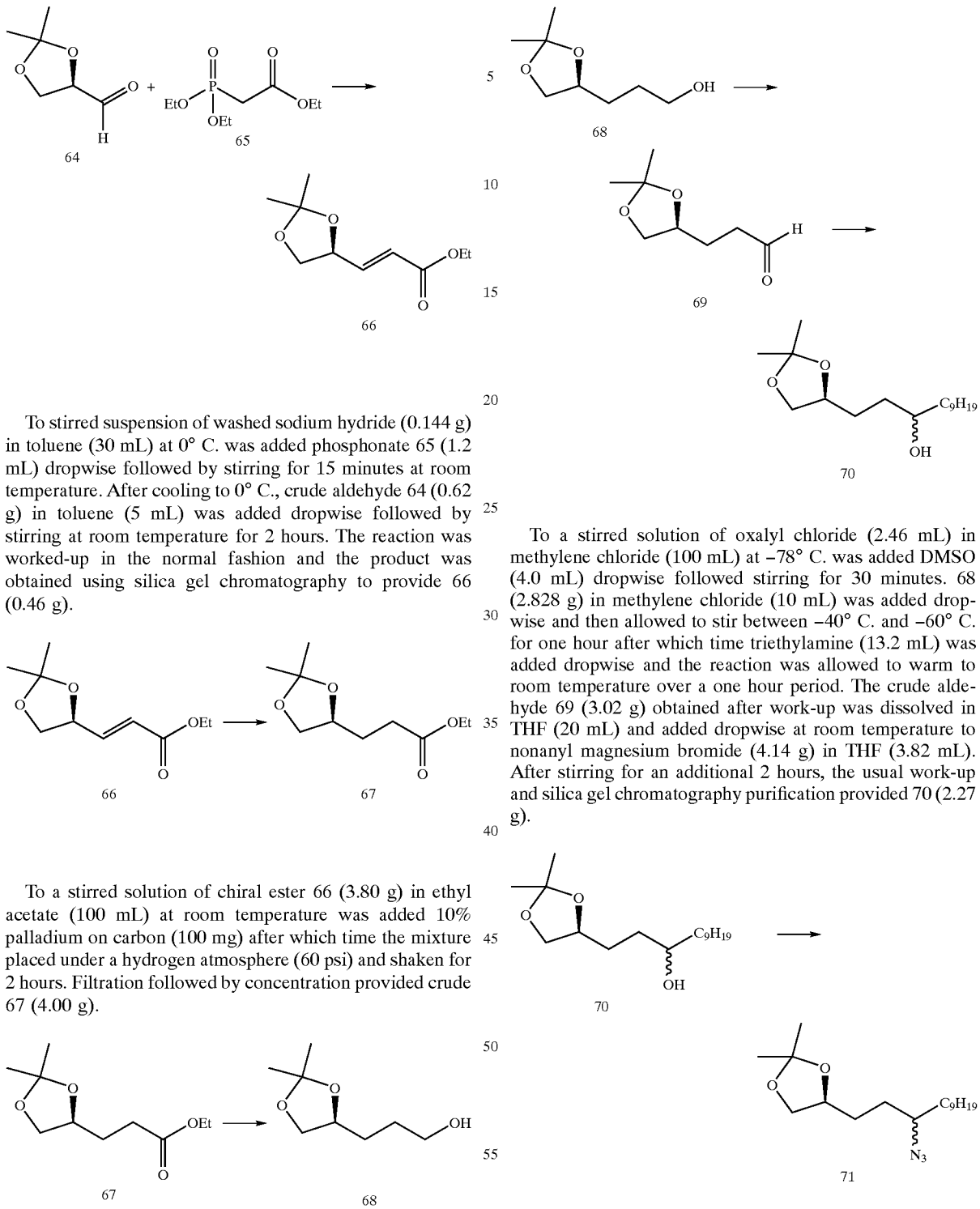

To stirred suspension of washed sodium hydride (0.144 g) in toluene (30 mL) at 0° C. was added phosphonate 65 (1.2 mL) dropwise followed by stirring for 15 minutes at room temperature. After cooling to 0° C., crude aldehyde 64 (0.62 g) in toluene (5 mL) was added dropwise followed by stirring at room temperature for 2 hours. The reaction was worked-up in the normal fashion and the product was obtained using silica gel chromatography to provide 66 (0.46 g).

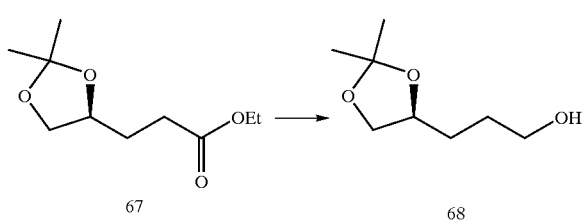

To a stirred solution of chiral ester 66 (3.80 g) in ethyl acetate (100 mL) at room temperature was added 10% palladium on carbon (100 mg) after which time the mixture placed under a hydrogen atmosphere (60 psi) and shaken for 2 hours. Filtration followed by concentration provided crude 67 (4.00 g).

To a stirred solution of 67 (4.00 g) in hexanes (100 mL) at 0° C. was added DIBAL (1.0 M in hexanes—40 mL) dropwise. After stirring for an additional 20 minutes at 0° C., the reaction mixture was quenched first with methanol:water followed by Rochelle's salts. 68 (2.66 g) was obtained after work-up and silica gel chromatography.

To a stirred solution of oxalyl chloride (2.46 mL) in methylene chloride (100 mL) at −78° C. was added DMSO (4.0 mL) dropwise followed stirring for 30 minutes. 68 (2.828 g) in methylene chloride (10 mL) was added dropwise and then allowed to stir between −40° C. and −60° C. for one hour after which time triethylamine (13.2 mL) was added dropwise and the reaction was allowed to warm to room temperature over a one hour period. The crude aldehyde 69 (3.02 g) obtained after work-up was dissolved in THF (20 mL) and added dropwise at room temperature to nonanyl magnesium bromide (4.14 g) in THF (3.82 mL). After stirring for an additional 2 hours, the usual work-up and silica gel chromatography purification provided 70 (2.27 g).

To a stirred solution of 70 (1.13 g) in THF (40 mL) at room temperature was added triphenylphosphine (1.55 g), diphenylphosphoryl azide (1.63 g), and diethyl azodicarboxylate (DEAD—1.03 g). After stirring for 15 minutes triphenylphosphine (1.04 g), diphenylphosphoryl azide (1.09 g), and diethyl azodicarboxylate (0.69 g) were added to the mixture and the final mixture was stirred for 20 minutes, Crude 71 (1.83 g) was obtained after work-up and silica gel chromatography.

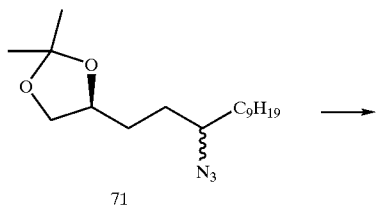

71

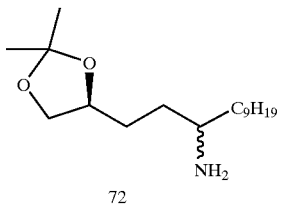

72

To crude 71 (1.83 g) was added a (PhS)$_3$SnH*Et$_3$N complex (0.5 M—20 mL) in methylene chloride at room temperature. The reaction mixture was stirred for 20 minutes after which time it was purified by silica gel chromatography to provide crude 72 (2.01 g) that was used immediately in the next step.

72

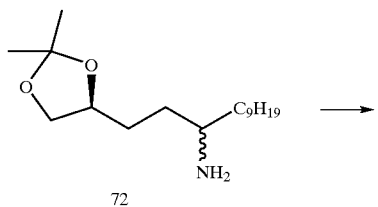

73

To stirred suspension of crude 72 (2.01 g) in THF (15 mL) and saturated sodium bicarbonate (30 mL) at 0° C. was add dropwise tetradecanoyl chloride (1.74 g). After stirring for 30 minutes at room temperature, the reaction mixture was worked-up and purified by silica gel chromatography to provide 73 (1.58 g).

73

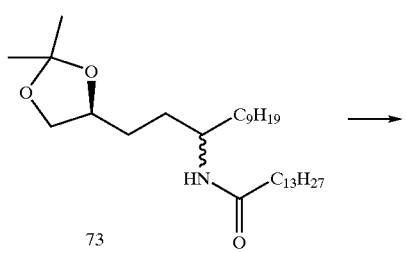

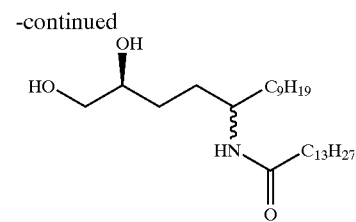

74

To a stirred solution of 73 (785 mg) in THF (8 mL) at room temperature was added dilute HCl (2.4 N—10 mL). After stirring the reaction mixture for 2 hours, the crude product 74 (667 mg) was obtained by a normal work-up.

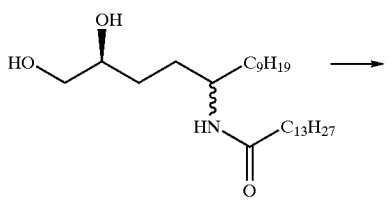

74

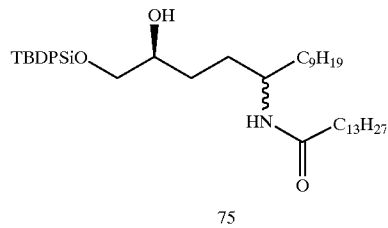

75

To a stirred solution of 71 (667 mg) in methylene chloride (16 mL) at room temperature was added imidazole (161 mg) followed by tert-butyldiphenylsilyl chloride (435 mg). After stirring for 18 hours, normal work-up followed by silica gel purification provided 72 (850 mg).

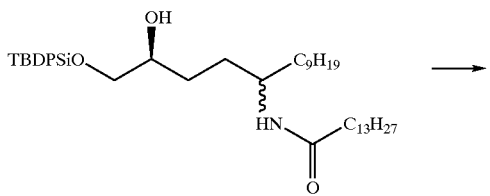

75

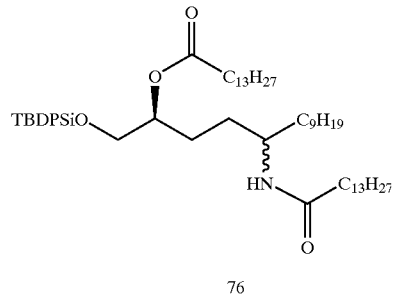

76

To a stirred solution of 72 (106 mg) in methylene chloride (0.5 mL) at room temperature was added tetradecanoic acid (42 mg), EDC (44 mg) and DMAP (4 mg). After stirring for 16 hours, an aqueous work-up, and silica gel purification provided 73 (132 mg).

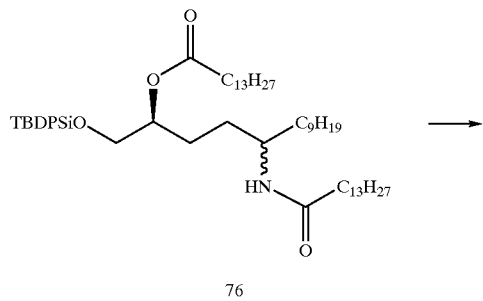

76

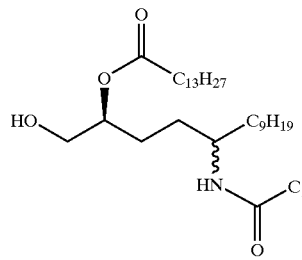

77

To a stirred solution of 73 (132 mg) in THF (1.0 mL) at room temperature was added acetic acid (13 mg) followed by tetra-n-butylammonium fluoride (58 mg). After stirring for 16 hours the reaction mixture was quenched and purified using silica gel chromatography to provide 74 (80 mg).

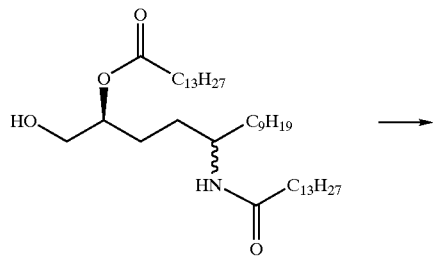

77

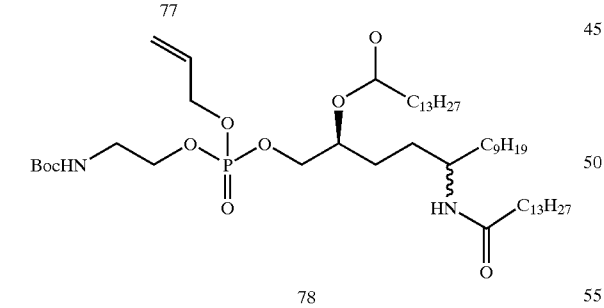

78

To a stirred solution of 74 (80 mg) in methylene chloride (0.6 mL) at 0° C. was added tetrazole (25 mg) followed by the phosphorylating reagent (60 mg). After stirring for 1 hour, the reaction mixture was poured onto a stirred suspension containing oxone (204 mg) in THF (1 mL) and water (1 mL). After an additional 1 hour stirring at 0° C. the mixture was worked up and purified over silica gel to give 75 (65 mg).

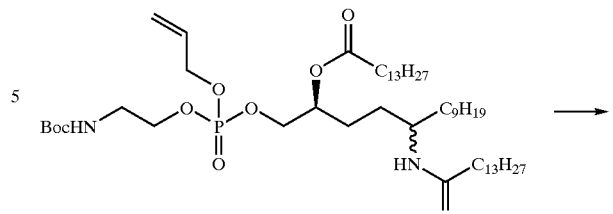

78

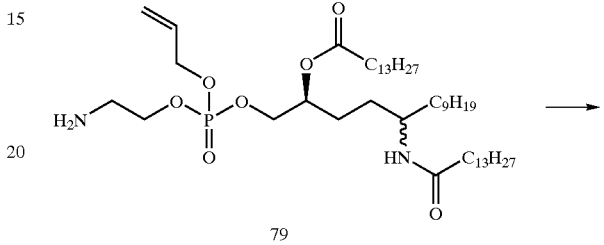

79

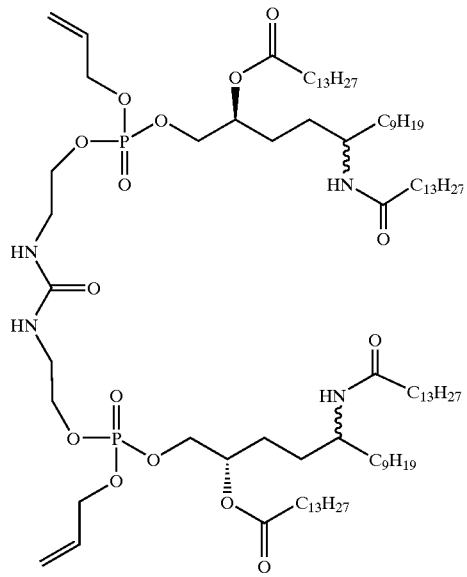

80

To a stirred solution of 75 (65 mg) in methylene chloride (0.1 mL) at room temperature was added triethylsilane (82 mg) followed by trifluoroacetic acid (1.0 mL). After stirring for 2 hours the solvents were concentrated and azeotroped to dry using toluene. The crude amine 76 was dissolved in methylene chloride (0.7 mL) with saturated sodium bicarbonate (0.7 mL) at 0° C. followed by the dropwise addition of phosgene (0.019 mL of a 1.93 M solution in toluene). After stirring at room temperature for 2 hours the reaction was worked-up and purified by silica gel in the normal fashion to provide 77 (50 mg).

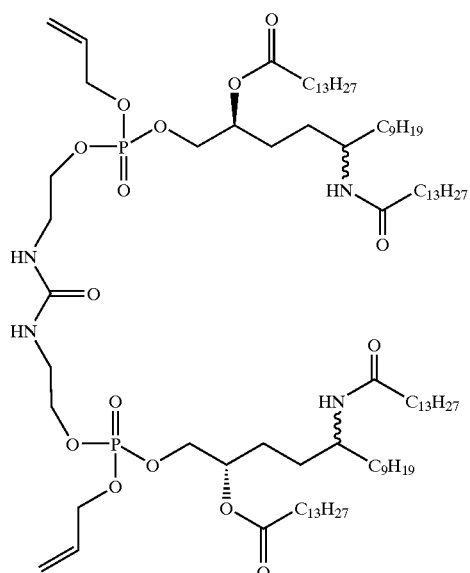

80

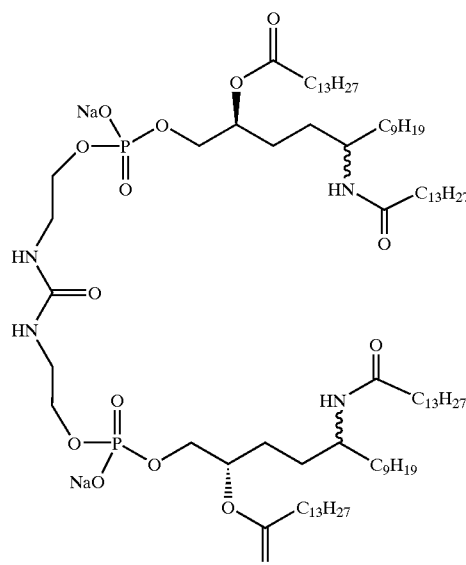

ER-805328

To a stirred solution of 77 (50 mg) in degassed chloroform (3 mL) at 0° C. was added phenylsilane (32 mg) and tetrakis(triphenyl-phosphine)palladium(0) (26 mg). After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805328 (38 mg).

Example 9

Preparation of ER-805329

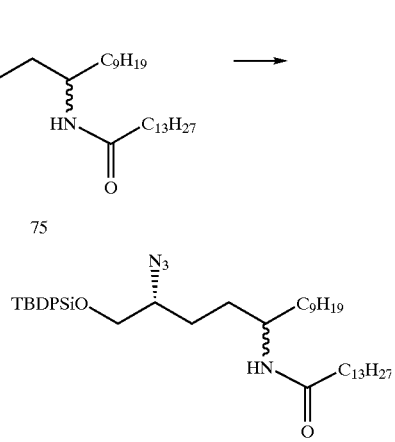

75

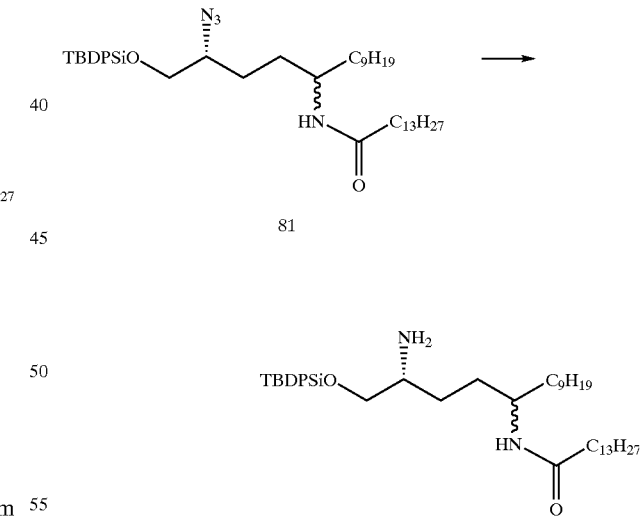

81

To a stirred solution of 75 (0.14 g) in THF (3 mL) at room temperature was added triphenylphosphine (0.159 g), diphenylphosphoryl azide (0.167 g), and DEAD (0.105 g). After stirring for 1 hr, crude azide 81 (0.14 g) was obtained after work-up.

81

82

The crude 81 (0.14 g) was added a $(PhS)_3SnH*Et_3N$ complex (0.5 M—5 mL) in methylene chloride at room temperature. The reaction mixture was stirred for 20 minutes after which time it was purified by silica gel chromatography to provide crude 82 (0.14 g) that was used immediately in the next step.

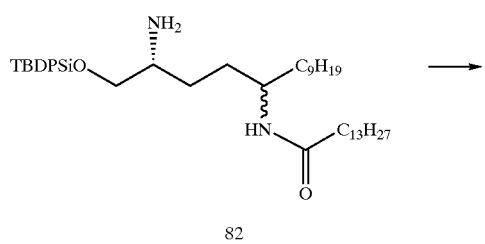

82

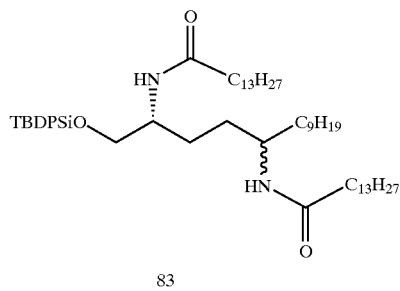

83

To a stirred solution of 82 (0.14 g) in methylene chloride (2.0 mL) at room temperature was added tetradecanoic acid (92 mg) and EDC (116 mg). After stirring for 16 hours, an aqueous work-up, and silica gel purification provided 83 (190 mg).

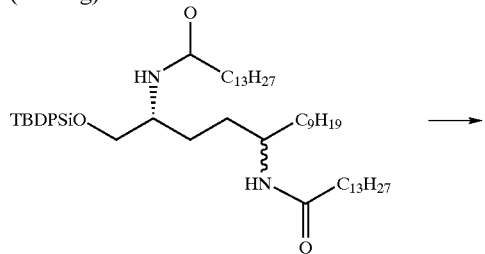

83

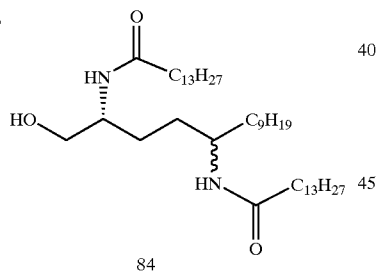

84

To a stirred solution of 83 (190 mg) in THF (2.0 mL) at room temperature was added acetic acid (20 mg) followed by tetra-n-butylammonium fluoride (89 mg). After stirring for 16 hours the reaction mixture was quenched and purified using silica gel chromatography to provide 84 (104 mg).

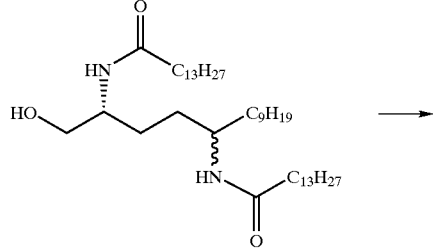

84

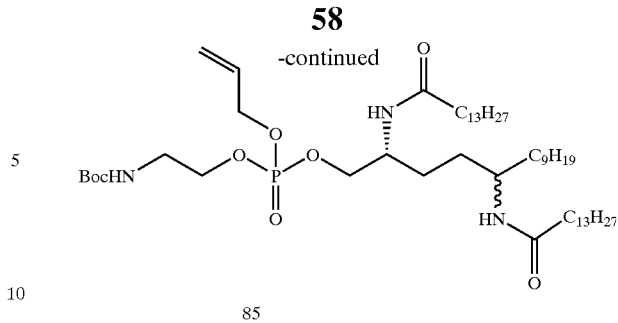

85

To a stirred solution of 84 (104 mg) in methylene chloride (0.8 mL) at 0° C. was added tetrazole (42 mg) followed by the phosphorylating reagent (100 mg). After stirring for 1 hour, the reaction mixture was poured onto a stirred suspension containing oxone (615 mg) in THF (2 mL) and water (2 mL). After an additional 1 hour stirring at 0° C. the mixture was worked up and purified over silica gel to give 85 (82 mg).

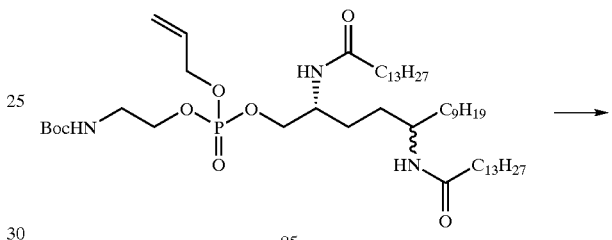

85

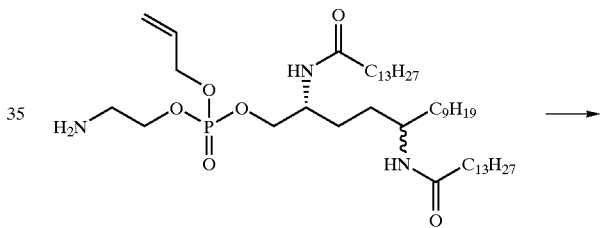

86

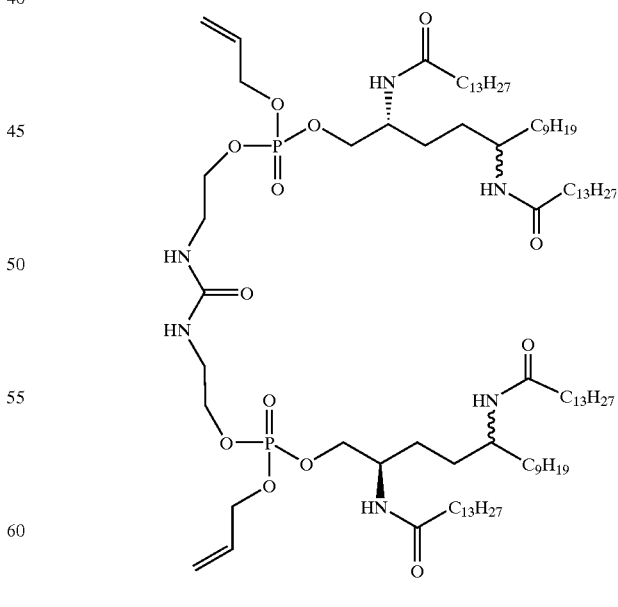

87

To a stirred solution of 85 (82 mg) in methylene chloride (0.1 mL) at room temperature was added triethylsilane (103 mg) followed by trifluoroacetic acid (1.0 mL). After stirring for 2 hours the solvents were concentrated and azeotroped to dry using toluene. The crude amine 86 was dissolved in methylene chloride (0.8 mL) with saturated sodium bicarbonate (0.8 mL) at 0° C. followed by the dropwise addition of phosgene (0.023 mL of a 1.93 M solution in toluene). After stirring at room temperature for 2 hours the reaction was worked-up and purified by silica gel in the normal fashion to provide 87 (63 mg).

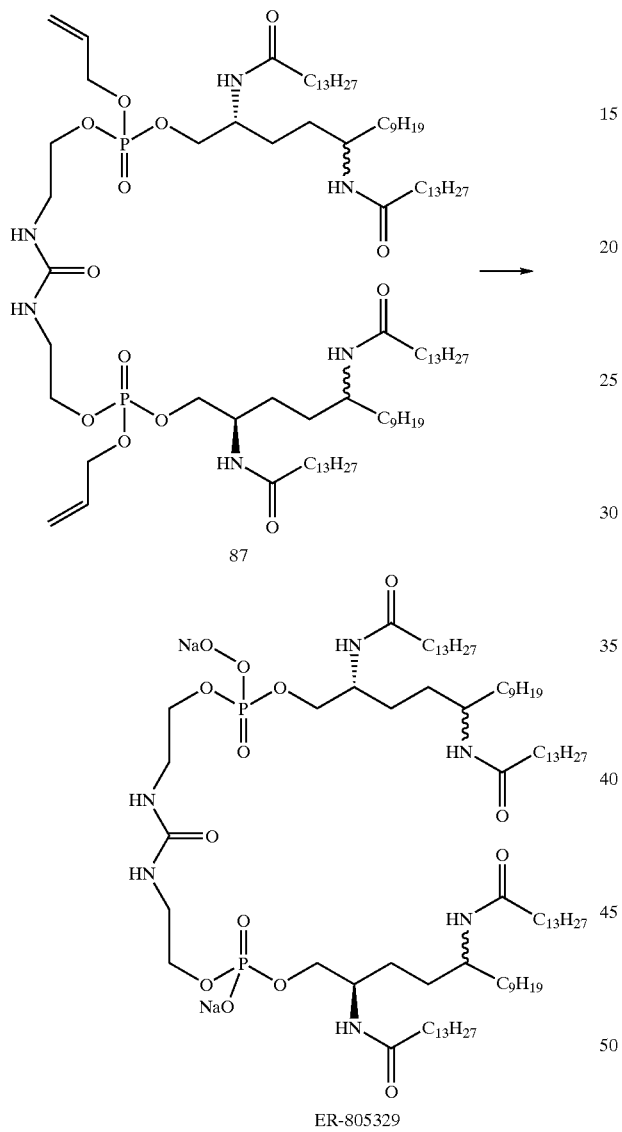

To a stirred solution of 87 (63 mg) in degassed chloroform (3 mL) at 0° C. was added phenylsilane (40 mg) and tetrakis(triphenyl-phosphine)palladium(0) (33 mg). After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805329 (5.1 mg).

Example 10

Preparation of ER-805517

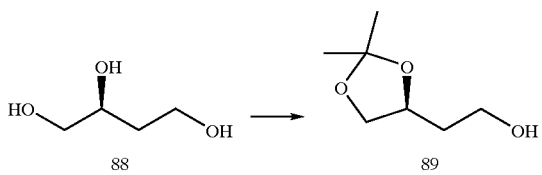

To a solution of commercially available, chiral 88 (3.18 g) in acetone (100 mL) at room temperature was added 2,2-dimethoxypropane (4.05 mL) and p-toluenesulfonic acid (0.57 g) followed by stirring for 72 hours. 89 (3.67 g) was obtained after work-up and silica gel purification.

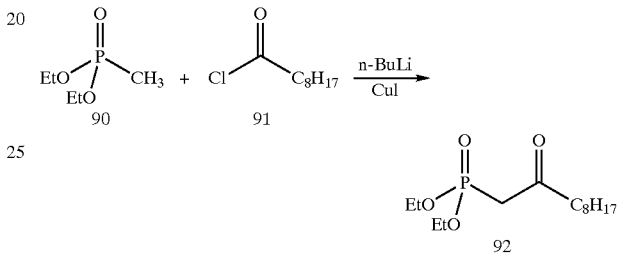

To a stirred solution of methyl phosphonate 90 (4.56 g) in THF (100 mL) at −78° C. was added dropwise n-butyl lithium (1.6 M in hexanes—18.8 mL). After stirring for 5 minutes, copper(I) iodide (5.7 g) was added followed by stirring for an additional 2 h at −5° C. The acid chloride 91 (5.31 g) was added dropwise to the clear yellow mixture after which time the reaction was stirred at room temperature for 1 hour. 92 (7.28 g) was obtained after the usual work-up and silica gel chromatography.

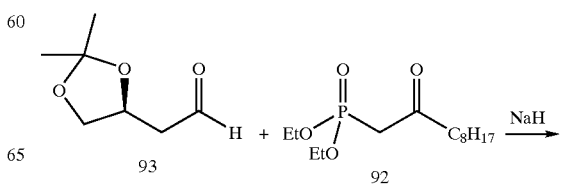

To a stirred solution of oxalyl chloride (2.54 g) in methylene chloride (65 mL) at −78° C. was added DMSO (2.83 mL) dropwise followed stirring for 30 minutes. 89 (1.90 g) in methylene chloride (5 mL) was added dropwise and then allowed to stir between −40° C. and −60° C. for one hour after which time triethylamine (9.04 mL) was added dropwise and the reaction was allowed to warm to room temperature over a one hour period. The crude aldehyde 93 (3.02 g) obtained after work-up was immediately used in the next reaction without further purification.

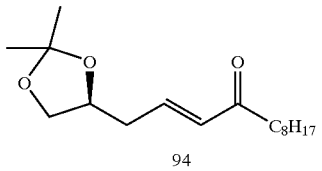

94

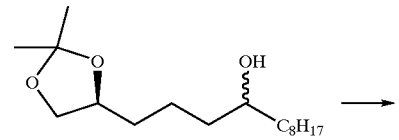

96

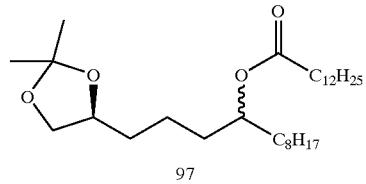

97

To a stirred suspension of washed sodium hydride (79 mg) in toluene (30 mL) at 0° C. was added phosphonate 92 (0.88 g). After stirring at room temperature for 30 minutes the reaction mixture was cooled to −15° C. after which time aldehyde 93 (0.43 g) was added. The final reaction mixture was allowed to stir at room temperature for 30 minutes followed by the usual work-up and silica gel chromatography purification to provide 94 (1.06 g).

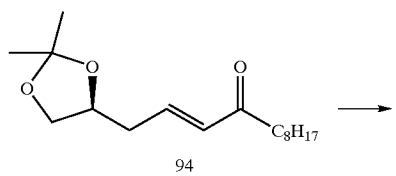

94

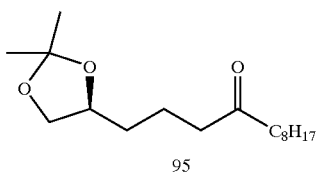

95

To a stirred solution of 94 (0.726 g) in ethyl acetate (25 mL) at room temperature was added 20% palladium hydroxide (100 mg) after which time the mixture was placed under a hydrogen atmosphere (60 psi) and shaken for 16 hours. Filtration followed by concentration provided 95 (0.72 g) without further purification.

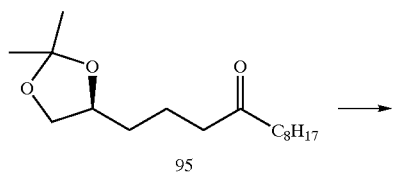

95

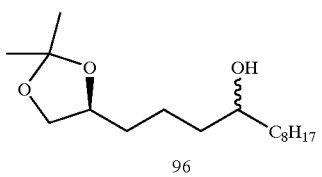

96

To a stirred solution of 95 (0.72 g) in methanol (20 mL) at room temperature was added sodium borohydride (150 mg) at 0° C. after which time the mixture was stirred for 1.5 hours. Work-up followed by concentration provided 96 (0.67 g) without further purification.

To a stirred solution of 96 (0.67 g) in methylene chloride (10 mL) at room temperature was added tridecanoic acid (0.66 g), EDC (0.72 g) and DMAP (29 mg). After stirring for 16 hours, additional EDC (0.10 g) was add and then stirred for and additional 1 h. Aqueous work-up and silica gel purification provided 97 (1.01 g).

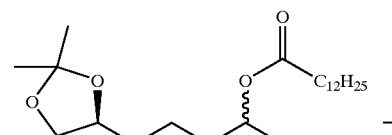

97

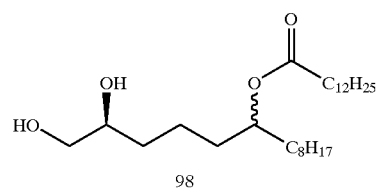

98

To a stirred solution of 97 (1.01 g) in THF (21 mL) at room temperature was added 3 N HCl (21 mL). After stirring the reaction mixture for 26 hours, the crude product 98 (0.92 g) was obtained by a normal work-up.

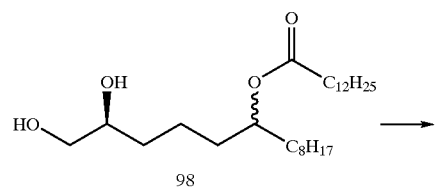

98

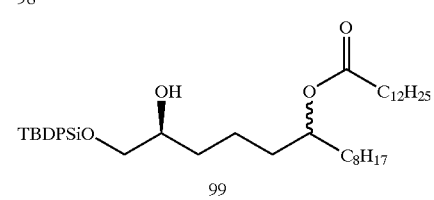

99

To a stirred solution of 98 (0.94 g) in methylene chloride (10 mL) at 0° C. was added imidazole (214 mg) followed by tert-butyldiphenylsilyl chloride (608 mg). After stirring at room temperature for 72 hours, normal work-up followed by silica gel purification provided 99 (1.44 g).

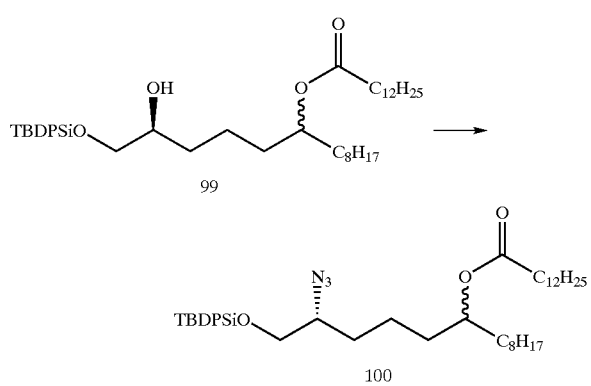

To a stirred solution of 99 (552 mg) in THF (8 mL) at room temperature was added triphenylphosphine (639 mg), diphenylphosphoryl azide (671 mg), and DEAD (425 mg). After stirring for 1 hr, crude azide 100 (402 mg) was obtained after work-up.

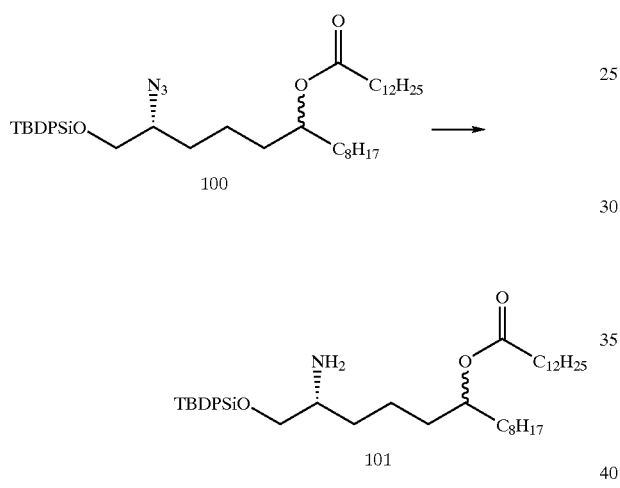

To 100 (420 mg) was added a (PhS)$_3$SnH*Et$_3$N complex (0.5 M—3.43 mL) in methylene chloride at room temperature. The reaction mixture was stirred for 20 hours after which time it was purified by silica gel chromatography to provide 101 (434 mg) that was used immediately in the next step.

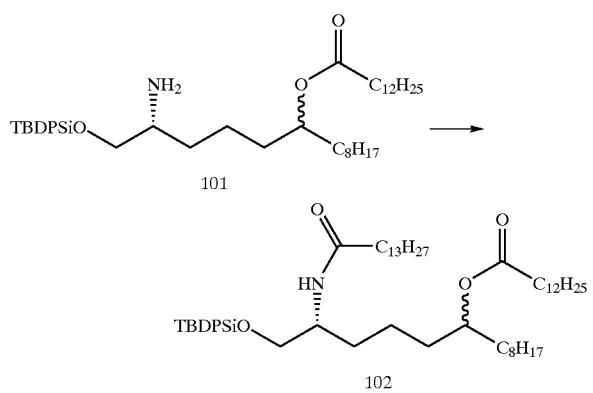

To a stirred solution of 101 (434 mg) in methylene chloride (6.0 mL) at room temperature and saturated aqueous sodium bicarbonate (6.0 mL) was added tetradecanoyl chloride (156 mg). After stirring for 15 minutes, a work-up and silica gel purification provided 102 (422 mg).

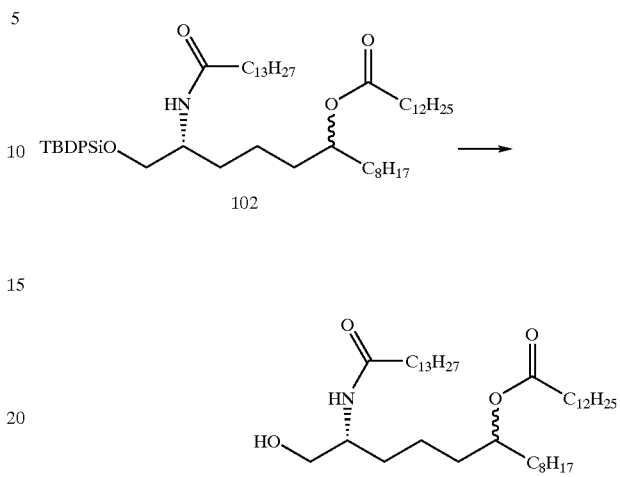

To a stirred solution of 102 (422 mg) in THF (2.0 mL) at room temperature was added acetic acid (43 mg) followed by tetra-n-butylammonium fluoride (189 mg). After stirring for 16 hours the reaction mixture was quenched and purified using silica gel chromatography to provide 103 (258 mg).

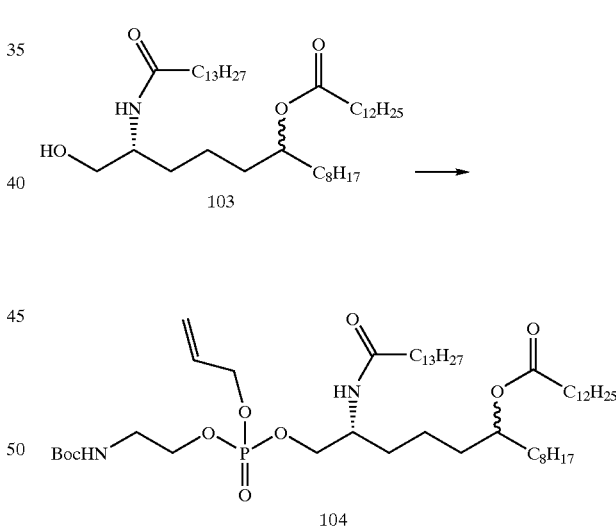

To a stirred solution of 103 (258 mg) in methylene chloride (2.0 mL) at 0° C. was added tetrazole (112 mg) followed by the phosphorylating reagent (266 mg). After stirring for 2 hours at room temperature, the reaction mixture was poured onto a stirred suspension containing oxone (1.48 g) in THF (2 mL) and water (2 mL) at 0° C. After an additional 1 hour stirring at 0° C. the mixture was worked up and purified over silica gel to give 104 (325 mg).

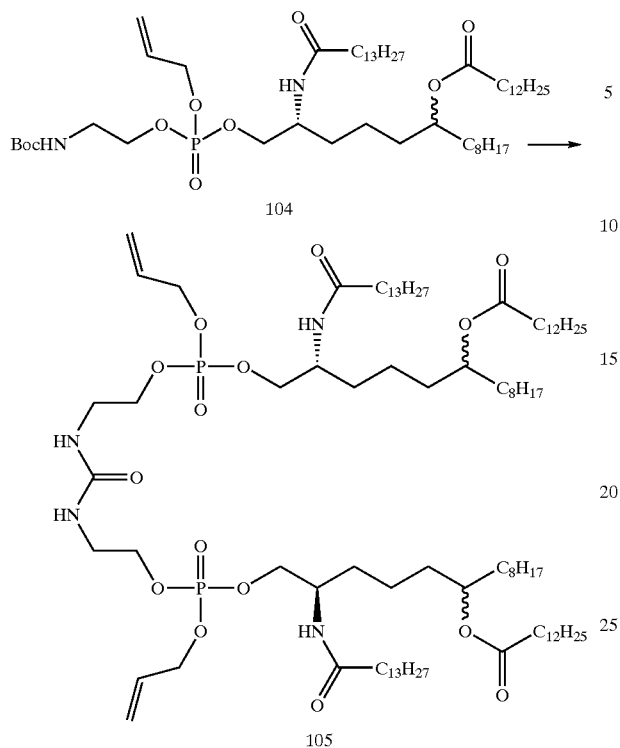

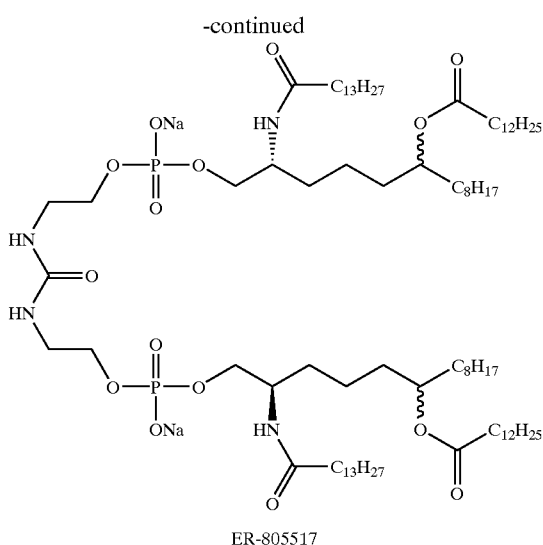

To a stirred solution of 104 (313 mg) in methylene chloride (0.1 mL) at room temperature was added triethylsilane (0.64 μL) followed by trifluoroacetic acid (4.0 mL). After stirring for 2 hours the solvents were concentrated and azeotroped to dry using toluene. The crude amine 76 was dissolved in methylene chloride (3.4 mL) with saturated aqueous sodium bicarbonate (3.4 mL) at 0° C. followed by the dropwise addition of phosgene (94 μL of a 1.93 M solution in toluene). After stirring at room temperature for 3 hours the reaction was worked-up and purified by silica gel in the normal fashion to provide 105 (143 mg).

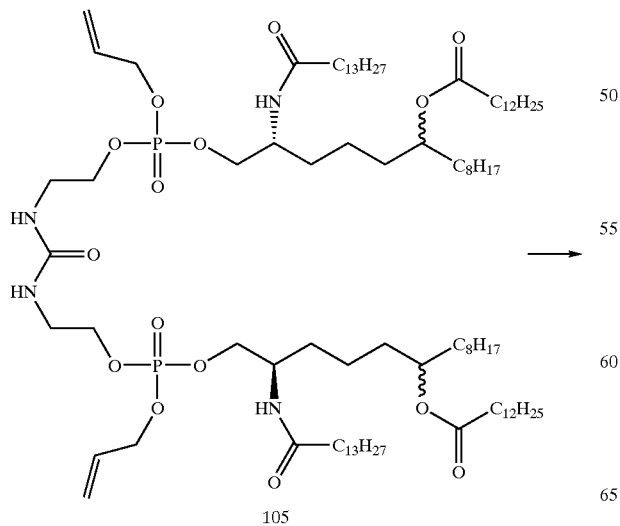

To a stirred solution of 105 (143 mg) in degassed chloroform (8 mL) at 0° C. was added phenylsilane (94 mg) and tetrakis(triphenyl-phosphine)palladium(0) (75 mg). After stirring for 0.5 hours at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided the desired product ER-805517 (84 mg).

Example 11

Preparation of ER-805518 and ER-805519

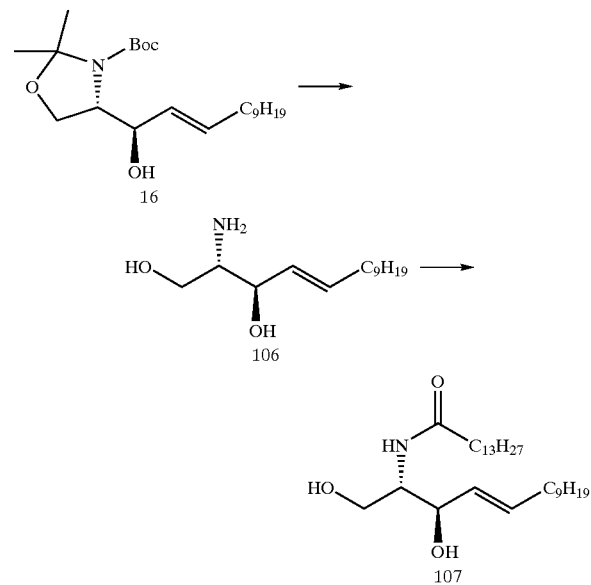

To a stirred solution of 16 (427 mg) in methanol (20 mL) at 0° C. was added anhydrous HCl gas for 10 minutes after which time the reaction mixture was warmed to room temperature and stirred for an additional 2 h. After concentration of the mixture to dryness, the crude product was lyophilized to dryness to provide crude 106 (307 mg). 106 (307 mg) was dissolved in THF (2 mL) and saturated sodium bicarbonate was added (4 mL) at 0° C. followed by the dropwise addition of tetradecanoyl chloride (0.31 mL) followed by vigorous stirring for 30 minutes at room temperature. Normal work-up and silica gel purification provided 107 (266 mg).

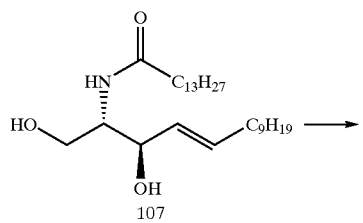
107

To a stirred solution of 107 (266 mg) in methylene chloride (5 mL) at room temperature was added imidazole (60 mg) followed by tert-butyldiphenylsilyl chloride (170 mg). After stirring for 20 hours, normal work followed by silica gel purification provided isomer 108 (277 mg).

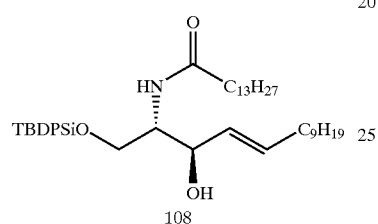
108

To a stirred solution of 108 (154 mg) in methylene chloride (2.0 mL) at room temperature was added lauric acid (104 mg), EDC (123 mg) and DMAP (5 mg). After stirring for 16 hours, aqueous work-up, and silica gel purification provided 109 (361 mg).

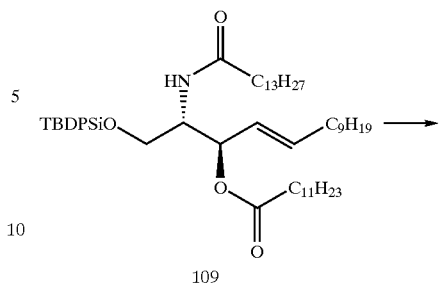
109

To a stirred solution of 109 (361 mg) in THF (2.0 mL) at room temperature was added acetic acid (36 mg) followed by tetra-n-butylammonium fluoride (157 mg). After stirring for 72 hours the reaction mixture was quenched and purified using silica gel chromatography to provide 110 (134 mg).

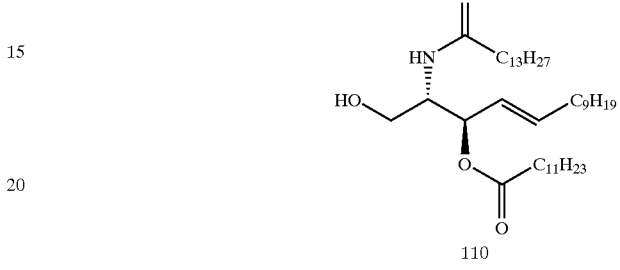
110

To a stirred solution of 110 (210 mg) in methylene chloride (1.66 mL) at room temperature was added tetrazole (93 mg) followed by the phosphorylating reagent (221 mg). After stirring for 2 hours, the reaction mixture was poured onto a stirred suspension containing oxone (1.48 g) in THF (2 mL) and water (5 mL) at 0° C. After an additional 1 hour stirring at 0° C. the mixture was worked up and purified over silica gel to give 111 (174 mg).

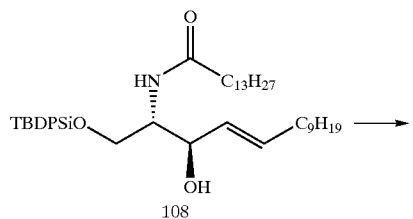
108

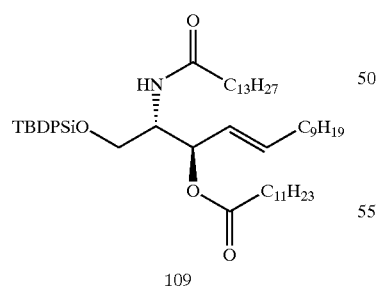
109

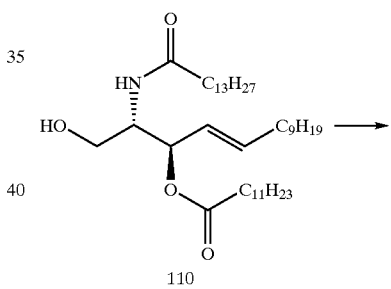
110

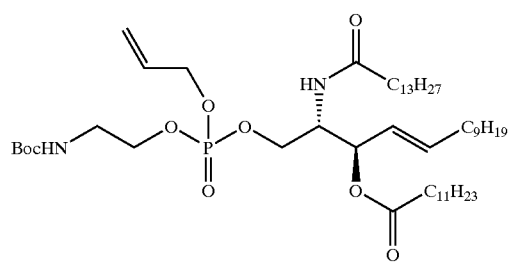
111

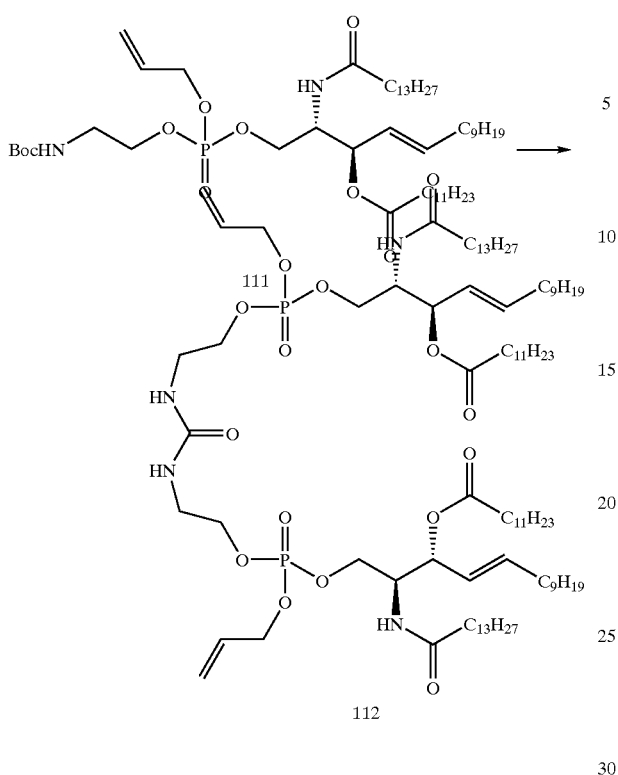

111

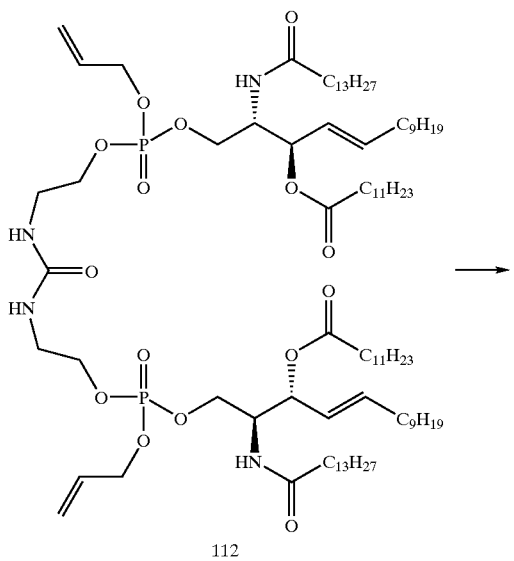

112

To a stirred solution of 111 (174 mg) in methylene chloride (0.10 mL) at room temperature was added triethylsilane (0.31 mL) followed by trifluoroacetic acid (2.0 mL). After stirring for 2 hours the solvents were concentrated and azeotroped to dry using toluene. The crude amine 112 was dissolved in methylene chloride (2.0 mL) with saturated aqueous sodium bicarbonate (2.0 mL) at 0° C. followed by the dropwise addition of phosgene (53 μL of a 1.93 M solution in toluene). After stirring at room temperature for 2 hours the reaction was worked-up and purified by silica gel in the normal fashion to provide 113 (124 mg).

ER-805518
Isomer A

+

ER-805519
Isomer B

To a stirred solution of 113 (124 mg) in degassed chloroform (7 mL) at 0° C. was added phenylsilane (825 mg) and tetrakis(triphenyl-phosphine)palladium(0) (66 mg). After stirring for 1 hour at room temperature the reaction mixture was diluted with a 2:3:1 ratio of chloroform:methanol:water (5 mL) and stirred for an additional 30 minutes. The mixture was poured over DEAE-cellulose (20 mL) and eluted with an increasing concentration of ammonium acetate (0.0–0.05 M) in 2:3:1 ratio of chloroform:methanol:water (100 mL). HPLC purification (silica gel with hexane:isopropanol:water gradient elution) provided two isomeric products, isomer A: ER-805518 (68 mg) and isomer B: ER-805519 (28 mg).

BIOLOGICAL EXAMPLES

Example 12

Induction of Cytokines (in vitro)

The ability to trigger a stimulatory response in macrophages is likely a necessary characteristic of molecules with imunoadjuvant properties. Therefore, the ability of compounds to stimulate release of TNF-α and other cytokines from immune cells is tested as an indication of their ability to stimulate an immune response, which may result in adjuvant activity.

The most readily available human system to test compound activity on monocytes/macrophages is in whole blood. Various concentrations of compounds of the invention were added as 10×stocks in 50 µl of 5% dextrose followed by 50 µl of 5% dextrose into 400 µl of heparinized whole blood obtained from normal volunteers (18–51 years old; 110–230 lb) into the wells of plastic assay plates, for a total volume of 500 µl/well (final concentration of whole blood was 80%). The 10×stocks were made by dissolving compounds to 1 mM in water and sonicating them for 2 minutes in an ice bath. The compounds were then brought to 10× in 5% dextrose. After a 3-hour incubation with gentle shaking at 37° C. in a 5% $CO_2$ atmosphere, the assay plates were centrifuged at 1000×g for 10 minutes at 4° C. and plasma was drawn off and frozen at −80° C. Plasma samples were analyzed for TNF-α by ELISA (R & D Systems, Minneapolis, Minn.). Each assay point was tested in triplicate.

As shown in Table 1, representative compounds of the invention stimulate blood-borne cells to release TNF-α, with stimulatory values ranging from 0.008 µM to >10.0 µM. The stimulatory value is the compound concentration needed to stimulate TNF-α release equal to half the release obtained from the same whole blood sample with 10 ng/ml of LPS.

TABLE 1

Stimulation of cytokine release by compounds in vitro

| ER # | Structure | TNFa Stimulation Value (µM) |
|---|---|---|
| 804638 | 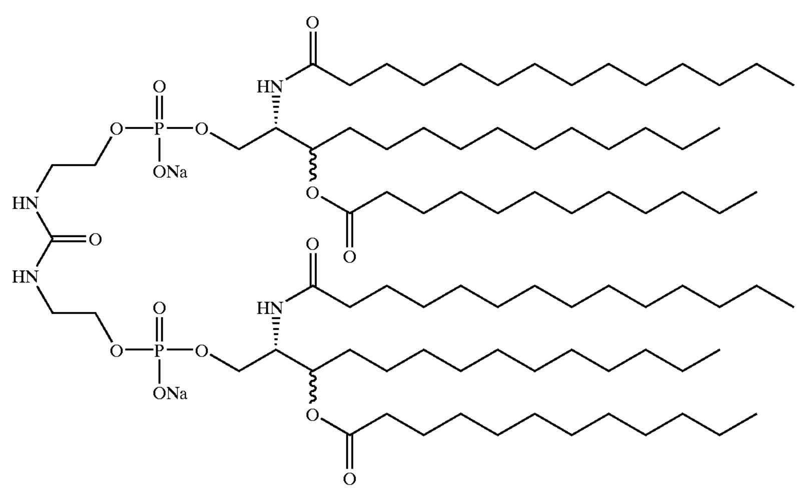 | 0.008 |
| 804666 | 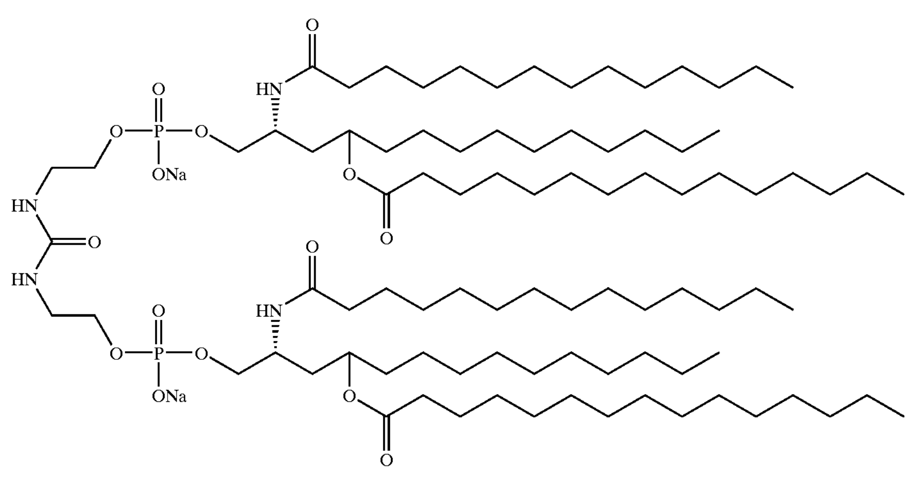 | 0.027 |

TABLE 1-continued

Stimulation of cytokine release by compounds in vitro

| ER # | Structure | TNFa Stimulation Value (μM) |
|---|---|---|
| 804874 | 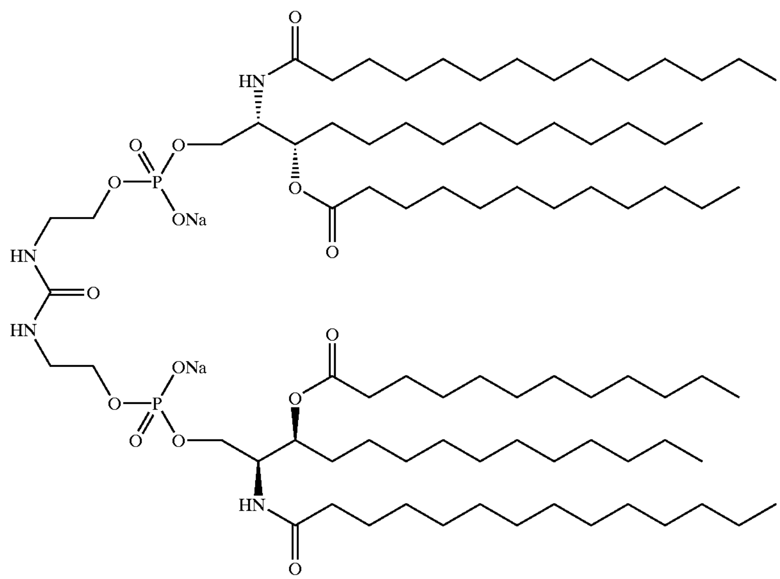 | 0.009 |
| 805028 | 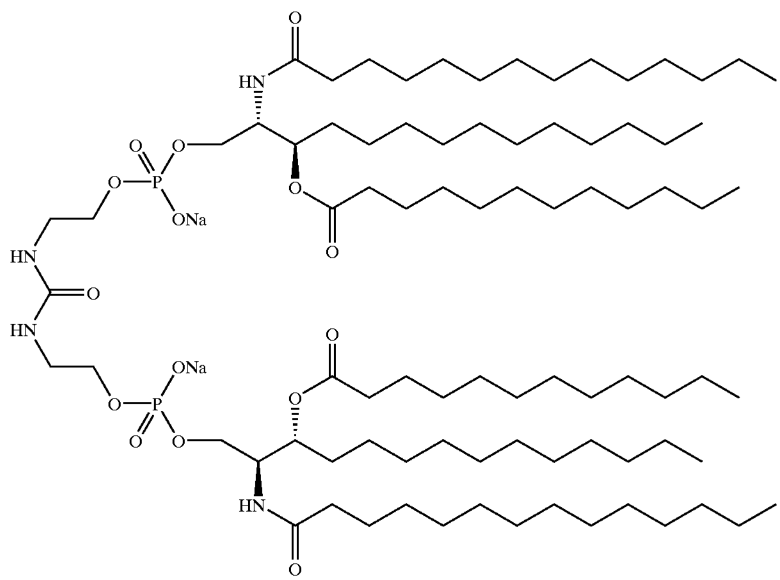 | 0.07 |

TABLE 1-continued

Stimulation of cytokine release by compounds in vitro

| ER # | Structure | TNFa Stimulation Value (µM) |
|---|---|---|
| 805520 Isomer A | 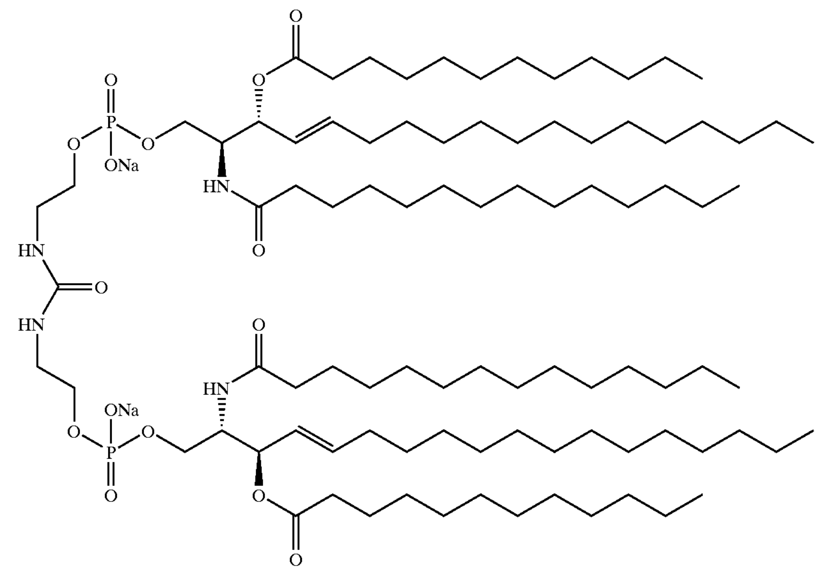 | >10.0 |
| 805270 Isomer B | 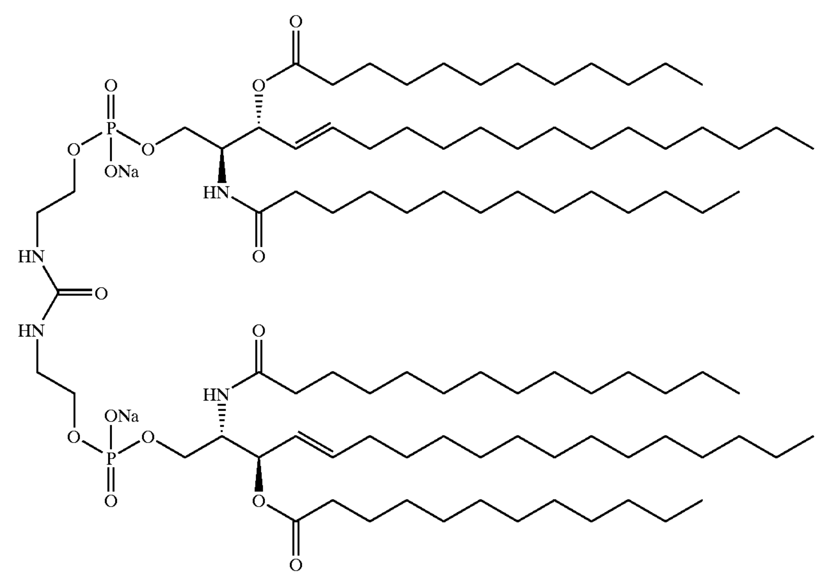 | >10.0 |

TABLE 1-continued
Stimulation of cytokine release by compounds in vitro
| ER # | Structure | TNFa Stimulation Value (μM) |
|---|---|---|
| 805271 | 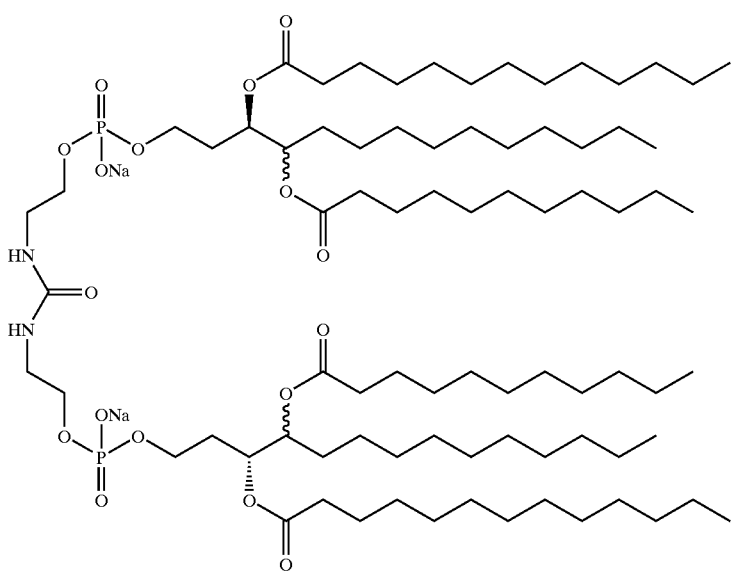 | 1.60 |
| 805274 | 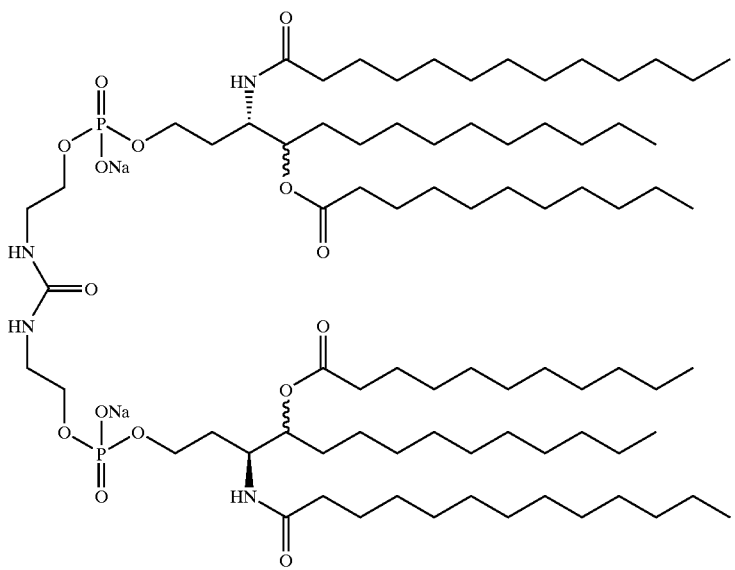 | 0.014 |

TABLE 1-continued

Stimulation of cytokine release by compounds in vitro

| ER # | Structure | TNFa Stimulation Value (μM) |
|---|---|---|
| 805328 | 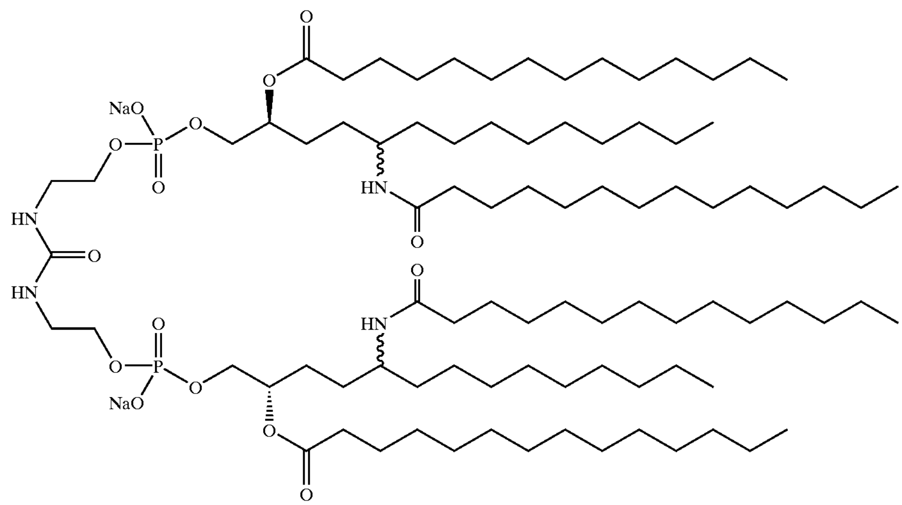 | 0.205 |
| 805329 | 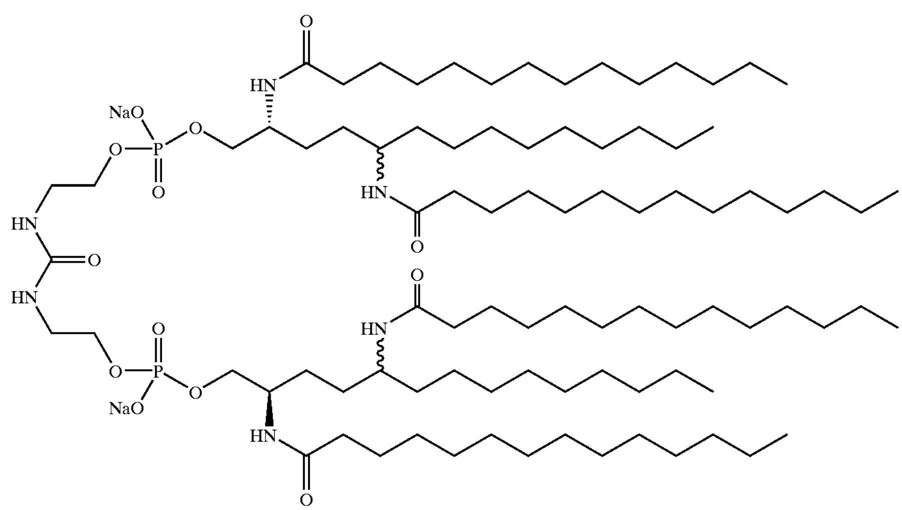 | 0.004 |

TABLE 1-continued

Stimulation of cytokine release by compounds in vitro

| ER # | Structure | TNFa Stimulation Value (μM) |
|---|---|---|
| 805517 | 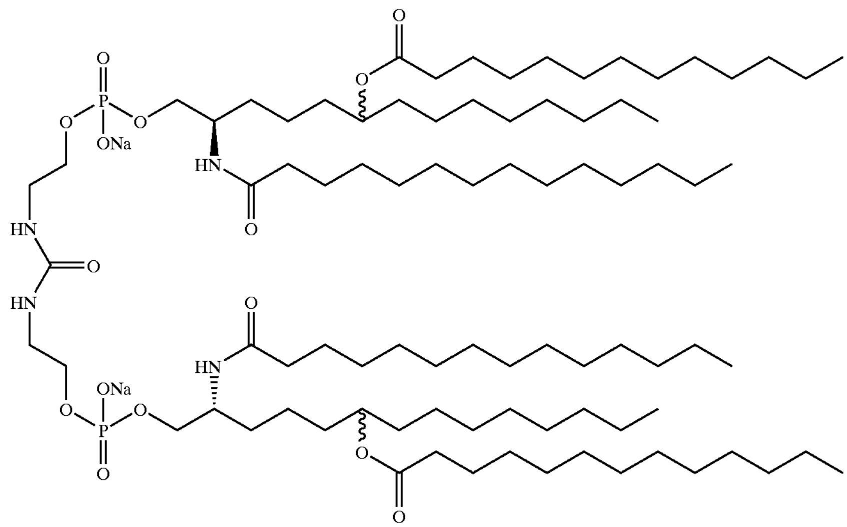 | 0.07 |
| 805518 Isomer A | 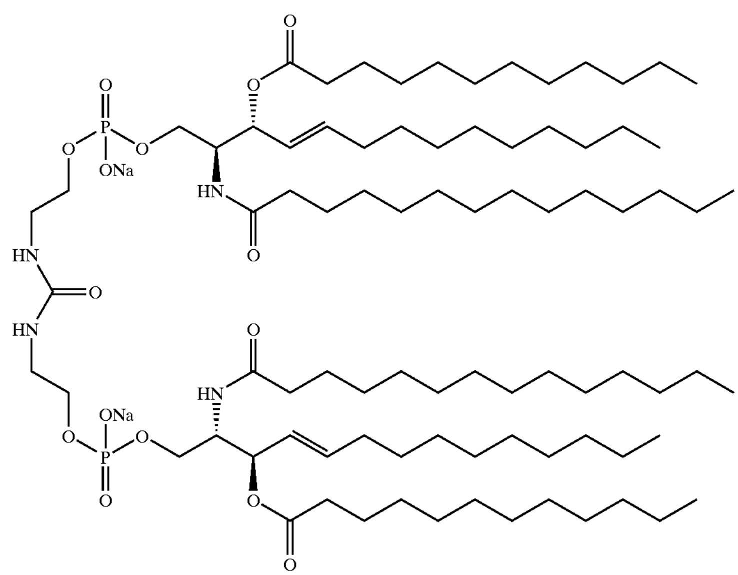 | .004 |

TABLE 1-continued

Stimulation of cytokine release by compounds in vitro

| ER # | Structure | TNFa Stimulation Value ($\mu$M) |
|---|---|---|
| 805519 Isomer B | (structure) | >10.0 |

Example 13

In vivo Induction of Antibody Response

The most critical test of adjuvant activity is the determination if the addition of a compound to an antigen preparation increases immune response by elevating the level of antibodies generated to that antigen when administered to a living animal.

To study the effects of the compounds of the invention on in vivo antibody production, Balb/c mice are injected with a test compound together with a protein such as tetanus toxoid. The tetanus toxoid is used as the immunogen at a dose of 0.25 $\mu$g. Female Balb/c mice (Charles River Laboratories; approximately 6–8 weeks old (18–25 g)) are injected with 200 $\mu$l of a mixture of antigen and adjuvant in PBS every three weeks for a total of three injections. Control animals are injected with Alum or PBS. All injections are performed subcutaneously at the back of the neck. Mice are bled two weeks after the second and third injections. Blood is collected by nicking the tail vein and collecting the drops into Becton Dickinson brand microtainer serum separator tubes. Serum is separated from the red cells by microcentrifugation and tested by ELISA for antigen specific IgG levels.

Immune response to the peptide can be tested by enzyme-linked immunosorbent assay (ELISA), which can quantitate levels of serum antibodies that bind to tetanus toxoid coated onto an ELISA plate.

Serum antibody is measured two weeks after the second immunization. As shown in Table 2, mice injected with the compounds of the invention along with tetanus toxoid antigen demonstrate greater immune response (higher levels of antibody) than those injected with the tetanus toxoid alone.

Tetanus toxoid from Accurate Chemical (cat #sstettox) is used as an immunizing antigen while the purified toxoid from List Biologicals (cat #191) is used as a target antigen for the ELISA assay.

For the preparation of antigen/adjuvant mixtures, lyophilized test compounds are reconstituted to 2 mg/ml with phosphate buffered saline (PBS; cat #P-3818; Sigma Chemical Co., St. Louis, Mo.) and sonicated in a chilled water bath for two minutes. Imject® Alum, purchased from Pierce Immunochemical, is used according to manufacturer's guidelines, and comprises 15% of the injection volume. The antigen is diluted in PBS and mixed with the test compound, or Alum such that the final concentration of the compound is 30 $\mu$g in the 200 $\mu$l injection volume. The mixtures are incubated at room temperature for at least 40 minutes prior to injection.

Antigen specific IgG levels are monitored by direct ELISA, in which antigen is passively coated onto 96 well Costar EIA/RIA plates. Plates are coated with 50 $\mu$l/well of tetanus toxoid at 3 $\mu$g/ml bicarbonate buffer, incubated overnight at 4° C. and washed 3× with PBS containing 0.05% Tween 20 (PBS-t) in an automated plate washer. Plates are then blocked with 200 $\mu$l/well of 0.5% gelatin in PBS for 1 hour at room temperature (RT) and washed 3× with PBS-t. Mouse serum is diluted in PBS-t containing 1.0% BSA and 100 $\mu$l of various dilutions are added to the antigen coated wells, incubated at RT for 1 hour and again washed 3× with PBS-t. Biotinylated rat anti-mouse IgG (Zymed, South San Francisco, Calif.) is diluted to 50 ng/ml in PBS-t and 100 $\mu$l/well is applied. After incubation at RT for 1 hour, the wells are washed 3× with PBS-t, followed by the addition of 40 ng/ml streptavidin-horseradish peroxidase conjugate (Southern Biotechnology Associates Inc., Birmingham, Ala.) in PBS-t. After incubation for 30 minutes at RT, the wells are again washed 3× with PBS-t. Wells are then incubated in 100 $\mu$l TMB substrate (Kirkegaard and Perry Labs) for 5 minutes. Color development is stopped with the addition of an equal volume of 1M phosphoric acid, and the absorbance is read at 450 nm on a Titertek Multiscan plate reader with Deltasoft software analysis package.

For quantitation of antigen-specific IgG levels, curves are compared to a known standard. A total IgG assay using directly adhered known amounts of purified IgG (purchased from Southern Biotech) as an IgG standard curve is run in conjunction with the direct ELISA on the tetanus toxoid. This allows detection of bound antibody by the same reagents used to measure antigen-specific capture of antibodies. The same reagent solutions used for detection of the antibodies bound to tetanus toxoid, namely biotinylated anti-IgG followed with HRP-streptavidin, are simultaneously applied to the total IgG quantitative assay and to the antigen-specific assay. Hence, the signal from the binding of the purified IgG standard curve is equivalent to that generated to equal amounts of IgG bound in the anti-tetanus toxoid assay. The amount of tetanus toxoid-specific antibody in the serum is then interpolated from the purified IgG standard using a 4-parameter curve fit (DeltaSoft 3 software package).

TABLE 2

Adjuvant activity of compounds in vivo

| Material administered with tetanus toxoid | Mean concentration of tetanus toxoid-specific IgG (6 mice/group) (μg/ml) | Standard deviation |
|---|---|---|
| ER-804638 | 2813 | 549 |
| ER-804666 | 2158 | 375 |
| ER-804874 | 5640 | 2001 |
| ER-805028 | 1322 | 179 |
| ER-805270 | 1995 | 731 |
| ER-805271 | 2010 | 262 |
| ER-805274 | 3218 | 439 |
| PBS | 423 | 351 |
| alum | 2119 | 175 |

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A compound of the formula I:

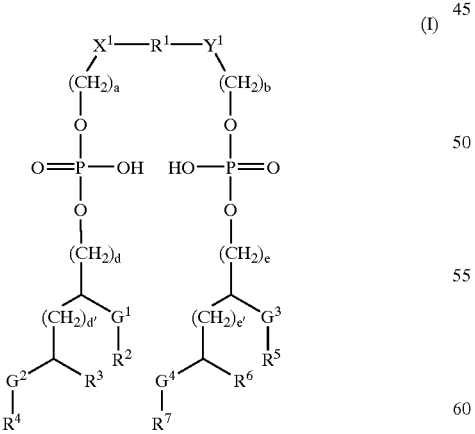

(I)

wherein $R^1$ is selected from the group consisting of
(a) —C(O)—;
(b) —C(O)—$C_{1-14}$ alkylene-C(O)— or —C(O)—$C_{1-14}$ alkylene-C(O)—, wherein the $C_{1-14}$ alkylene or $C_{1-14}$ alkenylene is optionally substituted with hydroxy, $C_{1-6}$ alkoxy, $C_{1-6}$ alkylenedioxy, carboxy, $C_{1-6}$ alkoxycarbonyl, $C_{1-6}$ carbamoyl, $C_{1-6}$ acylamino, $C_{1-6}$ alkylamino, or (aryl)$C_{1-6}$ alkyl, wherein said aryl moiety of said (aryl)$C_{1-6}$ alkyl is optionally substituted with $C_{1-6}$ alkyl, $C_{1-6}$ alkoxy, $C_{1-6}$ alkylamino, ($C_{1-6}$ alkoxy)$C_{1-6}$ alkylamino, ($C_{1-6}$ alkylamino)$C_{1-6}$ alkoxy, —O—$C_{1-6}$ alkylene-NH—$C_{1-6}$alkylene-O—$C_{1-6}$ alkyl, —O—$C_{1-6}$ alkylene-NH—C(O)—$C_{1-6}$ alkylene-C(O)OH, or —O—$C_{1-6}$ alkylene-NH—C(O)—$C_{1-6}$ alkylene-C(O)—$C_{1-6}$ alkyl;
(c) $C_2$ to $C_{15}$ straight or branched chain alkyl optionally substituted with hydroxy or alkoxy; and
(d) —C(O)—$C_{6-12}$ arylene-C(O)— wherein said arylene is optionally substituted with $C_{1-6}$ alkyl, hydroxy, $C_{1-6}$ alkoxy, halogen, nitro or amino;

a and b are independently an integer from 0 to about 4;
d and e are independently an integer from 1 to about 6;
d' and e' are independently an integer from 0 to about 2;
$X^1$ and $Y^1$ are independently selected from the group consisting of a null, oxygen, —NH—, —N(C(O)$C_{1-4}$ alkyl)-, and —N($C_{1-4}$ alkyl)-;
$G^1$, $G^2$, $G^3$, and $G^4$ are independently selected from the group consisting of oxygen, methylene, —NH—, —N($C_{1-4}$ alkyl)-, —N[C(O)—$C_{1-4}$ alkyl]-, —NH—C(O)—, —NH— $SO_2$—, —C(O)—O—, —C(O)—NH—, —O—C(O)—, —O—C(O)—NH—, —O—C(O)—O—, —NH—C(O)—NH—, —C(O)NH—, C(O)N($C_{1-4}$ alkyl), and —S(O)$_n$—, where n is 0, 1, or 2;
$R^2$, $R^3$, $R^4$, $R^5$, $R^6$, and $R^7$ are independently selected from the group consisting of:
(a) $C_1$ to $C_{20}$ straight chain or branched chain alkyl which is optionally substituted with halo, oxo, hydroxy or alkoxy;
(b) $C_2$ to $C_{20}$ straight chain or branched chain alkenyl, alkynyl, or dialkenyl which is optionally substituted with halo, oxo, hydroxy or alkoxy; and (c)

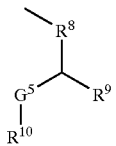

wherein $R^8$ is $C_{1-6}$ straight or branched chain alkyl or $C_{2-6}$ straight or branched chain alkenyl, alkynyl, or dialkenyl;
$G^5$ is selected from the group consisting of oxygen, methylene, arylene, —NH—, —N($C_{1-4}$ alkyl)-, —N(C(O)—$C_{1-4}$ alkyl)-, —NH—C(O)—, —NH—$SO_2$—, —C(O)—O—, —C(O)—NH—, —O—C(O)—, —O—C(O)—NH—, —O—C(O)—O—, —NH—C(O)—NH—, and —S(O)$_n$—, where n is 0, 1, or 2;
$R^9$ and $R^{10}$ are independently selected from the group consisting of
(i) $C_1$ to $C_{20}$ straight chain or branched chain alkyl which is optionally substituted with halo, oxo, hydroxy or alkoxy; and
(ii) $C_2$ to $C_{20}$ straight chain or branched chain alkenyl, alkynyl, or dialkenyl which is optionally substituted with halo, oxo, hydroxy or alkoxy;

or any one or two of $G^1R^2$, $G^2R^4$, $G^3R^5$, and $G^4R^7$ may together be a hydrogen atom or hydroxyl;

or a pharmaceutically acceptable salt thereof.

2. The compound according to claim 1, wherein each of a and b is 2.

3. The compound according to claim 1, wherein each of $X^1$ and $Y^1$ is NH.

4. The compound according to claim 1, wherein each of d and e is 1 or 2.

5. The compound according to claim 1, wherein each of d' and e' is 0, 1, or 2.

6. The compound according to claim 1, wherein each of d and e is 1, and each of d' and e' is 0.

7. The compound according to claim 1, wherein each of d and e is 1, and each of d' and e' is 1 or 2.

8. The compound according to claim 1, wherein $R^1$ is —C(O)— or —C(O)—$C_{1-14}$ alkylene-C(O)—, wherein the $C_{1-14}$ alkylene is optionally substituted with one or two substituents selected from the group consisting of hydroxy, $C_{1-6}$ alkoxy, $C_{1-6}$ alkylenedioxy, $C_{1-6}$ alkylamino, or (aryl)$C_{1-6}$ alkyl, wherein said aryl moiety of said (aryl)$C_{1-6}$ alkyl is optionally substituted with $C_{1-6}$ alkyl, $C_{1-6}$alkoxy, $C_{1-6}$ alkylamino, ($C_{1-6}$ alkoxy)$C_{1-6}$ alkylamino, ($C_{1-6}$ alkylamino)$C_{1-6}$ alkoxy, —O—$C_{1-6}$ alkylene-NH—$C_{1-6}$alkylene-O—$C_{1-6}$ alkyl, —O—$C_{1-6}$ alkylene-NH—C(O)—$C_{1-6}$ alkylene-C(O)OH, or —O—$C_{1-6}$ alkylene-NH—C(O)—$C_{1-6}$ alkylene-C(O)—$C_{1-6}$ alkyl.

9. The compound according to claim 1, wherein $G^1$, $G^2$, $G^3$, and $G^4$ are each independently selected from the group consisting of —NH—C(O)— and —O—C(O)—.

10. The compound according to claim 1, wherein at least two of $R^2$–$R^7$, $R^9$, and $R^{10}$ are $C_{6-20}$ straight or branched chain alkyl, alkenyl, or dialkenyl, any of which groups may be optionally substituted with one or two substituents selected from the group consisting of halo, oxo, hydroxy, and alkoxy.

11. The compound according to claim 1, wherein at least four of $R^2$–$R^7$, $R^9$, and $R^{10}$ are $C_{6-20}$ straight or branched chain alkyl, alkenyl, or dialkenyl, any of which groups may be optionally substituted with one or two substituents selected from the group consisting of halo, oxo, hydroxy, and alkoxy.

12. The compound according to claim 1, wherein at least six of $R^2$–$R^7$, $R^9$, and $R^{10}$ are $C_{6-20}$ straight or branched chain alkyl, alkenyl, or dialkenyl, any of which groups may be optionally substituted with one or two substituents selected from the group consisting of halo, oxo, hydroxy, and alkoxy.

13. The compound according to claim 1, wherein at least two of $R^2$–$R^7$, $R^9$, and $R^{10}$ are $C_{8-15}$ straight or branched chain alkyl, alkenyl, or dialkenyl, any of which groups may be optionally substituted with one or two substituents selected from the group consisting of halo, oxo, hydroxy, and alkoxy.

14. The compound according to claim 1, wherein at least four of $R^2$–$R^7$, $R^9$, and $R^{10}$ are $C_{8-15}$ straight or branched chain alkyl, alkenyl, or dialkenyl, any of which groups may be optionally substituted with one or two substituents selected from the group consisting of halo, oxo, hydroxy, and alkoxy.

15. The compound according to claim 1, wherein at least six of $R^2$–$R^7$, $R^9$, and $R^{10}$ are $C_{8-15}$ straight or branched chain alkyl, alkenyl, or dialkenyl, any of which groups may be optionally substituted with one or two substituents selected from the group consisting of halo, oxo, hydroxy, and alkoxy.

16. An immunological adjuvant formulation comprising a compound of the formula I:

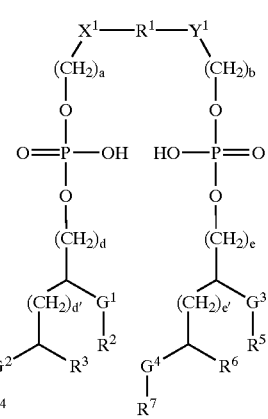

(I)

wherein $R^1$ is selected from the group consisting of (a) —C(O)—;

(b) —C(O)—$C_{1-14}$ alkylene-C(O)— or —C(O)—$C_{1-14}$ alkenylene-C(O)—, wherein the $C_{1-14}$ alkylene or $C_{1-14}$ alkenylene is optionally substituted with hydroxy, $C_{1-6}$ alkoxy, $C_{1-6}$ alkylenedioxy, carboxy, $C_{1-6}$ alkoxycarbonyl, $C_{1-6}$carbamoyl, $C_{1-6}$ acylamino, $C_{1-6}$ alkylamino, or (aryl)$C_{1-6}$ alkyl, wherein said aryl moiety of said (aryl)$C_{1-6}$ alkyl is optionally substituted with $C_{1-6}$ alkyl, $C_{1-6}$ alkoxy, $C_{1-6}$ alkylamino, ($C_{1-6}$ alkoxy)$C_{1-6}$ alkylamino, ($C_{1-6}$ alkylamino)$C_{1-6}$ alkoxy, —O—$C_{1-6}$ alkylene-NH—$C_{1-6}$alkylene-O—$C_{1-6}$ alkyl, —O—$C_{1-6}$alkylene-NH—C(O)—$C_{1-6}$ alkylene-C(O)OH, or —O—$C_{1-6}$ alkylene-NH—C(O)—$C_{1-6}$ alkylene-C(O)—$C_{1-6}$ alkyl;

(c) $C_2$ to $C_{15}$ straight or branched chain alkyl optionally substituted with hydroxy or alkoxy; and (d) —C(O)—$C_{6-12}$ arylene-C(O)— wherein said arylene is optionally substituted with $C_{1-6}$ alkyl, hydroxy, $C_{1-6}$ alkoxy, halogen, nitro or amino;

a and b are independently an integer from 0 to about 4;

d and e are independently an integer from 1 to about 6;

d' and e' are independently an integer from 0 to about 2;

$X^1$ and $Y^1$ are independently selected from the group consisting of a null, oxygen, —NH—, —N(C(O)$C_{1-4}$ alkyl)-, and —N($C_{1-4}$ alkyl)-;

$G^1$, $G^2$, $G^3$, and $G^4$ are independently selected from the group consisting of oxygen, methylene, —NH—, —N($C_{1-4}$ alkyl)-, —N[C(O)—$C_{1-4}$ alkyl]-, —NH—C(O)—, —NH—SO$_2$—, —C(O)—O—, —C(O)—NH—, —O—C(O)—, —O—C(O)—NH—, —O—C(O)—O—, —NH—C(O)—NH—, and —C(O)NH—, C(O)N($C_{1-4}$ alkyl), —S(O)$_n$—, where n is 0, 1, or 2;

$R^2$, $R^3$, $R^4$, $R^5$, $R^6$, and $R^7$ are independently selected from the group consisting of:

(a) $C_1$ to $C_{20}$ straight chain or branched chain alkyl which is optionally substituted with halo, oxo, hydroxy or alkoxy;

(b) $C_2$ to $C_{20}$ straight chain or branched chain alkenyl, alkynyl, or dialkenyl which is optionally substituted with halo, oxo, hydroxy or alkoxy; and (c) 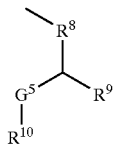

wherein
$R^8$ is $C_{1-6}$ straight or branched chain alkyl or $C_{2-6}$ straight or branched chain alkenyl, alkynyl, or dialkenyl;
$G^5$ is selected from the group consisting of oxygen, methylene, arylene, —NH—, —N($C_{1-4}$ alkyl)-, —N(C(O)—$C_{1-4}$ alkyl)-, —NH—C(O)—, —NH—SO$_2$—, —C(O)—O—, —C(O)—NH—, —O—C(O)—, —O—C(O)—NH—, —O—C(O)—O—, —NH—C(O)—NH—, and —S(O)$_n$—, where n is 0, 1, or 2;
$R^9$ and $R^{10}$ are independently selected from the group consisting of
(i) $C_1$ to $C_{20}$ straight chain or branched chain alkyl which is optionally substituted with halo, oxo, hydroxy or alkoxy; and
(ii) $C_2$ to $C_{20}$ straight chain or branched chain alkenyl, alkynyl, or dialkenyl which is optionally substituted with halo, oxo, hydroxy or alkoxy;
or any one or two of $G^1R^2$, $G^2R^4$, $G^3R^5$, and $G^4R^7$ may together be a hydrogen atom or hydroxyl;
or a pharmaceutically acceptable salt thereof; and
a pharmaceutically acceptable carrier, diluent or excipient.

* * * * *